(12) United States Patent
Gillen et al.

(10) Patent No.: US 7,820,707 B2
(45) Date of Patent: Oct. 26, 2010

(54) HETEROCYCLIC DERIVATIVES

(75) Inventors: Kevin James Gillen, Newhouse (GB); Craig Jamieson, Newhouse (GB); John Kinnaird Ferguson MacLean, Newhouse (GB); Elizabeth Margaret Moir, Newhouse (GB); Zoran Rankovic, Newhouse (GB)

(73) Assignee: N.V. Organon, Oss (NL)

( * ) Notice: Subject to any disclaimer, the term of this patent is extended or adjusted under 35 U.S.C. 154(b) by 105 days.

(21) Appl. No.: 11/771,198

(22) Filed: Jun. 29, 2007

(65) Prior Publication Data

US 2008/0255086 A1 Oct. 16, 2008

Related U.S. Application Data

(60) Provisional application No. 60/818,607, filed on Jul. 5, 2006.

(30) Foreign Application Priority Data

Jul. 4, 2006 (EP) ................................. 06116592

(51) Int. Cl.
*A61K 31/4155* (2006.01)
*A61K 31/416* (2006.01)
*C07D 231/56* (2006.01)
*C07D 231/10* (2006.01)

(52) U.S. Cl. .................... 514/405; 514/406; 548/361.1; 548/365.7

(58) Field of Classification Search .............. 548/356.1, 548/364.1, 365.7, 361.1; 514/405, 406
See application file for complete search history.

(56) References Cited

U.S. PATENT DOCUMENTS

2004/0171603 A1 9/2004 Pato

FOREIGN PATENT DOCUMENTS

| WO | WO 2005/033102 | 4/2005 |
|----|----------------|--------|
| WO | WO 2005/040110 | 5/2005 |
| WO | WO 2005/070916 | 8/2005 |
| WO | WO 2006/044826 | 4/2006 |

OTHER PUBLICATIONS

"Depression." Retrieved online via the internet [Mar. 24, 2009] URL: http://www.nlm.nih.gov/medlineplus/depression.html.*
"Alzheimer's Stages." Retrieved online via the internet [Mar. 24, 2009] URL: http://www.mayoclinic.com/health/alzheimers-stages/AZ00041.*
"Alzheimer's Treatment." Retrieved online via the internet [Mar. 24, 2009] URL: http://www.medindia.net/patients/patientinfo/Alzheimers_treatment.htm.*
Morissette et al. Advanced Drug Delivery Reviews 2004, 56, 275-300.*
Vippagunta, Sudha R. "Crystalline Solids." Advanced Drug Delivery Reviews 48(2001): 3-26.*

Arai et. al., "Benzamide-Type AMPA Receptor Modulators Form Two Subfamilies with Distinct Modes of Action," *J Pharmacol Exp. Ther.* 303 (2002) 1075-1085.
Pirotte et al., "4*H*-1,2,4-Pyridothiadiazine 1,1-Dioxides and 2,3-Dihydro-4*H*-1,2,4-pyridothiadiazine 1,1-Dioxides Chemically Related to Diazoxide and Cyclothiazide as Powerful Positive Allosteric Modulators of (R/S)-2-Amino-3-(3-hydroxy-5-methylisoxazol-4-yl)propionic Acid Receptors: Design, Synthesis, Pharmacology, and Structure-Activity Relationships," *J Med Chem.* 41 (1998) 2946-2959.
Lynch, G., "Glutamate-based therapeutic approaches: ampakines," *Current Opinion in Pharmacology* 6 (2006) 82-88.
Ornstein et. al., "Biarylpropylsulfonamides as Novel, Potent Potentiators of 2-Amino-3-(5-methyl-3-hydroxyisoxazol-4-yl)-propanoic Acid (AMPA) Receptors," *J Med. Chem.* 43 (2000) 4354-4358.
Yamada, K.A., "Therapeutic Potential of Positive AMPA Receptor Modulators in the Treatment of Neurological Disease," *Exp. Opin. Invest. Drugs* 9 (2000) 765-778.
Abstract; Acc. No. 2004:1697041; Chembridge Screening Library; Jan. 12, 2005; Reg. No. 332944-69-1.
Abstract; Acc. No. 2004:1695877; Chembridge Screening Library; Jan. 12, 2005; Reg. No. 332944-89-5.
Abstract; Acc. No. 2004:1700663; Chembridge Screening Library; Jan. 12, 2005; Reg. No. 332944-91-9.
Abstract; Acc. No. 2004:3287067; TimTec Overseas Stock; Aug. 1, 2005; Reg. No. 489408-02-8.
Abstract; Acc. No. 2004:2935795; TimTec Overseas Stock; Aug. 1, 2005; Reg. No. 489407-99-0.
Abstract; Acc. No. 2004:2944145; TimTec Overseas Stock; Aug. 1, 2005; Reg. No. 332943-84-7.

(Continued)

*Primary Examiner*—Kamal A Saeed
*Assistant Examiner*—Samantha L Shterengarts
(74) *Attorney, Agent, or Firm*—Susan L. Hess

(57) ABSTRACT

The present invention relates to a heterocyclic derivative according to formula I

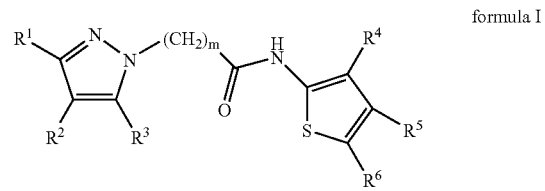

formula I wherein the variables are defined as in the specification, or to a pharmaceutically acceptable salt or solvate thereof. The present invention also relates to a pharmaceutical composition comprising said heterocyclic derivatives and to their use in therapy, for instance in the treatment or prevention of psychiatric diseases where an enhancement of synaptic responses mediated by AMPA receptors is required, including schizophrenia, depression and Alzheimer's disease.

10 Claims, No Drawings

OTHER PUBLICATIONS

Abstract; Acc. No. 2004:2935795; TimTec Overseas Stock; Aug. 1, 2005; Reg. No. 489407-99-0.
Abstract; Acc. No. 2004:3286992; TimTec Overseas Stock; Aug. 1, 2005; Reg. No. 512809-08-4.
Abstract; Acc. No. 2004:2948236; TimTec Overseas Stock; Aug. 1, 2005; Reg. No. 332944-93-1.
Abstract; Acc. No. 2004:3293567; TimTec Overseas Stock; Aug. 1, 2005; Reg. No. 512808-90-1.
Abstract; Acc. No. 2004:2894847; TimTec Overseas Stock; Aug. 1, 2005; Reg. No. 491831-90-4.
Abstract; Acc. No. 2001:2277483; ChemDiv. Inc. Proudct Library; Apr. 25, 2003; Reg. No. 357611-67-7.
Abstract; Acc. No. 2001:907829; AsInEx Express Gold Collection; Jan. 31, 2006; Reg. No. 332943-95-0.
Abstract; Acc. No. 2001:711318; AsInEx Express Gold Collection; Jan. 31, 2006; Reg. No. 332943-93-8.
Abstract; Acc. No. 2000:914363; ChemStar Product List; Apr. 6, 2006; Reg. No. 299406-09-0.
International Search Report for PCT/EP2007/005851 mailed Nov. 6, 2007.
Written Opinion for International Application No. PCT/EP2007/005851 mailed on Nov. 6, 2007.

* cited by examiner

HETEROCYCLIC DERIVATIVES

CROSS REFERENCE TO RELATED APPLICATIONS

This application claims the benefit of U.S. Provisional Application No. 60/818,607, filed Jul. 5, 2006, and claims priority of European Patent Application No. 06116592.4, filed Jul. 4, 2006.

BACKGROUND OF THE INVENTION

1. Field of the Invention

The present invention relates to heterocyclic derivatives, to pharmaceutical compositions comprising these compounds and to their use in therapy, in particular to their use for the manufacture of a medicament for the treatment or prevention of psychiatric diseases where an enhancement of synaptic responses mediated by AMPA receptors is required.

2. Description of Related Art

L-glutamate is the most abundant excitatory neurotransmitter located in the mammalian central nervous system (CNS). L-glutamate plays a significant role in the control of cognition, mood and motor function and these processes are imbalanced in psychiatric and neurological disorders. The physiological effects of glutamate are mediated through two receptor families, the metabotropic (G-protein coupled) receptors and the ionotropic (ligand-gated ion channels) receptors. The ionotropic receptors are responsible for mediating the fast synaptic response to extracellular L-glutamate. The ionotropic glutamate receptors are separated into three subclasses on the basis of molecular and pharmacological differences and are named after the small molecule agonists which were originally identified to selectively activate them: AMPA (α-amino-3-hydroxy-5-methyl-4-isoxazole-propionic acid), NMDA (N-methyl-D-aspartate) and kainate (2-carboxy-3-carboxymethyl-4-isopropenylpyrrolidine).

The importance of AMPA receptors in brain physiology is widely recognised and it has been shown that AMPA receptors control the majority of fast excitatory amino acid transmission in the CNS and also contribute to synaptic plasticity playing a role in a variety of physiological processes such as learning and memory. To this end there has been a growing appreciation of the utility of positive allosteric modulators of the AMPA receptor for a variety of clinical indications including schizophrenia, depression and Alzheimer's disease.

AMPA receptor subunits are encoded by four distinct genes (termed GluR1 to 4), each representing proteins of around 900 amino acids. The individual sub-units consist of a large extracellular N-terminal domain, an extracellular ligand binding site for L-glutamate formed by domains designated S1 and S2. The transmembrane domain consists of three transmembrane regions, M1, M3 and M4 together with the re-entrant loop M2. This is then followed by a long intracellular C-terminal domain. All four AMPA receptor subunits contain so-called 'flip' and 'flop' splice variants which differ in alternate slicing of 38 amino acid encoding exons (differing by less than 10 amino acids) in the S2 extracellular domain. Further heterogeneity of the AMPA receptors results from RNA editing, the most significant being the Q/R site located in the pore region (M2) of the GluR2 subunit. The R variant, which a large proportion of native GluR2 subunits are believed to comprise, is characterised by significantly reduced calcium permeability. A further R/G editing site is located in the S2 domain of GluR2, GluR3 and GluR4 with the G form exhibiting an acceleration in the kinetics of recovery from desensitisation.

The kinetics of desensitisation and deactivation are important functional properties of the AMPA receptor that control the magnitude and duration of the synaptic response to glutamate. The processes of desensitisation and deactivation can be modulated by AMPA receptor positive allosteric modulators that bind remotely from the agonist binding site, yet influence agonist binding, or indeed agonist mediated conformational changes in the receptor associated with gating and/or desensitisation. Consequently there are continued efforts to develop drugs that specifically target these properties and which will have therapeutic potential in the treatment of a wide variety of CNS disorders associated with diminished glutamatergic signalling. These conditions include age-related memory impairment, Alzheimer's Disease, Parkinson's Disease, depression, psychosis, cognitive defects associated with psychosis, attention deficit disorder and attention deficit hyperactivity disorder.

A variety of structural classes of compounds are known which act as AMPA receptor modulators (see G. Lynch, *Current Opinion in Pharmacology*, 2006, 6, 82-88 for a recent review). For example, there are the so-called benzamide compounds related to aniracetam (see A. Arai et al., *J Pharmacol Exp. Ther.*, 2002, 30, 1075-1085), the benzothiadiazine derivatives such as S-18689 (see B. Pirotte, *J. Med. Chem.*, 1998, 41, 2946-2959) and the biarylpropylsulfonamide derivatives (see P. L. Ornstein et al., *J. Med. Chem.* 2000, 43, 4354-4358). Another class of AMPA receptor modulators was disclosed in International Patent Applications WO 2005/040110 and WO 2005/070916 which detail various heterocyclic compounds as being of utility as glutamate modulators. Compounds in each of these classes exhibit varying degrees of potentiation of the AMPA receptor.

Sustained AMPA receptor activation, however, is also associated with seizures and other proconvulsant side effects (Yamada K. A., *Exp. Opin. Invest. Drugs* 2000, 9, 765-777). Consequently there remains a need for further AMPA receptor modulators which have an optimal separation between beneficial therapeutic effects and unwanted neurotoxic effects.

US 2004/171603 A1 discloses heterocyclic compounds indicated to be protein kinase inhibitors useful for the treatment of mycobacterial infections. WO 2005/033102 discloses certain thiophene based compounds indicated to be useful for the treatment of diseases associated with ATP-utilizing enzyme inhibition. WO 2006/044826 discloses further thiophene based heterocyclic compounds useful as anti-tumor agents. None of these publications relate to compounds useful for the treatment or prevention of psychiatric diseases where an enhancement of synaptic responses mediated by AMPA receptors is required.

BRIEF SUMMARY OF THE INVENTION

In a first aspect the present invention relates to a heterocyclic derivative according to formula I

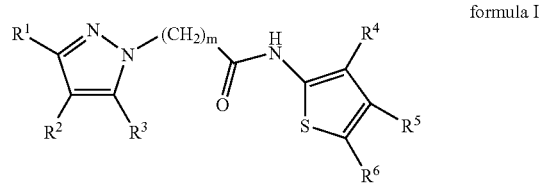

formula I wherein $R^1$ is $C_{1-4}$alkyl or CN, said $C_{1-4}$alkyl being optionally substituted with 1-3 halogens;

$R^2$ is $C_{1-4}$alkyl, $C_{1-4}$alkyloxy, or $C_{1-5}$acyl, said $C_{1-4}$alkyl being optionally substituted with a substituent selected from OH, $C_{1-4}$alkyloxy and $NR^7R^8$ or $R^2$ together with $R^3$ forms a 5 to 7 membered unsaturated carbocyclic ring optionally comprising a N.

$R^3$ is H or methyl optionally substituted with hydroxy or 1-3 halogens or $R^3$ together with $R^2$ forms a 5 to 7 membered unsaturated carbocyclic ring optionally comprising a N $R^4$ is hydroxymethyl, $CO_2H$ or $CONR^9R^{10}$;

$R^5$ and $R^6$ are independently H, $C_{1-4}$alkyl or $C_{3-8}$cycloalkyl or $R^5$ together with $R^6$ forms a 5 or 6 membered unsaturated carbocyclic ring optionally comprising a heteroatomic moiety selected from O and $NR^{11}$;

$R^7$ and $R^8$ are independently H, $C_{1-6}$alkyl or $C_{3-8}$cycloalkyl, said $C_{1-6}$alkyl being optionally substituted with hydroxy, $C_{1-4}$ alkyloxy or 1-3 halogens; or $R^7$ and $R^8$ together with the N to which they are bonded form a 3-6 membered saturated heterocyclic ring;

$R^9$ is H or $C_{1-4}$alkyl optionally substituted with 1-3 groups selected from hydroxy, $C_{1-6}$ alkyloxy, $NR^{12}R^{13}$, $CONR^{14}R^{15}$ and Y, wherein Y is a 5-6 membered heteroaryl comprising 1-2 heteroatoms selected from O, N and S, or wherein Y is $C_{3-8}$cycloalkyl optionally comprising 1-2 heteroatomic moieties selected from O, S, $SO_2$ and $NR^6$, Y being optionally substituted with 1-2 substituents selected from $C_{1-4}$alkyl, $CH_2OH$ and $CH_2NR^{17}R^{18}$;

or $R^9$ is $C_{3-8}$cycloalkyl comprising a heteroatomic moiety selected from O, S and $NR^{16}$;

or $R^9$ and $R^{10}$ together with the N to which they are bonded form a 5-6 membered saturated heterocyclic ring optionally comprising a heteroatomic moiety selected from O and $NR^{16}$;

$R^{10}$ is H or methyl with the proviso that when $R^9$ is methyl $R^{10}$ must be $C_{1-4}$alkyl or $R^{10}$ and $R^9$ together with the N to which they are bonded form a 5-6 membered saturated heterocyclic ring optionally comprising a heteroatomic moiety selected from O and $NR^{16}$;

$R^{11}$ is H or methyl;

$R^{12}$ is H or $C_{1-4}$alkyl or $R^{12}$ and $R^{13}$ together with the N to which they are bonded form a 5-6 membered saturated heterocyclic ring optionally comprising a heteroatomic moiety selected from O, S and $NR^{19}$;

$R^{13}$ is H, $C_{1-4}$alkyl, $CO_2R^{20}$ or $SO_2R^{20}$ or $R^{13}$ and $R^{12}$ together with the N to which they are bonded form a 5-6 membered saturated heterocyclic ring optionally comprising a heteroatomic moiety selected from O, S and $NR^{19}$;

$R^{14}$-$R^{19}$ are independently H or $C_{1-4}$alkyl;

$R^{20}$ is $C_{1-4}$alkyl and m is 1-4 with the proviso that when $R^1$ is $CF_3$, $R^2$ together with $R^3$ forms a 6 membered unsaturated carbocyclic ring and $R^5$ together with $R^6$ forms a 6 membered unsaturated carbocyclic ring, $R^4$ cannot be $CONH_2$ or a pharmaceutically acceptable salt or solvate thereof.

DETAILED DESCRIPTION OF THE INVENTION

The term $C_{1-6}$ alkyl, as used herein, represents a branched or unbranched alkyl group having 1-6 carbon atoms. Examples of such groups are methyl, ethyl, isopropyl, tertiary butyl and neopentyl Similarly the term $C_{1-4}$ alkyl, as used herein, represents a branched or unbranched alkyl group having 1-4 carbon atoms.

The term $C_{3-8}$ cycloalkyl, as used herein, represents a branched or unbranched cyclic alkyl group having 3-8 carbon atoms. Examples of such groups are cyclopropyl, cyclopentyl and 2-methylcyclohexyl.

The term $C_{1-6}$ alkyloxy, as used herein, represents a branched or unbranched alkyloxy group having 1-6 carbon atoms. Examples of such groups are methoxy, ethoxy, isopropyloxy and tertiary butyloxy. Similarly the term $C_{1-4}$ alkyloxy, as used herein, represents a branched or unbranched alkyloxy group having 1-4 carbon atoms.

The term $C_{3-6}$ cycloalkyloxy, as used herein, represents a branched or unbranched cyclic alkyloxy group having 3-6 carbon atoms. Examples of such groups are cyclopropyloxy, cyclopentyloxy and 2-methylcyclopentyloxy. Similarly, the term $C_{4-6}$ cycloalkyloxy represents a branched or unbranched cyclic alkyloxy group having 4-6 carbon atoms.

The term $C_{1-5}$ acyl, as used herein, represents an acyl group derived from a carboxylic acid having 1-5 carbon atoms. The acyl group can comprise a hydrocarbon which may be branched, unbranched, saturated or unsaturated. Examples of such groups include formyl, acetyl, propanoyl, propenoyl and pivaloyl. Also included within the definition of $C_{1-5}$ acyl are groups derived from dicarboxylic acids like hemi-malanoyl.

The term halogen, as used herein, represents a fluorine, chlorine, bromine or iodine.

Examples of 5 to 7 membered unsaturated carbocyclic rings optionally comprising a N formed by $R^2$ together with $R^3$ include cyclopentenylene, cyclohexenylene, phenylene and pyridinylene.

Examples of 6 to 8 membered unsaturated carbocyclic rings optionally comprising a heteroatomic moiety selected from O and $NR^{11}$ formed by $R^5$ together with $R^6$ include cyclohexenylene and 1-methyl-1,2,5,6-tetrahydropyridinylene.

Examples of 3 to 5 membered saturated heterocyclic rings formed by $R^7$ and $R^8$ together with the nitrogen to which they are bonded include azetidine and pyrrolidine.

Examples of 5 or 6 membered heteroaryl comprising 1 or 2 heteroatoms selected from O, N and S include furanyl, thienyl, thiazolyl and pyridinyl.

Examples of $C_{3-8}$cycloalkyl comprising a heteroatomic moiety selected from O, S, $SO_2$ and $NR^{16}$, wherein $R^{16}$ has the previously defined meaning, include azetidinyl, pyrrolidinyl, piperidinyl and homopiperidinyl.

Examples of 5 or 6 membered saturated heterocyclic rings optionally comprising a heteroatomic moiety selected from O and $NR^{16}$, formed by $R^9$ and $R^{10}$ together with the nitrogen to which they are bonded include pyrrolidine, piperidine and piperazine.

Similarly examples of 5 or 6 membered saturated heterocyclic rings optionally comprising a heteroatomic moiety selected from O and $NR^{19}$, formed by $R^{12}$ and $R^{13}$ together with the nitrogen to which they are bonded include pyrrolidine, piperidine and piperazine.

In one embodiment $R^1$ is isopropyl, tertiary butyl, CN or trifluoromethyl. In a further embodiment $R^1$ is trifluoromethyl.

In another embodiment $R^2$ is methyl optionally substituted with hydroxy, $C_{1-4}$alkyloxy or $NR^7R^8$, wherein $R^7$ and $R^8$ have the previously defined meanings. In a further embodiment $R^2$ is hydroxymethyl or $CH_2NR^7R^8$.

In a further embodiment $R^2$ together with $R^3$ form a cyclohexenylene or cycloheptenylene ring.

In another embodiment $R^4$ is $CONR^9R^{10}$, wherein $R^9$ and $R^{10}$ have the previously defined meanings.

In another embodiment $R^5$ and $R^6$ are independently H or $C_{1-4}$alkyl. In a further embodiment $R^5$ and $R^6$ are independently H, methyl or ethyl. In a further embodiment $R^5$ together with $R^6$ form a 5, 6 or 7 membered unsaturated carbocyclic ring optionally comprising an O.

In another embodiment $R^7$ and $R^8$ are independently H, $C_{1-4}$alkyl or $C_{3-6}$cycloalkyl.

In another embodiment $R^9$ is H or $C_{1-4}$alkyl optionally substituted with hydroxy, $C_{1-6}$alkyloxy or $NR^{12}R^{13}$, wherein $R^{12}$ and $R^{13}$ have the previously defined meanings. In a further embodiment $R^9$ is $C_{1-4}$alkyl optionally substituted with Y, wherein Y is $C_{4-6}$cycloalkyl comprising 1-2 heteroatomic moieties selected from O and $NR^{16}$, wherein $R^{16}$ has the previously defined meaning.

In another embodiment $R^{10}$ is H or $C_{1-4}$alkyl. In a further embodiment $R^{10}$ is H or methyl.

In another embodiment $R^{11}$ is H or methyl.

In another embodiment is a heterocyclic derivative selected from

2-[2-(3-Trifluoromethyl-4,5,6,7-tetrahydroindazol-1-yl)-acetylamino]-4,5,6,7-tetrahydrobenzo[b]thiophene-3-carboxylic acid (3-hydroxy-propyl)-amide;

2-[2-(3-Trifluoromethyl-4,5,6,7-tetrahydroindazol-1-yl)-acetylamino]-4,5,6,7-tetrahydrobenzo[b]thiophene-3-carboxylic acid (2-methanesulfonylamino-ethyl)-amide;

2-[2-(3-Trifluoromethyl-4,5,6,7-tetrahydroindazol-1-yl)-acetylamino]-4,5,6,7-tetrahydrobenzo[b]thiophene-3-carboxylic acid azetidin-3-ylamide;

2-(2-(3-(trifluoromethyl)-4,5-dihydroindazole-1-yl)acetamido-4,5,6,7-tetrahydrothieno[2,3-c]pyran-3-carboxamide;

2-[2-(4-ethylaminomethyl-3-trifluoromethylpyrazol-1-yl)-acetylamino]-4,5,6,7-tetrahydrobenzo[b]thiophene-3-carboxamide;

2-(2-(4-hydroxymethyl)-3-(trifluoromethyl)pyrazol-1-yl)acetamido)-4,5,6,7-tetrahydrobenzo[b]thiophene-3-carboxamide;

2-{2-[4-(1-Hydroxy-ethyl)-3-trifluoromethylpyrazol-1-yl]-acetylamino}-4,5,6,7-tetrahydro-benzo[b]thiophene-3-carboxamide and 2-[2-(3-tert-Butyl-4-dimethylaminomethylpyrazol-1-yl)-acetylamino]-4,5,6,7-tetrahydrobenzo[b]thiophene-3-carboxamide N-(2-hydroxyethyl)-2-(2-(4-((methylamino)methyl)-3-(trifluoromethyl)-H-pyrazol-1-yl)acetamido)-4,5,6,7-tetrahydrobenzo[b]thiophene-3-carboxamide or a pharmaceutically acceptable salt or solvate thereof.

The heterocyclic derivatives of the present invention are prepared by methods well known in the art of organic chemistry. See, for example, J. March, 'Advanced Organic Chemistry' $4^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' $2^{nd}$ Edition, John Wiley and Sons, 1991. The protective groups are optionally removed at a convenient subsequent stage using methods well known in the art.

The synthesis of heterocyclic derivatives of the general formula (I) may be accomplished as outlined in Schemes 1-6 below.

Heterocyclic derivatives such as (8) are prepared as shown in Scheme 1. Alkylation of pyrazole derivative (1) using a base such as NaH or potassium carbonate in N,N-dimethylformamide (DMF) provides the acetate derivative (2). Subsequent removal of the t-butyl group with acid, for example, using trifluoroacetic acid (TFA) provides the acid derivative (3). Coupling of the acid derivative (3) with an aminothiophene derivative (4) using, for example, O-(7-Azabenzotriazole-1-yl)-N,N,N',N'-tetramethyluronium hexafluorophosphate (HATU) in the presence of an organic base such as diisopropylethylamine (DIEA) gives the amide (5). Removal of the t-butyl ester with an acid such as TFA or HCl and subsequent treatment of the resulting carboxylic acid intermediate (6) with an amine together with a coupling reagent such as HATU in the presence of an organic base such as DEA provides the amide derivative (7). Finally deprotection of the Boc group with an acid such as TFA or HCl gives the alkylamide (8).

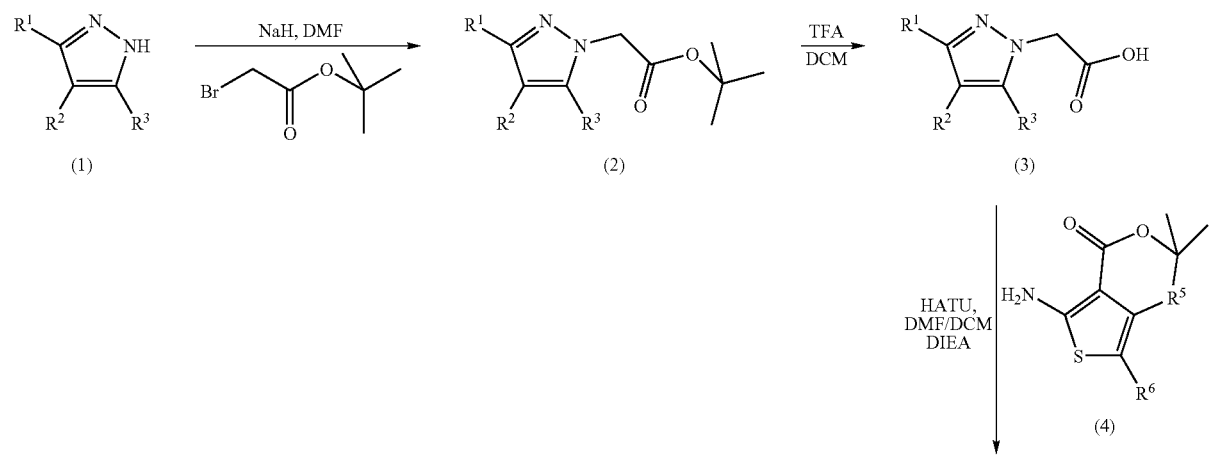

Scheme 1.

-continued

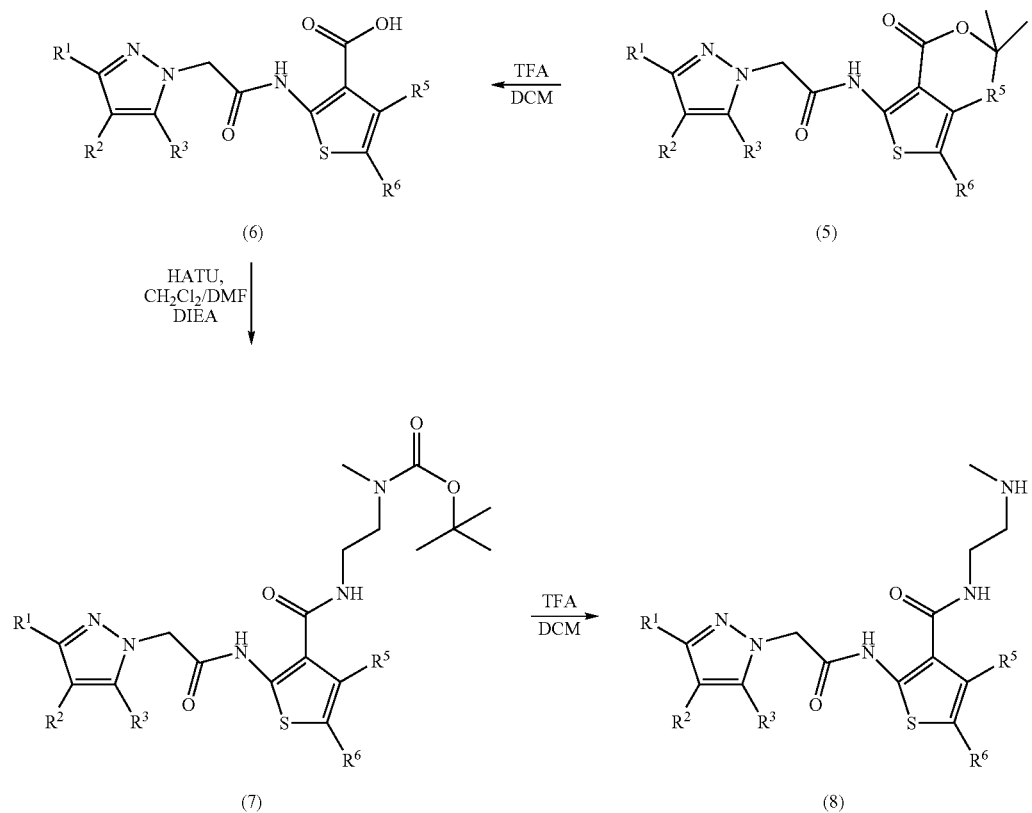

Pyrazole derivatives (1) and aminothiophene derivatives (4), are obtained from commercial sources, or are prepared by literature procedures or modifications of literature procedures known to persons skilled in the art. For example, as adumbrated in Scheme 2, aminothiophene derivatives (4) are prepared by the condensation of t-butylcyanoacetate, cyclohexanone and sulfur in the presence of an organic base such as diethylamine or N-methylmorpholine.

Scheme 2.

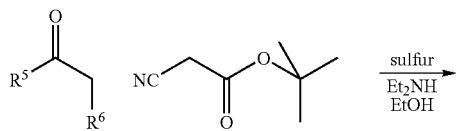

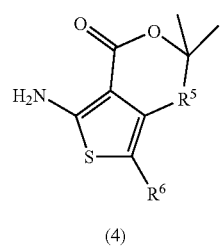

An alternative construction of the indazole amide system is delineated in Scheme 3. Treatment of the aminothiophene derivative (9) with a suitable acid halide in, for example, DCM and in the presence of triethylamine, provides the halogenated amide derivatives (10). Further reaction of amides (10) with a pyrazole derivative (11) in the presence of a base, such as, potassium carbonate or NaH gives the adducts (12). Similarly, bromoacetamide (10) is elaborated to give the amide adducts (15). Reductive amination of (12), using, for example, triacetoxyborohydride and acetic acid in MeOH, gives the (13). Alternatively, reduction of (12) using, for example, sodium borohydride in MeOH, gives the amides (14).

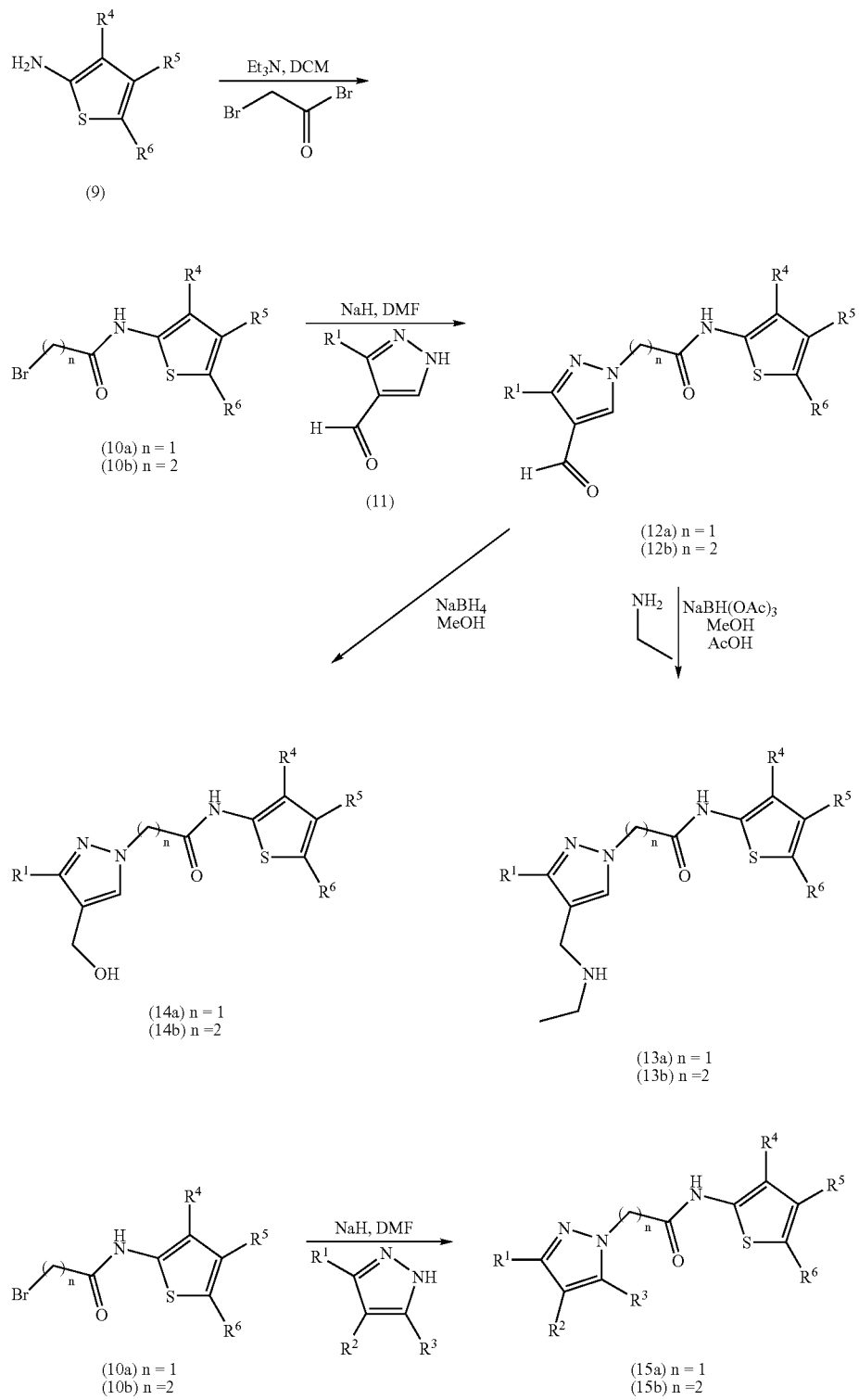

Scheme 3.

Amine derivatives of the type (13a) are also be prepared as illustrated in Scheme 4. Alkylation of 3-(trifluoromethyl)-4-cyanopyrazole (16) with bromoacetamide derivative (10) using a base, such as NaH, provides (17). Reduction of (17) with sodium borohydride in the presence of a cobalt salt furnishes the amine (18). Subsequent reductive amination using, for example, acetone in the presence of sodium triacetoxyborohydride in DCM provides the amine (19).

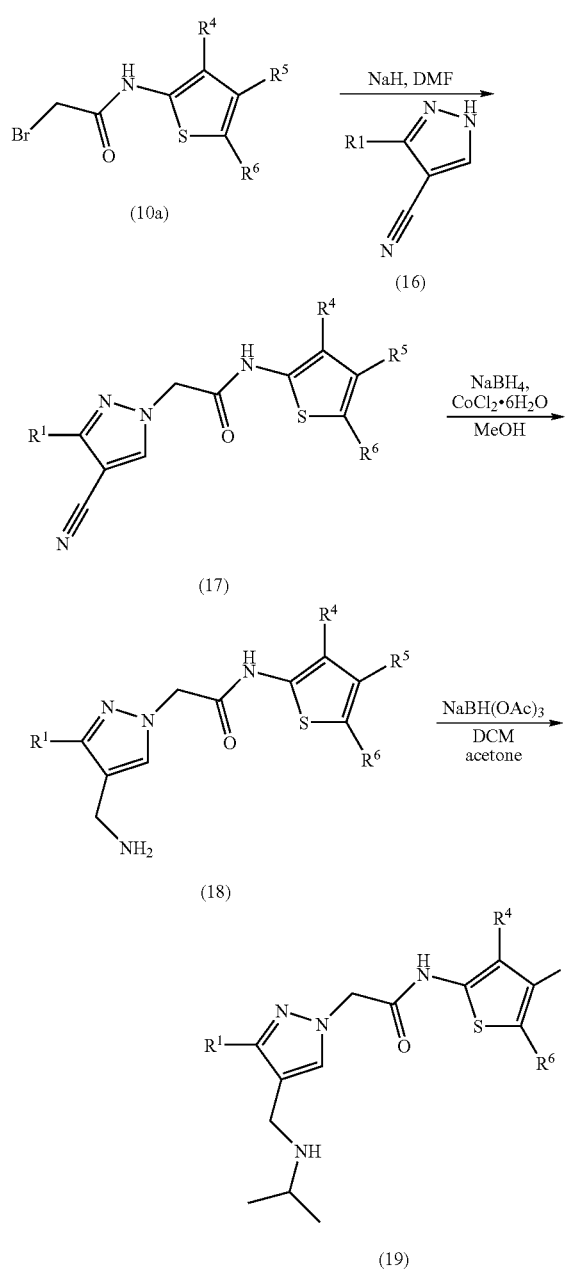

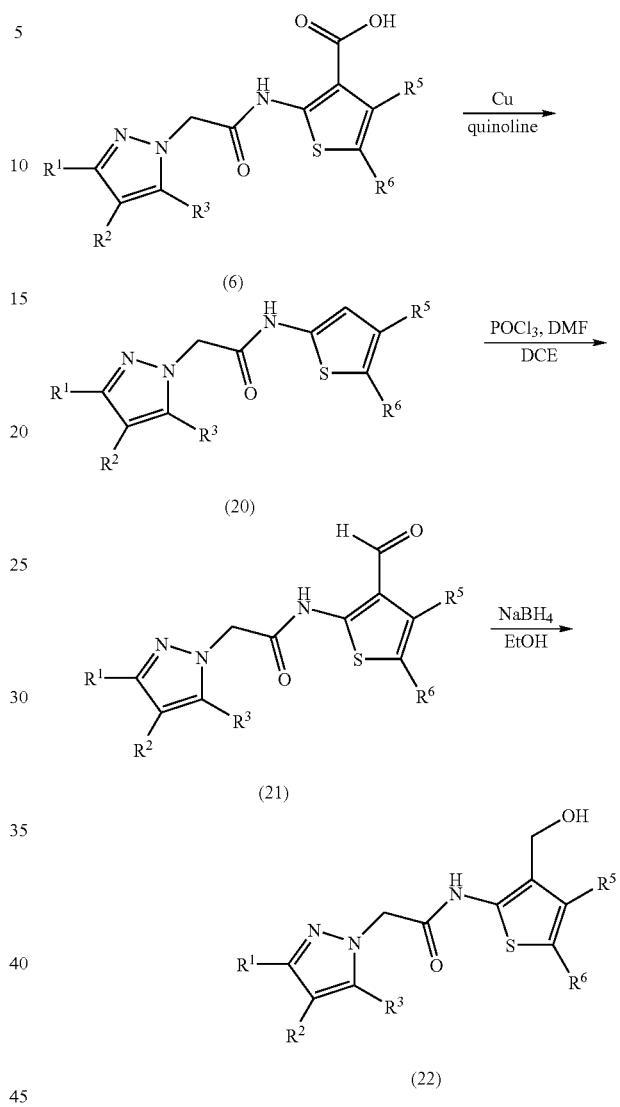

the aldehyde (21). The alcohol (22) results following reduction of (21) with, for example, sodium borohydride in EtOH.

As shown in Scheme 5, the acid derivative (6) is decarboxylated upon heating with copper in quinoline. The thiophene (20) is then carbonylated using, for example, phosphorus oxychloride and DMF in dichloroethane to provide Aldehyde derivatives of the type (11) may be prepared as illustrated in Scheme 6. Formation of the pinacol semicarbazone (25) using semicarbazide (24), followed by treatment with phosphorus oxychloride in DMF provides aldehyde (11). Alternatively, reduction of esters of the type (26) with reagents such as lithium aluminium hydride to give alcohol (27) followed by oxidation with manganese dioxide or similar reagent provides aldehyde (11).

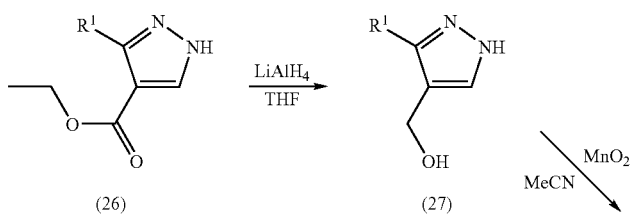

-continued

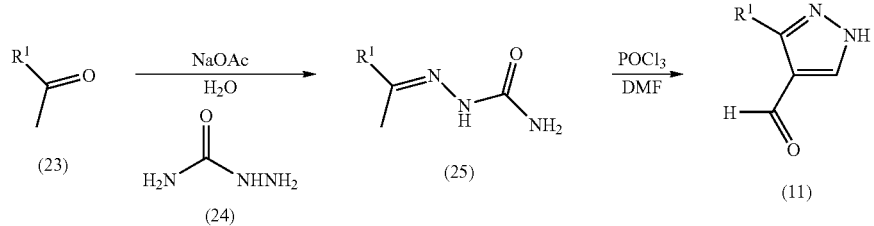

Heterocyclic derivatives such as (34) are prepared as shown in Scheme 7. Displacement of the ester can be achieved using, for example, ethanolamine at reflux. The cyanoactamide obtained (29) can be condensed with, for example, cyclohexanone under dehydrating conditions to give (30). Cyclisation with sulfur in the presence of an organic base such as diethylamine or N-methylmorpholine gives the aminothiophene derivative (31). Treatment of the aminothiophene derivative (31) with bromoacetyl bromide in, for example, THF and in the presence of diisopropylethylamine, provides the bromoacetamide derivative (32). Further reaction of bromoacetamide (32) with a pyrazole derivative (11) in the presence of a base, such as potassium carbonate, gives adduct (33). Reductive amination of the aldehyde (33), using, for example, triacetoxyborohydride and acetic acid in MeOH or palladium on carbon, hydrogen and acetic acid in DCM gives the amine (34).

Scheme 7

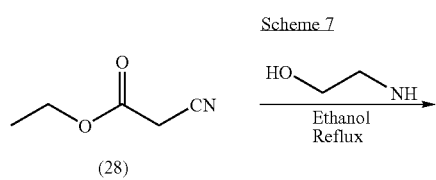

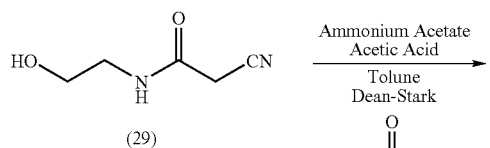

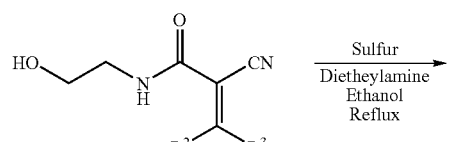

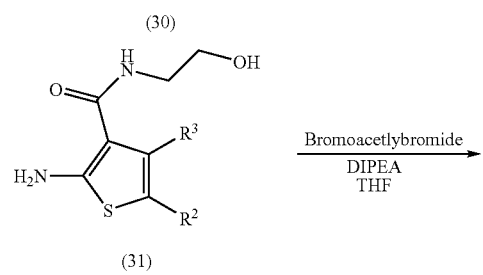

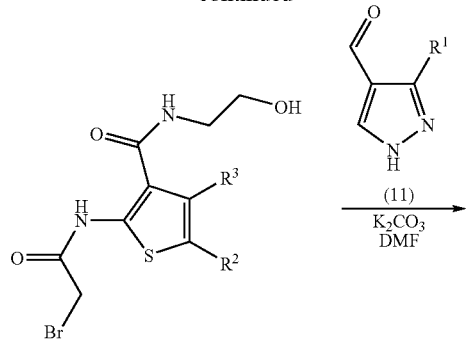

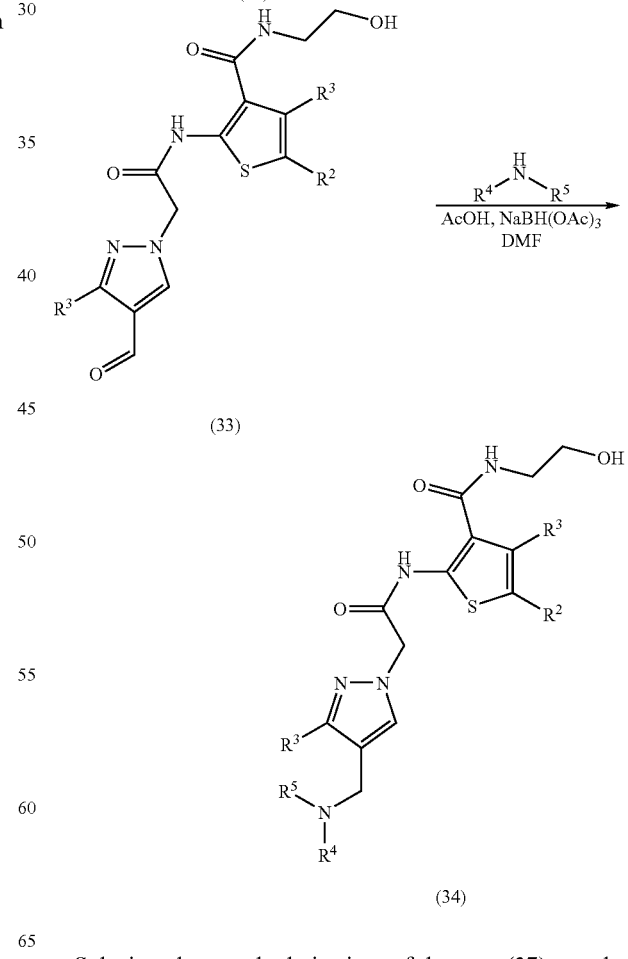

Substituted pyrazole derivatives of the type (37) may be prepared as illustrated in Scheme 8. Treatment of the aldehyde (12a) with a suitable Grignard reagent followed by oxidation using, for example, the Dess-Martin periodinane reagent gives intermediate ketone (36). Reductive amination using sodium cyanoborohydride furnishes amine (37).

Scheme 8

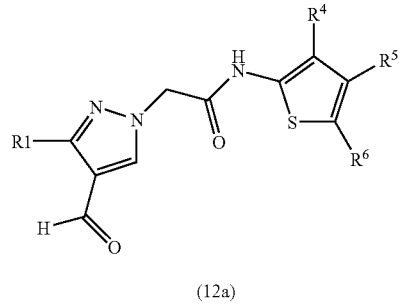
(12a)

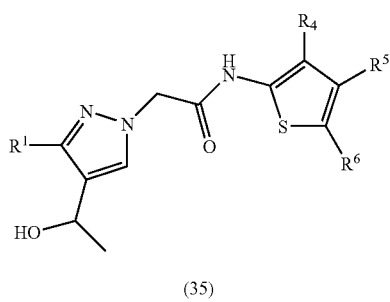
(35)

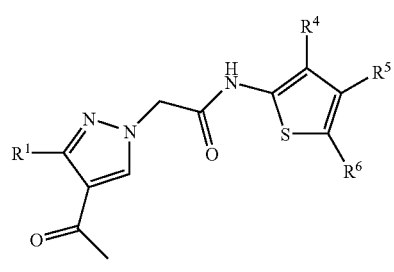
(36)

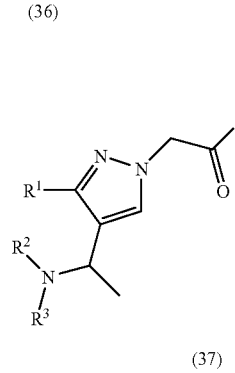
(37)

Pyrazolyl amine derivatives of the type (41) can be prepared as delineated in Scheme 9. Treatment of bromacetamide derivative (10a) with a pyrazole alcohol (38) in the presence of a suitable base provides intermediate (39). Conversion of the alcohol into a suitable leaving group followed by displacement with an amine furnishes the desired alkyl amine derivative (41).

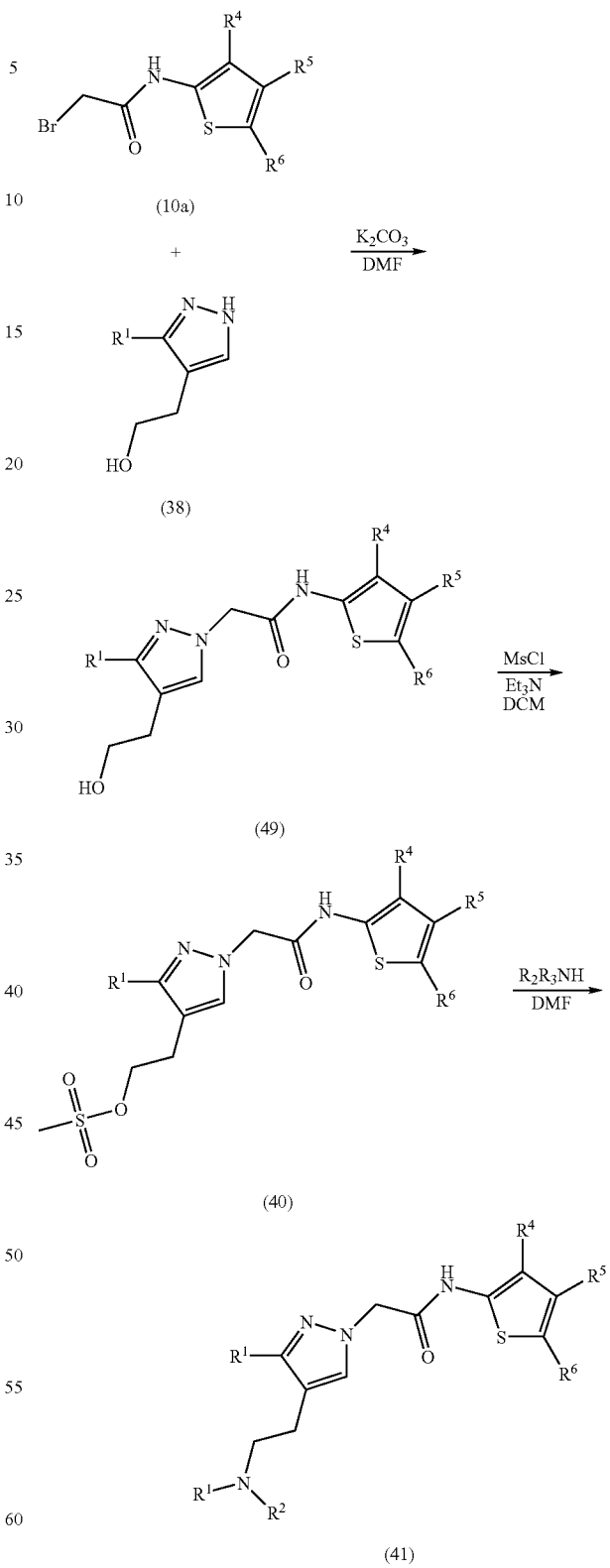

The present invention also includes within its scope all stereoisomeric forms of heterocyclic derivatives according to the present invention resulting, for example, because of configurational or geometrical isomerism. Such stereoisomeric forms are enantiomers, diastereoisomers, cis and trans isomers etc. For example, in the case where R¹ is 1-hydroxyethyl the compound exists as a pair of enantiomers. In the case where R⁵ is 2-methyl-1-cyclopentyl, both cis and trans geometric isomers are possible. In the case of the individual stereoisomers of heterocyclic derivatives of formula I or salts or solvates thereof, the present invention includes the aforementioned stereoisomers substantially free, i.e., associated with less than 5%, preferably less than 2% and in particular less than 1% of the other stereoisomer. Mixtures of stereoisomers in any proportion, for example a racemic mixture comprising substantially equal amounts of two enantiomers are also included within the scope of the present invention.

For chiral compounds, methods for asymmetric synthesis whereby the pure stereoisomers are obtained are well known in the art, e.g., synthesis with chiral induction, synthesis starting from chiral intermediates, enantioselective enzymatic conversions, separation of stereoisomers using chromatography on chiral media. Such methods are described in *Chirality In Industry* (edited by A. N. Collins, G. N. Sheldrake and J. Crosby, 1992; John Wiley). Likewise methods for synthesis of geometrical isomers are also well known in the art.

The heterocyclic derivatives of the present invention, in the form as a free base, are isolated from reaction mixtures as pharmaceutically acceptable salts. These salts are also obtained by treatment of said free base with an organic or inorganic acid, for example, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulfonic acid, fumaric acid, succinic acid, tartaric acid, citric acid, benzoic acid and ascorbic acid.

The heterocyclic derivatives of the present invention exist in both solvated and unsolvated forms, including hydrated forms. These forms are also encompassed within the scope of the present invention.

The heterocyclic derivatives of the present invention also exist as amorphous forms. Multiple crystalline forms are also possible. All these physical forms are included within the scope of the present invention.

In a further aspect, the heterocyclic derivatives of the present invention and their pharmaceutically acceptable salts and solvates are useful in therapy. As such the heterocyclic derivatives of the present invention are useful for the manufacture of a medicament for the treatment or prevention of psychiatric diseases where an enhancement of synaptic responses mediated by AMPA receptors is required. In particular the heterocyclic derivatives are useful for the manufacture of a medicament for the treatment of neurodegenerative disorders, cognitive or memory dysfunction, memory and learning disorders, attention disorder, trauma, stroke, epilepsy, Alzheimer's disease, depression, schizophrenia, psychotic disorders, anxiety, autism, a disorder or disease resulting from neurotic agents, substance abuse, alcohol psychiatric disorders, Parkinson's Disease, sleep disorders or narcolepsy or other conditions resulting from sleep deprivation. The present invention further includes a heterocyclic derivative for use in the treatment of any of the aforementioned diseases or disorders.

The present invention further includes a method for the treatment of a mammal, including a human, suffering from or liable to suffer from depression or any of the aforementioned disorders, which comprises administering an effective amount of a heterocyclic derivative according to the present invention or a pharmaceutically acceptable salt or solvate thereof.

The amount of a heterocyclic derivative of the present invention or a pharmaceutically acceptable salt or solvate thereof, also referred to herein as the active ingredient, which is required to achieve a therapeutic effect will, of course, vary with the particular compound, the route of administration, the age and condition of the recipient and the particular disorder or disease being treated.

A suitable daily dose for any of the above mentioned disorders will be in the range of 0.001 to 50 mg per kilogram body weight of the recipient (e.g. a human) per day, preferably in the range of 0.01 to 20 mg per kilogram body weight per day. The desired dose may be presented as multiple sub-doses administered at appropriate intervals throughout the day.

Whilst it is possible for the active ingredient to be administered alone, it is preferable to present it as a pharmaceutical composition. The present invention therefore also provides a pharmaceutical composition comprising a heterocyclic derivative according to the present invention in admixture with one or more pharmaceutically acceptable excipients, such as the ones described in Gennaro et. al., Remmington: *The Science and Practice of Pharmacy*, 20$^{th}$ Edition, Lippincott, Williams and Wilkins, 2000; see especially part 5: pharmaceutical manufacturing. Suitable excipients are described e.g., in the Handbook of Pharmaceutical Excipients, 2$^{nd}$ Edition; Editors A. Wade and P. J. Weller, American Pharmaceutical Association, Washington, The Pharmaceutical Press, London, 1994. Compositions include those suitable for oral, nasal, topical (including buccal, sublingual and transdermal), parenteral (including subcutaneous, intravenous and intramuscular) or rectal administration.

The mixtures of a heterocyclic derivative according to the present invention and one or more pharmaceutically acceptable excipient or excipients may be compressed into solid dosage units, such as tablets, or be processed into capsules or suppositories. By means of pharmaceutically suitable liquids the compounds can also be applied as an injection preparation in the form of a solution, suspension, emulsion, or as a spray, e.g., a nasal or buccal spray. For making dosage units e.g., tablets, the use of conventional additives such as fillers, colorants, polymeric binders and the like is contemplated. In general, any pharmaceutically acceptable additive can be used. The compounds of the invention are also suitable for use in an implant, a patch, a gel or any other preparation for immediate and/or sustained release.

Suitable fillers with which the pharmaceutical compositions can be prepared and administered include lactose, starch, cellulose and derivatives thereof, and the like, or mixtures thereof used in suitable amounts.

The invention is further illustrated by the following examples.

EXAMPLE 1

2-[2-(3-Trifluoromethyl-4,5,6,7-tetrahydroindazol-1-yl)-acetylamino]-4,5,6,7-tetrahydrobenzo[b]thiophene-3-carboxylic acid (2-dimethylaminoethyl)-amide a) (3-Trifluoromethyl-4,5,6,7-tetrahydroindazol-1-yl)-acetic acid

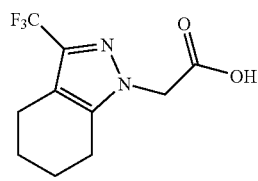

Sodium hydride (60% [w/w] dispersion in mineral oil, 632 mg, 15.8 mmol) was added portionwise to a stirred solution of 4,5,6,7-tetrahydro-3-(trifluoromethyl)-indazole (3.00 g, 15.8 mmol) in DMF (60 mL), and the mixture stirred at RT for 30 min. Tert-butyl bromoacetate (2.33 mL, 15.8 mmol) was added and the reaction mixture stirred at 80° C. for 2 h, and allowed to cool to RT. Water (50 mL) was added and the resulting solution extracted with EtOAc (3×200 mL), washed with water (200 mL), brine (200 mL), dried over sodium sulfate, and concentrated in vacuo to afford (3-Trifluoromethyl-4,5,6,7-tetrahydro-indazol-1-yl)-acetic acid tert-butyl ester.

(3-Trifluoromethyl-4,5,6,7-tetrahydroindazol-1-yl)-acetic acid tert-butyl ester was dissolved in a solution of DCM (30 mL) and TFA (30 mL), and the resulting mixture stirred at RT for 30 min, before concentration in vacuo to afford the title compound (4.50 g). This was used directly in the next step without any further purification.

b) 2-Amino-4,5,6,7-tetrahydro-benzo[b]thiophene-3-carboxylic acid tert-butyl ester

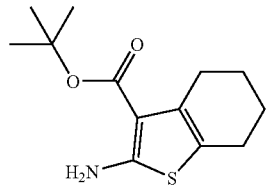

Cyclohexanone (2.0 g, 20.4 mmol), tert-butyl cyanoacetate (2.88 g, 20.4 mmol), sulphur (650 mg, 20.4 mmol) were stirred in EtOH (8 mL). Diethylamine (2.5 mL, 24.2 mmol) was added and the reaction mixture stirred at RT overnight. Water (30 mL) was added and the reaction mixture extracted with EtOAc (3×30 mL). The combined EtOAc layers were washed with brine, dried over MgSO$_4$, filtered and the solvent removed in vacuo to give desired product as a gum (5.5 g). The compound was used directly without any further purification.

MS (ESI): m/z 254 [M+H]+ c) 2-[2-(3-Trifluoromethyl-4,5,6,7-tetrahydroindazol-1-yl)-acetylamino]-4,5,6,7-tetrahydro-benzo[b]thiophene-3-carboxylic acid tert-butyl ester

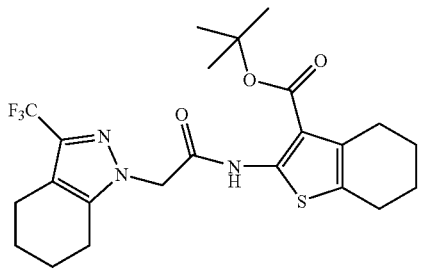

(3-Trifluoromethyl-4,5,6,7-tetrahydroindazol-1-yl)-acetic acid (638 mg, 2.57 mmol) was suspended in a solution of DCM (10 mL) and DMF (1 mL) and O-(7-azabenzotriazol-1-yl)-N,N,N',N'-tetramethyluronium hexafluorophosphate (1.17 g, 3.08 mmol) and N,N'-diisopropylethylamine (537 μL, 3.08 mmol) added, followed by 2-Amino-4,5,6,7-tetrahydro-benzo[b]thiophene-3-carboxylic acid tert-butyl ester (651 mg, 2.57 mmol). The resultant mixture was stirred at RT overnight. The solution was concentrated in vacuo. The residue was purified by silica gel chromatography using DCM as eluent, to afford the title compound as a yellow solid (0.93 g, 1.93 mmol, 75%).

d) 2-[2-(3-Trifluoromethyl-4,5,6,7-tetrahydroindazol-1-yl)-acetylamino]-4,5,6,7-tetrahydro-benzo[b]thiophene-3-carboxylic acid

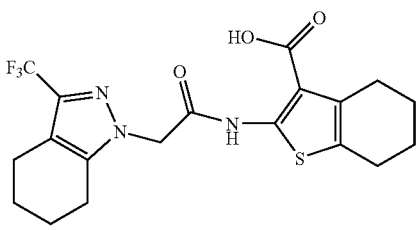

2-[2-(3-Trifluoromethyl-4,5,6,7-tetrahydroindazol-1-yl)-acetylamino]-4,5,6,7-tetrahydrobenzo[b]thiophene-3-carboxylic acid tert-butyl ester was dissolved in a solution of DCM (5 mL) and TFA (5 mL), and the resulting mixture stirred at RT for 3 h, before concentration in vacuo to afford the title compound as a pale yellow solid (870 mg). This was used directly in the next step without any further purification.

e) 2-[2-(3-Trifluoromethyl-4,5,6,7-tetrahydroindazol-1-yl)-acetylamino]-4,5,6,7-tetrahydro-benzo[b]thiophene-3-carboxylic acid (2-dimethylamino-ethyl)-amide

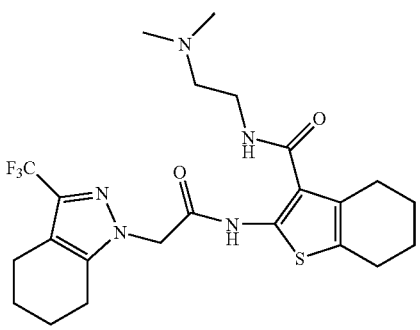

2-[2-(3-Trifluoromethyl-4,5,6,7-tetrahydroindazol-1-yl)-acetylamino]-4,5,6,7-tetrahydrobenzo[b]thiophene-3-carboxylic acid (50 mg, 0.117 mmol) was dissolved in a solution of DCM (2 mL) and DMF (0.4 mL). O-(7-azabenzotriazol-1-yl)-N,N',N',N'-tetramethyluronium hexafluorophosphate (54 mg, 0.141 mmol) was added, followed by N,N-dimethylethylenediamine (15.5 μL, 0.141 mmol) and N,N-diisopropylethylamine (24.6 μL, 0.141 mmol). The resultant mixture was stirred at RT overnight. The solvent was removed under reduced pressure, and the residue obtained purified by preparative reverse phase HPLC, to afford the title compound, a colourless oil, as the TFA salt (52 mg, 0.084 mmol, 72%).

MS (ESI): m/z 498.5 [M+H]+.

EXAMPLE 2

2-[2-(3-Trifluoromethyl-4,5,6,7-tetrahydroindazol-1-yl)-acetylamino]-4,5,6,7-tetrahydrobenzo[b]thiophene-3-carboxylic acid (2-piperidin-1-yl-ethyl)-amide

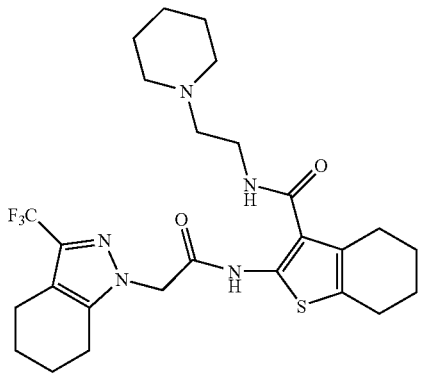

In a similar manner to example 1e, 1-(2-aminoethyl)-piperidine was used in place of N,N-dimethylethylenediamine to yield the title compound, an orange/brown residue, as the TFA salt (7 mg, 0.0111 mmol, 9%).

MS (ESI): m/z 538.7 [M+H]$^+$.

EXAMPLE 3

2-[2-(3-Trifluoromethyl-4,5,6,7-tetrahydroindazol-1-yl)-acetylamino]-4,5,6,7-tetrahydrobenzo[b]thiophene-3-carboxylic acid (2-hydroxy-1,1-dimethyl-ethyl)-amide

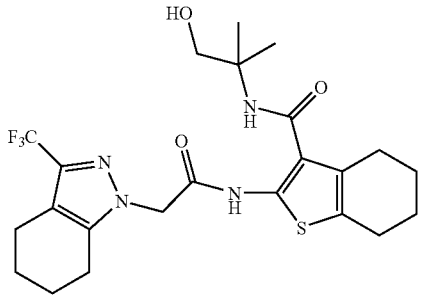

In a similar manner to example 1e, 2-amino-2-methyl-1-propanol was used in place of N,N-dimethylethylenediamine to yield the title compound as a pale brown oil (13 mg, 0.026 mmol, 23%).

MS (ESI): m/z 499.3 [M+H]$^+$.

EXAMPLE 4

2-[2-(3-Trifluoromethyl-4,5,6,7-tetrahydroindazol-1-yl)-acetylamino]-4,5,6,7-tetrahydrobenzo[b]thiophene-3-carboxylic acid cyclopropylamide

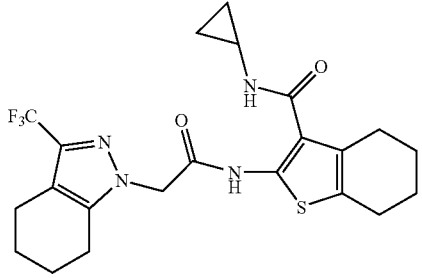

In a similar manner to example 1e, cyclopropylamine was used in place of N,N-dimethylethylenediamine to yield the title compound as a white solid (5 mg, 0.011 mmol, 10%).

MS (ESI): m/z 467.3 [M+H]$^+$.

EXAMPLE 5

2-[2-(3-Trifluoromethyl-4,5,6,7-tetrahydroindazol-1-yl)-acetylamino]-4,5,6,7-tetrahydrobenzo[b]thiophene-3-carboxylic acid (3-hydroxy-propyl)-amide

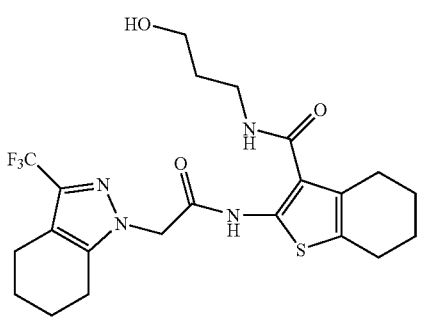

In a similar manner to example 1e, 3-amino-1-propanol was used in place of N,N-dimethylethylenediamine to yield the title compound (4 mg, 0.007 mmol, 12%).

MS (ESI): m/z 485.8 [M+H]$^+$.

EXAMPLE 6

2-[2-(3-Trifluoromethyl-4,5,6,7-tetrahydroindazol-1-yl)-acetylamino]-4,5,6,7-tetrahydrobenzo[b]thiophene-3-carboxylic acid (3-methoxy-propyl)-amide

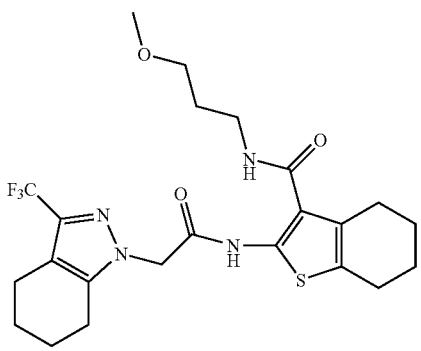

In a similar manner to example 1e, 3-methoxypropylamine was used in place of N,N-dimethylethylenediamine to yield the title compound (8 mg, 0.017 mmol, 29%).

MS (ESI): m/z 499.3 [M+H]$^+$.

EXAMPLE 7

2-[2-(3-Trifluoromethyl-4,5,6,7-tetrahydroindazol-1-yl)-acetylamino]-4,5,6,7-tetrahydrobenzo[b]thiophene-3-carboxylic acid (2,3-dihydroxy-propyl)-amide

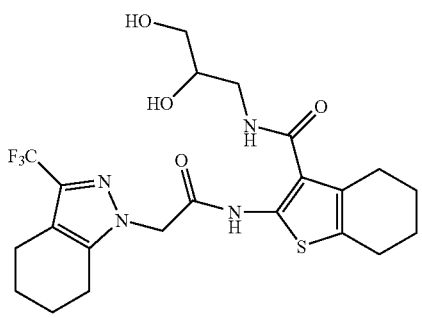

In a similar manner to example 1e, 3-amino-1,2-propanediol was used in place of N,N-dimethylethylenediamine to yield the title compound (9 mg, 0.018 mmol, 31%).
MS (ESI): m/z 501.3 [M+H]$^+$.

EXAMPLE 8

2-[2-(3-Trifluoromethyl-4,5,6,7-tetrahydroindazol-1-yl)-acetylamino]-4,5,6,7-tetrahydrobenzo[b]thiophene-3-carboxylic acid (3-imidazol-1-yl-propyl)-amide

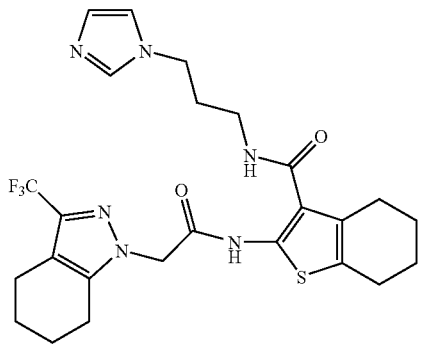

In a similar manner to example 1e, 1-(3-aminopropyl)imidazole was used in place of N,N-dimethylethylenediamine to yield the title compound (3 mg, 0.005 mmol, 9%).
MS (ESI): m/z 532.2 [M+H]$^+$.

EXAMPLE 9

2-[2-(3-Trifluoromethyl-4,5,6,7-tetrahydroindazol-1-yl)-acetylamino]-4,5,6,7-tetrahydrobenzo[b]thiophene-3-carboxylic acid propylamide

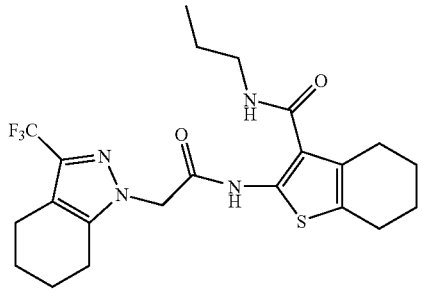

In a similar manner, propylamine was used in place of N,N-dimethylethylenediamine to yield the title compound (2 mg, 0.004 mmol, 7%).
MS (ESI): m/z 469.3 [M+H]$^+$.

EXAMPLE 10

2-[2-(3-Trifluoromethyl-4,5,6,7-tetrahydroindazol-1-yl)-acetylamino]-4,5,6,7-tetrahydrobenzo[b]thiophene-3-carboxylic acid (pyridin-3-ylmethyl)-amide

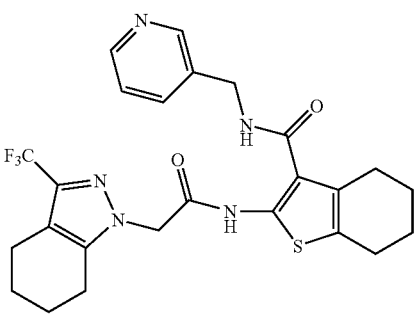

In a similar manner to example 1e, 3-(aminomethyl)pyridine was used in place of N,N-dimethylethylenediamine to yield the title compound (7 mg, 0.011 mmol, 18%).
MS (ESI): m/z 518.3 [M+H]$^+$.

EXAMPLE 11

2-[2-(3-Trifluoromethyl-4,5,6,7-tetrahydroindazol-1-yl)-acetylamino]-4,5,6,7-tetrahydrobenzo[b]thiophene-3-carboxylic acid [2-(4-methyl-piperazin-1-yl)-2-oxo-ethyl]-amide

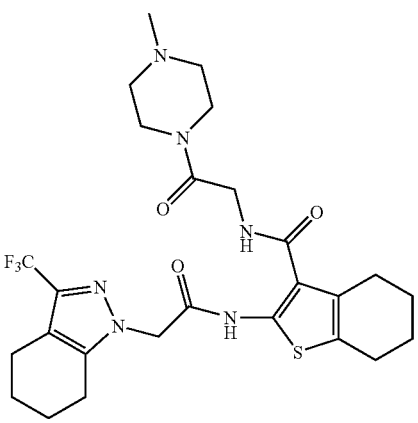

In a similar manner to example 1e, 2-amino-1-(4-methylpiperazinyl)ethanone.2HCl was used in place of N,N-dimethylethylenediamine to yield the title compound (7 mg, 0.012 mmol, 17%).
MS (ESI): m/z 567.5 [M+H]$^+$.

EXAMPLE 12

2-[2-(3-Trifluoromethyl-4,5,6,7-tetrahydroindazol-1-yl)-acetylamino]-4,5,6,7-tetrahydrobenzo[b]thiophene-3-carboxylic acid methylcarbamoylmethyl-amide

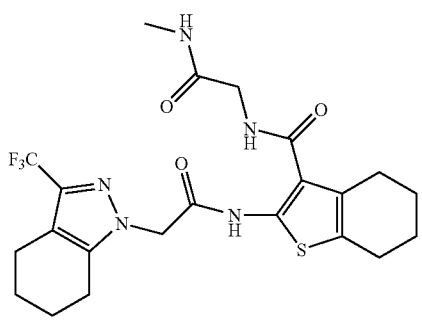

In a similar manner to example 1e, 2-Amino-N-methyl-acetamide.HCl was used in place of N,N-dimethylethylenediamine to yield the title compound (11 mg, 0.022 mmol, 31%).

MS (ESI): m/z 498.6 [M+H]$^+$.

EXAMPLE 13

2-[2-(3-Trifluoromethyl-4,5,6,7-tetrahydroindazol-1-yl)-acetylamino]-4,5,6,7-tetrahydrobenzo[b]thiophene-3-carboxylic acid [2-(2-oxo-imidazolidin-1-yl)-ethyl]-amide

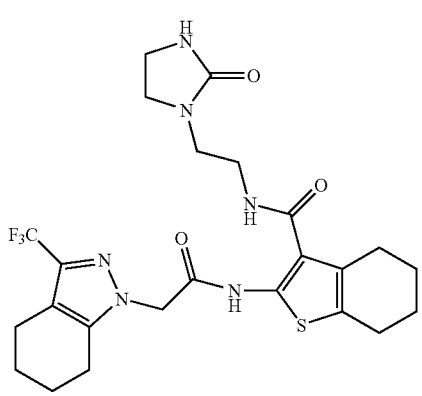

In a similar manner to example 1e, 1-(2-aminoethyl)imidazolin-2-one was used in place of N,N-dimethylethylenediamine to yield the title compound (4 mg, 0.008 mmol, 11%).

MS (ESI): m/z 539.7 [M+H]$^+$.

EXAMPLE 14

2-[2-(3-Trifluoromethyl-4,5,6,7-tetrahydroindazol-1-yl)-acetylamino]-4,5,6,7-tetrahydrobenzo[b]thiophene-3-carboxylic acid (2-thiomorpholin-4-yl-ethyl)-amide

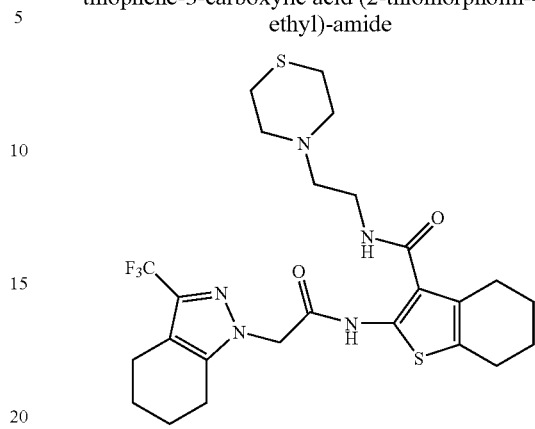

In a similar manner to example 1e, 1-(2-aminoethyl)thiomorpholine was used in place of N,N-dimethylethylenediamine to yield the title compound (13 mg, 0.024 mmol, 34%).

MS (ESI): m/z 556.3 [M+H]$^+$.

EXAMPLE 15

2-[2-(3-Trifluoromethyl-4,5,6,7-tetrahydroindazol-1-yl)-acetylamino]-4,5,6,7-tetrahydrobenzo[b]thiophene-3-carboxylic acid (1-ethyl-pyrrolidin-2-ylmethyl)-amide

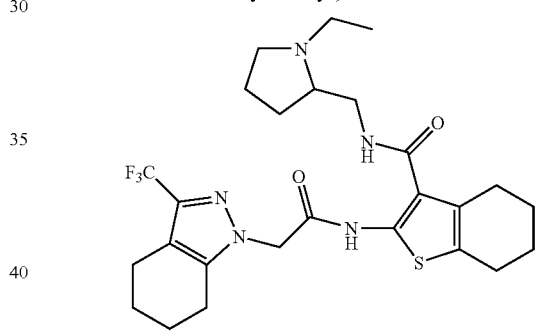

In a similar manner to example 1e, 1-(2-aminomethyl)-1-ethyl-pyrrolidine was used in place of N,N-dimethylethylenediamine to yield the title compound as a TFA salt (13 mg, 0.020 mmol, 29%).

MS (ESI): m/z 538.5 [M+H]$^+$.

EXAMPLE 16

2-[2-(3-Trifluoromethyl-4,5,6,7-tetrahydroindazol-1-yl)-acetylamino]-4,5,6,7-tetrahydrobenzo[b]thiophene-3-carboxylic acid (2-pyrrolidin-1-yl-ethyl)-amide

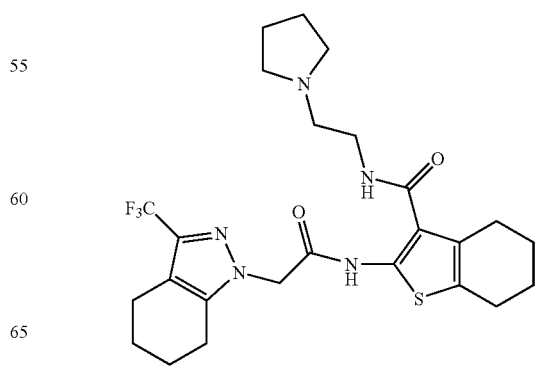

In a similar manner to example 1e, N-(2-aminoethyl)pyrrolidine was used in place of N,N-dimethylethylenediamine to yield the title compound as a TFA salt (8 mg, 0.013 mmol, 18%).

MS (ESI): m/z 524.5 [M+H]$^+$.

EXAMPLE 17

2-[2-(3-Trifluoromethyl-4,5,6,7-tetrahydroindazol-1-yl)-acetylamino]-4,5,6,7-tetrahydrobenzo[b]thiophene-3-carboxylic acid (2-morpholin-4-yl-ethyl)-amide

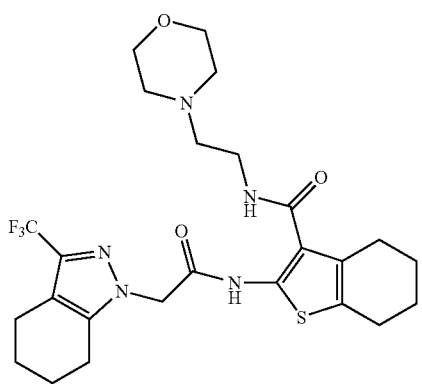

In a similar manner to example 1e, N-(2-aminoethyl)morpholine was used in place of N,N-dimethylethylenediamine to yield the title compound (15 mg, 0.023 mmol, 33%).

MS (ESI): m/z 540.5 [M+H]$^+$.

EXAMPLE 18

2-[2-(3-Trifluoromethyl-4,5,6,7-tetrahydroindazol-1-yl)-acetylamino]-4,5,6,7-tetrahydrobenzo[b]thiophene-3-carboxylic acid (3-morpholin-4-yl-propyl)-amide

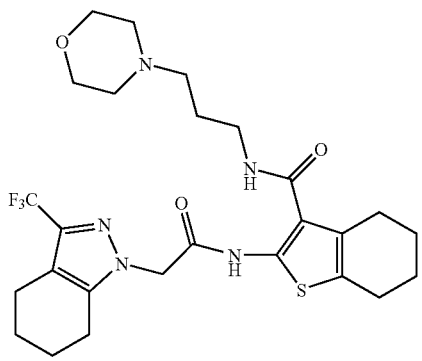

In a similar manner to example 1e, N-(3-aminopropyl)morpholine was used in place of N,N-dimethylethylenediamine to yield the title compound (9 mg, 0.014 mmol, 20%).

MS (ESI): m/z 554.3 [M+H]$^+$.

EXAMPLE 19

2-[2-(3-Trifluoromethyl-4,5,6,7-tetrahydroindazol-1-yl)-acetylamino]-4,5,6,7-tetrahydrobenzo[b]thiophene-3-carboxylic acid (pyridin-2-ylmethyl)-amide

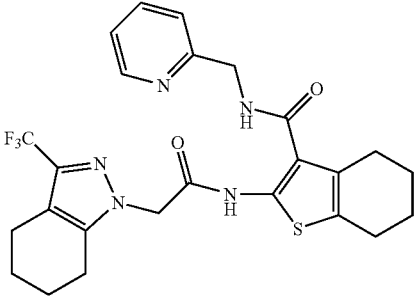

In a similar manner to example 1e, 2-(aminomethyl)pyridine was used in place of N,N-dimethylethylenediamine to yield the title compound (5 mg, 0.009 mmol, 14%).

MS (ESI): m/z 518.3 [M+H]$^+$.

EXAMPLE 20

2-[2-(3-Trifluoromethyl-4,5,6,7-tetrahydroindazol-1-yl)-acetylamino]-4,5,6,7-tetrahydrobenzo[b]thiophene-3-carboxylic acid (2-pyridin-2-yl-ethyl)-amide

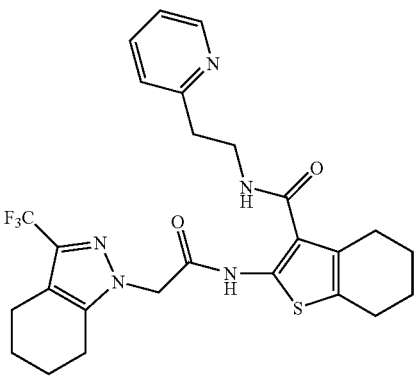

In a similar manner to example 1e, 2-(2-aminoethyl)pyridine was used in place of N,N-dimethylethylenediamine to yield the title compound (6 mg, 0.012 mmol, 17%).

MS (ESI): m/z 532.3 [M+H]$^+$.

EXAMPLE 21

2-[2-(3-Trifluoromethyl-4,5,6,7-tetrahydroindazol-1-yl)-acetylamino]-4,5,6,7-tetrahydrobenzo[b]thiophene-3-carboxylic acid (2-hydroxy-ethyl)-amide

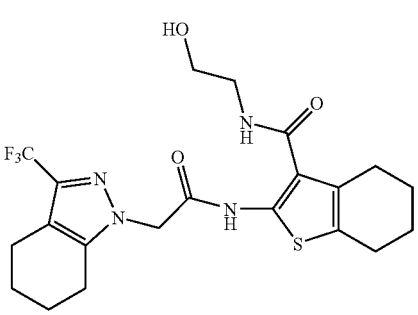

In a similar manner, ethanolamine was used in place of N,N-dimethylethylenediamine to yield the title compound (1 mg, 0.001 mmol, 2%).
MS (ESI): m/z 471.8 [M+H]+.

EXAMPLE 22

2-[2-(3-Trifluoromethyl-4,5,6,7-tetrahydroindazol-1-yl)-acetylamino]-4,5,6,7-tetrahydrobenzo[b]thiophene-3-carboxylic acid (3-hydroxy-2,2-dimethyl-propyl)-amide

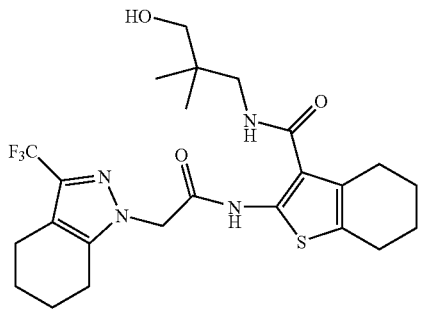

In a similar manner to example 1e, 3-amino-2,2-dimethyl-1-propanol was used in place of N,N-dimethylethylenediamine to yield the title compound (9 mg, 0.018 mmol, 25%).
MS (ESI): m/z 513.7 [M+H]+.

EXAMPLE 23

2-[2-(3-Trifluoromethyl-4,5,6,7-tetrahydroindazol-1-yl)-acetylamino]-4,5,6,7-tetrahydrobenzo[b]thiophene-3-carboxylic acid (pyridin-4-ylmethyl)-amide

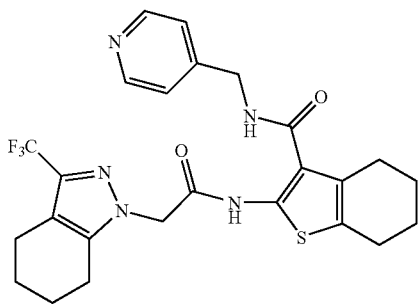

In a similar manner to example 1e, 4-(aminomethyl)pyridine was used in place of N,N-dimethylethylenediamine to yield the title compound (11 mg, 0.022 mmol, 31%).
MS (ESI): m/z 518.5 [M+H]+.

EXAMPLE 24

2-[2-(3-Trifluoromethyl-4,5,6,7-tetrahydroindazol-1-yl)-acetylamino]-4,5,6,7-tetrahydrobenzo[b]thiophene-3-carboxylic acid ([1,4]dioxan-2-ylmethyl)-amide

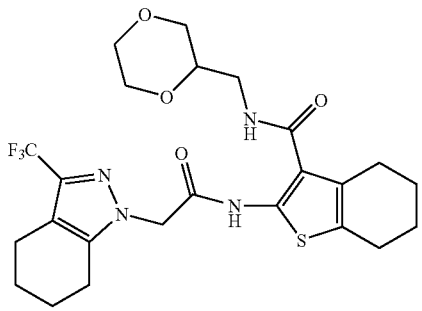

In a similar manner to example 1e, c-[1,4]dioxan-2-yl methylamine was used in place of N,N-dimethylethylenediamine to yield the title compound (17 mg, 0.033 mmol, 46%).
MS (ESI): m/z 527.3 [M+H]+.

EXAMPLE 25

2-[2-(3-Trifluoromethyl-4,5,6,7-tetrahydroindazol-1-yl)-acetylamino]-4,5,6,7-tetrahydrobenzo[b]thiophene-3-carboxylic acid (1,1-dioxo-tetrahydro-1$\Delta^6$-thiophen-3-yl)-amide

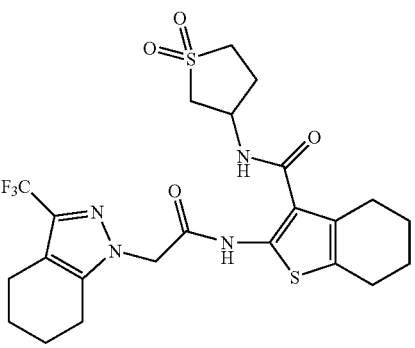

In a similar manner to example 1e, tetrahydro-3-thiophenamine-1,1-dioxide was used in place of N,N-dimethylethylenediamine to yield the title compound (14 mg, 0.026 mmol, 38%).
MS (ESI): m/z 545.3 [M+H]+.

EXAMPLE 26

2-[2-(3-Trifluoromethyl-4,5,6,7-tetrahydroindazol-1-yl)-acetylamino]-4,5,6,7-tetrahydrobenzo[b]thiophene-3-carboxylic acid (2-pyridin-3-yl-ethyl)-amide

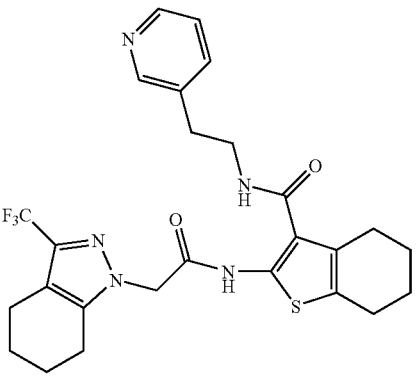

In a similar manner to example 1e, 3-(2-aminoethyl)pyridine was used in place of N,N-dimethylethylenediamine to yield the title compound (24 mg, 0.045 mmol, 64%).
MS (ESI): m/z 532.3 [M+H]+.

EXAMPLE 27

[2-(3-Trifluoromethyl-4,5,6,7-tetrahydroindazol-1-yl)-acetylamino]-4,5,6,7-tetrahydrobenzo[b]thiophene-3-carboxylic acid (5-dimethylaminomethyl-furan-2-ylmethyl)-amide

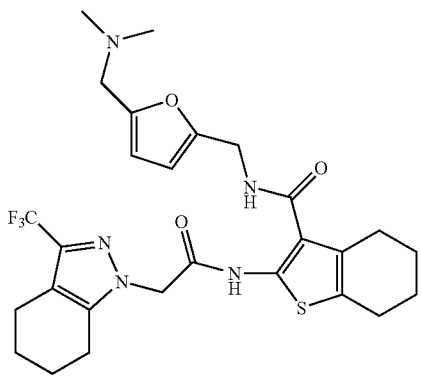

In a similar manner to example 1e, C-(5-Dimethylaminomethyl-furan-2-yl)-methylamine was used in place of N,N-dimethylethylenediamine to yield the title compound as a TFA salt (23 mg, 0.033 mmol, 48%).
MS (ESI): m/z 565.0 [M+H]$^+$.

EXAMPLE 28

2-[2-(3-Trifluoromethyl-4,5,6,7-tetrahydroindazol-1-yl)-acetylamino]-4,5,6,7-tetrahydrobenzo[b]thiophene-3-carboxylic acid (1,5-dimethyl-1H-pyrazol-3-ylmethyl)-amide

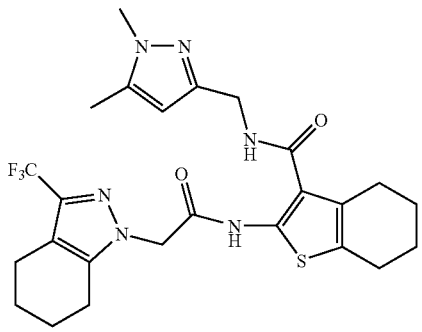

In a similar manner to example 1e, (1,5-dimethylpyrazol-3-yl)methylamine was used in place of N,N-dimethylethylenediamine to yield the title compound (23 mg, 0.043 mmol, 61%).
MS (ESI): m/z 535.3 [M+H]$^+$.

EXAMPLE 29

2-[2-(3-Trifluoromethyl-4,5,6,7-tetrahydroindazol-1-yl)-acetylamino]-4,5,6,7-tetrahydrobenzo[b]thiophene-3-carboxylic acid [(R)-1-(tetrahydro-furan-2-yl)methyl]-amide

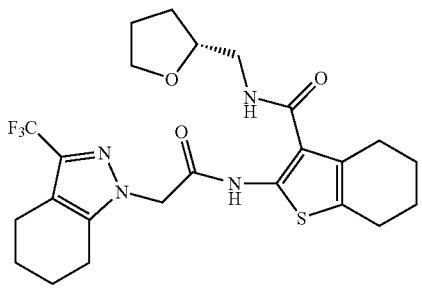

In a similar manner to example 1e, (R)-(−)-tetrahydrofurfurylamine was used in place of N,N-dimethylethylenediamine to yield the title compound (17 mg, 0.034 mmol, 48%).
MS (ESI): m/z 512.0 [M+H]$^+$.

EXAMPLE 30

2-[2-(3-Trifluoromethyl-4,5,6,7-tetrahydroindazol-1-yl)-acetylamino]-4,5,6,7-tetrahydrobenzo[b]thiophene-3-carboxylic acid [(S)-1-(tetrahydro-furan-2-yl)methyl]-amide

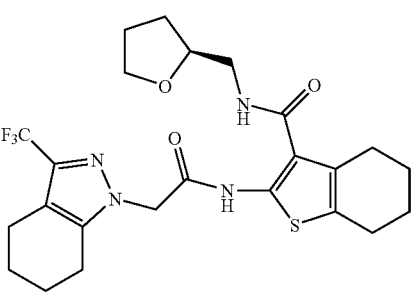

In a similar manner to example 1e, (S)-(+)-tetrahydrofurfurylamine was used in place of N,N-dimethylethylenediamine to yield the title compound (20 mg, 0.038 mmol, 55%).
MS (ESI): m/z 511.9 [M+H]$^+$.

EXAMPLE 31

2-[2-(3-Trifluoromethyl-4,5,6,7-tetrahydroindazol-1-yl)-acetylamino]-4,5,6,7-tetrahydrobenzo[b]thiophene-3-carboxylic acid (5-methyl-pyrazin-2-ylmethyl)-amide

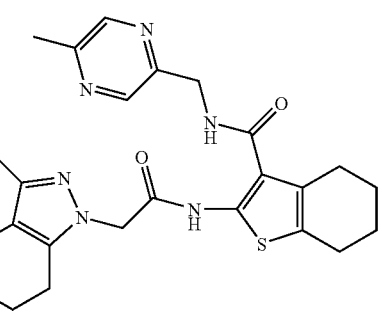

In a similar manner to example 1e, 2-(aminomethyl)-5-methylpyrazine was used in place of N,N-dimethylethylenediamine to yield the title compound (24 mg, 0.045 mmol, 65%).
MS (ESI): m/z 533.5 [M+H]$^+$.

EXAMPLE 32

2-[2-(3-Trifluoromethyl-4,5,6,7-tetrahydroindazol-1-yl)-acetylamino]-4,5,6,7-tetrahydrobenzo[b]thiophene-3-carboxylic acid (2-methanesulfonylamino-ethyl)-amide a) [2-({2-[2-(3-Trifluoromethyl-4,5,6,7-tetrahydroindazol-1-yl)-acetylamino]-4,5,6,7-tetrahydrobenzo[b]thiophene-3-carbonyl}-amino)-ethyl]-carbamic acid tert-butyl ester

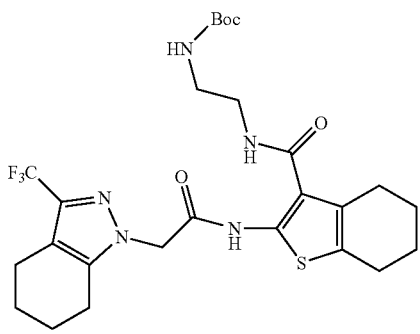

In a similar manner to example 1e, N-Boc-ethylenediamine was used in place of N,N-dimethylethylenediamine to yield the title compound as a white solid (16 mg, 0.028 mmol, 40%).

b) 2-[2-(3-Trifluoromethyl-4,5,6,7-tetrahydroindazol-1-yl)-acetylamino]-4,5,6,7-tetrahydrobenzo[b]thiophene-3-carboxylic acid (2-methanesulfonylamino-ethyl)-amide

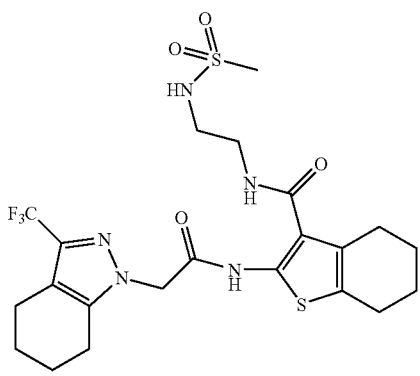

[2-({2-[2-(3-Trifluoromethyl-4,5,6,7-tetrahydroindazol-1-yl)-acetylamino]-4,5,6,7-tetrahydrobenzo[b]thiophene-3-carbonyl}-amino)-ethyl]-carbamic acid tert-butyl ester was dissolved in a solution of DCM (1 mL) and TFA (1 mL) and stirred at RT for 1 h, before concentration in vacuo. The resulting colourless oil was redissolved in DCM (1 mL) and triethylamine (7.70 µL, 0.055 mmol) added, followed by methanesulfonyl chloride (2.20 µL, 0.028 mmol). The resulting mixture was stirred at RT overnight. The sample was concentrated in vacuo and the residue obtained purified by preparative reverse phase HPLC to yield the title compound as a white solid (4 mg, 0.007 mmol, 25%).

MS (ESI): m/z 548.3 [M+H]$^+$.

EXAMPLE 33

2-[2-(3-Trifluoromethyl-4,5,6,7-tetrahydroindazol-1-yl)-acetylamino]-4,5,6,7-tetrahydrobenzo[b]thiophene-3-carboxylic acid (2-methylamino-ethyl)-amide

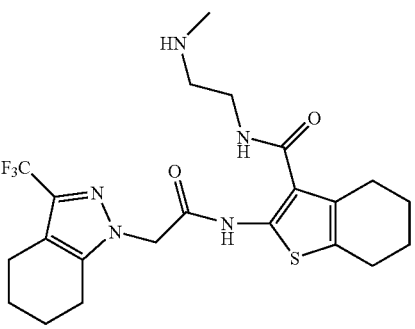

2-[2-(3-Trifluoromethyl-4,5,6,7-tetrahydroindazol-1-yl)-acetylamino]-4,5,6,7-tetrahydrobenzo[b]thiophene-3-carboxylic acid (25 mg, 0.059 mmol) was dissolved in a solution of DCM (1 mL) and DMF (0.2 mL). O-(7-azabenzotriazol-1-yl)-N,N,N',N'-tetramethyluronium hexafluorophosphate (27 mg, 0.070 mmol) was added, followed by N-(2-aminoethyl)-N-methyl carbamic acid tert-butyl ester (12 mg, 0.070 mmol) and N,N-diisopropylethylamine (12.2 µL, 0.070 mmol). The resultant mixture was stirred at RT overnight. The solvent was removed under reduced pressure, and the residue obtained purified by preparative reverse phase HPLC. The resulting residue was dissolved in a solution of DCM (0.5 mL) and TFA (0.5 mL) and stirred at RT for 30 min, before concentration in vacuo. The residue obtained was purified by preparative reverse phase HPLC to yield the title compound as a TFA salt (15 mg, 0.025, 42%).

MS (ESI): m/z 484.7 [M+H]$^+$.

EXAMPLE 34

2-[2-(3-Trifluoromethyl-4,5,6,7-tetrahydroindazol-1-yl)-acetylamino]-4,5,6,7-tetrahydrobenzo[b]thiophene-3-carboxylic acid (4-amino-butyl)-amide

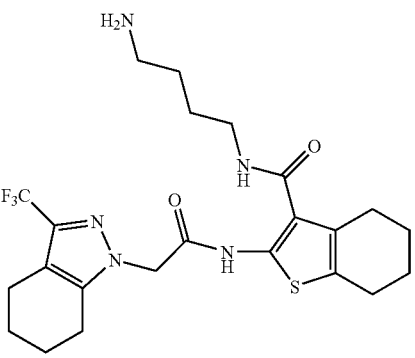

In a similar manner to example 33, N-Boc-1,4-diaminobutane was used in place of N-(2-aminoethyl)-N-methyl carbamic acid tert-butyl ester to yield the title compound as a TFA salt (2 mg, 0.003 mmol, 5%).

MS (ESI): m/z 498.5 [M+H]$^+$.

EXAMPLE 35

2-[2-(3-Trifluoromethyl-4,5,6,7-tetrahydroindazol-1-yl)-acetylamino]-4,5,6,7-tetrahydrobenzo[b]thiophene-3-carboxylic acid (2-ethylamino-ethyl)-amide

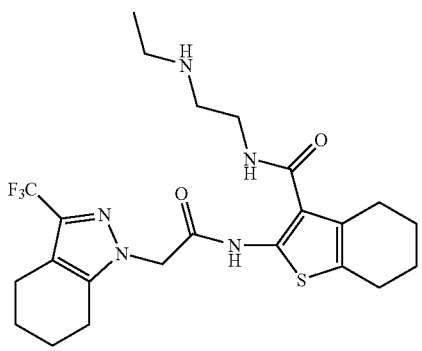

In a similar manner to example 33, N-Boc-N-ethyl-ethylenediamine.HCl was used in place of N-(2-aminoethyl)-N-methyl carbamic acid tert-butyl ester to yield the title compound as a TFA salt (7 mg, 0.011 mmol, 15%).
MS (ESI): m/z 498.5 [M+H]$^+$.

EXAMPLE 36

2-[2-(3-Trifluoromethyl-4,5,6,7-tetrahydroindazol-1-yl)-acetylamino]-4,5,6,7-tetrahydrobenzo[b]thiophene-3-carboxylic acid ((R)-1-pyrrolidin-3-ylmethyl)-amide

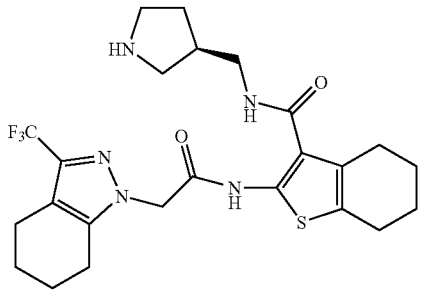

In a similar manner to example 33, (S)-3-aminomethyl-1-N-Boc-pyrrolidine was used in place of N-(2-aminoethyl)-N-methyl carbamic acid tert-butyl ester to yield the title compound as a TFA salt (5 mg, 0.009 mmol, 12%).
MS (ESI): m/z 510.3 [M+H]$^+$.

EXAMPLE 37

2-[2-(3-Trifluoromethyl-4,5,6,7-tetrahydroindazol-1-yl)-acetylamino]-4,5,6,7-tetrahydrobenzo[b]thiophene-3-carboxylic acid azetidin-3-ylamide

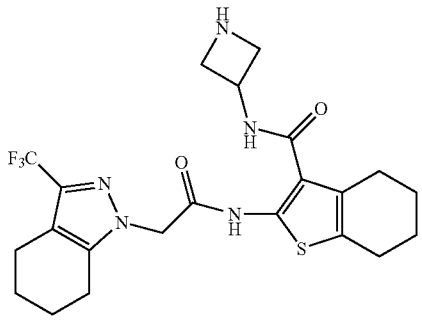

In a similar manner to example 33, 3-amino-1-N-Boc-azetidine was used in place of N-(2-aminoethyl)-N-methyl carbamic acid tert-butyl ester to yield the title compound as a TFA salt (11 mg, 0.018 mmol, 25%).
MS (ESI): m/z 482.4 [M+H]$^+$.

EXAMPLE 38

2-[2-(3-Trifluoromethyl-4,5,6,7-tetrahydroindazol-1-yl)-acetylamino]-4,5,6,7-tetrahydrobenzo[b]thiophene-3-carboxylic acid (azetidin-3-ylmethyl)-amide

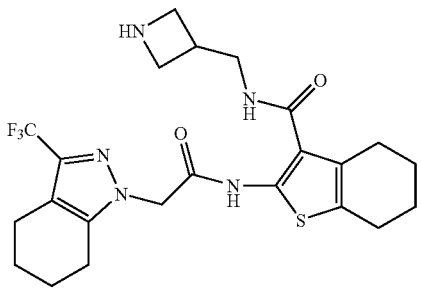

In a similar manner to example 33, 3-aminomethyl-1-N-Boc-azetidine was used in place of N-(2-aminoethyl)-N-methyl carbamic acid tert-butyl ester to yield the title compound as a TFA salt (10 mg, 0.016 mmol, 23%).
MS (ESI): m/z 496.6 [M+H]$^-$.

EXAMPLE 39

2-[2-(3-Trifluoromethyl-4,5,6,7-tetrahydroindazol-1-yl)-acetylamino]-4,5,6,7-tetrahydrobenzo[b]thiophene-3-carboxylic acid (3-amino-propyl)-amide

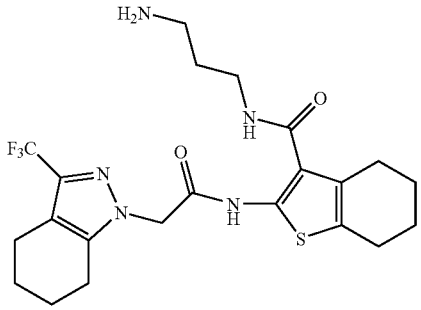

In a similar manner to example 33, N-Boc-1,4-diaminopropane was used in place of N-(2-aminoethyl)-N-methyl carbamic acid tert-butyl ester to yield the title compound as a TFA salt (6 mg, 0.0012 mmol, 21%).
MS (ESI): m/z 484.6 [M+H]$^+$.

EXAMPLE 40

2-[2-(3-Trifluoromethyl-4,5,6,7-tetrahydroindazol-1-yl)-acetylamino]-4,5,6,7-tetrahydrobenzo[b]thiophene-3-carboxylic acid ethylamide

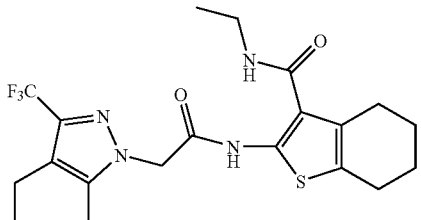

2-[2-(3-Trifluoromethyl-4,5,6,7-tetrahydroindazol-1-yl)-acetylamino]-4,5,6,7-tetrahydrobenzo[b]thiophene-3-carboxylic acid (20 mg, 0.047 mmol) was dissolved in a solution of DCM (800 µL) and DMF (200 µL). Polymer supported carbodiimide (loading 1.22 mmol/g, 53 mg, 0.064 mmol) was added, followed by ethylamine (2.0 M solution in THF, 94.0 µl, 0.188 mmol). The resultant mixture was heated in a Biotage SmithCreator microwave at 120° C. for 15 min. The resin was filtered off and washed through with MeOH (2×50 mL), EtOAc (2×20 mL) and MeCN (2×20 mL). The combined filtrate was concentrated in vacuo, and the residue obtained purified by preparative reverse phase HPLC to afford the title compound as a white solid (1 mg, 0.003 mmol, 6%).

MS (ESI): m/z 455.5 [M+H]$^+$.

EXAMPLE 41

2-[2-(3-Trifluoromethyl-4,5,6,7-tetrahydroindazol-1-yl)-acetylamino]-4,5,6,7-tetrahydrobenzo[b]thiophene-3-carboxylic acid dimethylamide

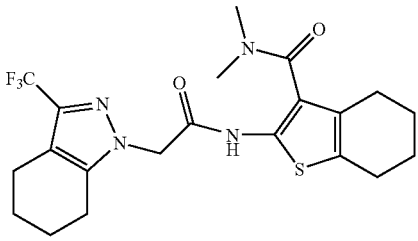

In a similar manner to example 40, dimethylamine (2.0 M solution in THF) was used in place of ethylamine (2.0 M solution in THF) to yield the title compound (1 mg, 0.003 mmol, 6%).

MS (ESI): m/z 455.3 [M+H]$^+$.

EXAMPLE 42

N-(3-Hydroxymethyl-4,5,6,7-tetrahydro-benzo[b]thiophen-2-yl)-2-(3-trifluoromethyl-4,5,6,7-tetrahydroindazol-1-yl)-acetamide a) N-(4,5,6,7-Tetrahydro-benzo[b]thiophen-2-yl)-2-(3-trifluoromethyl-4,5,6,7-tetrahydro indazol-1-yl)-acetamide

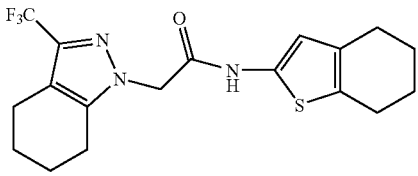

2-[2-(3-Trifluoromethyl-4,5,6,7-tetrahydroindazol-1-yl)-acetylamino]-4,5,6,7-tetrahydrobenzo[b]thiophene-3-carboxylic acid (200 mg, 0.47 mmol) and copper powder (45 mg, 0.70 mmol) were suspended in quinoline (4 mL) and the resulting mixture heated in a Biotage SmithCreator microwave at 200° C. for 10 min. The mixture was diluted with water (5 mL), acidified to pH 1 with 5 M HCl, and extracted with diethyl ether (3×50 mL). The combined organics were dried over sodium sulfate and concentrated in vacuo. The residue obtained was purified by silica gel chromatography using DCM as eluent, to afford the title compound as an off-white solid (170 mg, 0.44 mmol, 95%).

b) N-(3-Formyl-4,5,6,7-tetrahydro-benzo[b]thiophen-2-yl)-2-(3-trifluoromethyl-4,5,6,7-tetrahydroindazol-1-yl)-acetamide

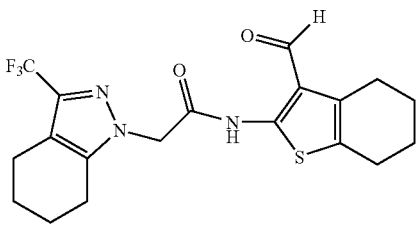

Phosphorus oxychloride (399 µl, 4.28 mmol) was added dropwise to a stirred solution of DMF (332 µl, 4.28 mmol) in 1,2-dichloroethane (3 mL). A suspension of N-(4,5,6,7-tetrahydro-benzo[b]thiophen-2-yl)-2-(3-trifluoromethyl-4,5,6,7-tetrahydroindazol-1-yl)-acetamide (1.64 g, 4.28 mmol) in 1,2-dichloroethane (80 mL) was added portionwise with stirring, and the mixture stirred at RT for 15 min. The resulting yellow solution was refluxed for 20 min. After cooling to RT, the mixture was added to a solution of sodium acetate (13.6 g, 166 mmol, in 130 mL of water) and the solution heated at 50° C. for 20 min. After cooling to RT, the solution was diluted with DCM (100 mL), and the phases separated. The aqueous layer was extracted with DCM (100 mL) and the combined organics washed with saturated sodium bicarbonate solution (100 mL), dried over sodium sulphate and concentrated in vacuo to afford the title compound as a yellow solid (1.52 g, 3.70 mmol, 86%).

c) N-(3-Hydroxymethyl-4,5,6,7-tetrahydro-benzo[b]thiophen-2-yl)-2-(3-trifluoromethyl-4,5,6,7-tetrahydroindazol-1-yl)-acetamide

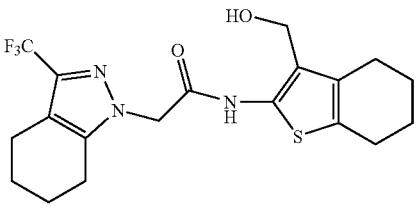

N-(3-Formyl-4,5,6,7-tetrahydro-benzo[b]thiophen-2-yl)-2-(3-trifluoromethyl-4,5,6,7-tetrahydroindazol-1-yl)-acetamide (1.30 g, 3.16 mmol) was added portionwise, with stirring, to a solution of sodium borohydride (359 mg, 9.49 mmol) in EtOH (300 mL). The resulting mixture was stirred at RT for 40 min. Acetic acid was added dropwise until the effervescence ceased. The resulting mixture was concentrated in vacuo to afford an off-white solid. The solid was dissolved in diethyl ether (200 mL) and washed with water (100 mL). The organics were dried over sodium sulfate and concentrated in vacuo to yield the title compound as a yellow solid (1.27 g, 3.08 mmol, 97%).

MS (ESI): m/z 414.4 [M+H]$^+$.

EXAMPLE 43

2-(2-(3-(trifluoromethyl)-4,5-dihydroindazole-1-yl)acetamido-4,5,6,7-tetrahydrothieno[2,3-c]pyran-3-carboxamide a) 2-amino-5,7-dihydro-4H-thieno[2,3-c]pyran-3-carboxamide

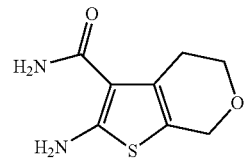

Tetrahydro-4H-pyran-4-one (1.77 g, 17.7 mmol), cyanoacetamide (1.50 g, 17.7 mmol) and sulphur (560 mg, 17.7 mmol) were stirred in EtOH (6 mL). Diethylamine (2 mL, 19.4 mmol) was added and the reaction stirred at RT overnight. A precipitate had formed. Water (10 mL) was added and the solid filtered, washed with water (10 mL), then heptane (50 mL) to give a pale red solid. The solid was stirred in EtOAc/MeOH (75 mL), then filtered to give an off white solid (1.64 g, 8.3 mmol, 47%).

MS (ESI): m/z 199 [M+H]$^+$.

b) 2-(2-(3-(trifluoromethyl)-4,5-dihydroindazole-1-yl)acetamido-4,5,6,7-tetrahydrothieno[2,3-c]pyran-3-carboxamide

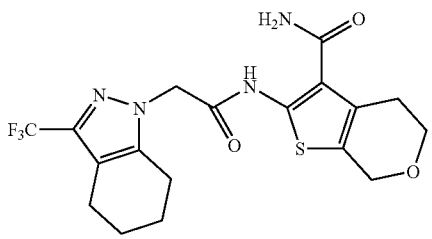

2-amino-5,7-dihydro-4H-thieno[2,3-c]pyran-3-carboxamide (40 mg, 0.20 mmol) and 2-(3-(trifluoromethyl)-4,5,6,7-tetrahydroindazole-1-yl)acetic acid (50 mg, 0.20 mmol) were dissolved in DCM/DMF (3 mL/50 μL) and polymer supported carbonyldiimidazole (330 mg, 1.2 mmol/g, 0.396 mmol) added. The reaction mixture was heated at 120° C. for 10 min in the microwave. The reaction mixture was filtered washing with MeOH (10 mL), EtOAc (10 mL), and MeCN (10 mL). The filtrate was concentrated in vacuo to give a yellow gum. Purification by preparative reverse phase HPLC gave desired product as a white solid (7.6 mg, 0.018 mmol, 9%).

MS (ESI): m/z 429 [M+H]$^+$.

EXAMPLE 44

2-(2-(3-(trifluoromethyl)-4,5,6,7-tetrahydro-1H-indazole-1-yl)acetamido)thiophene-3-carboxamide a) 2-aminothiophene-3-carboxamide

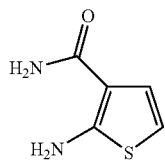

A solution of 2,5-dihydroxy-1,4-dithiane (5.83 g, 38.3 mmol), 2-cyanoacetamide (8.4 g, 99.1 mmol) and triethylamine (10 mL, 71.9 mmol) in EtOH (30 mL) was heated at 70° C. for 2 h then allowed to stand overnight. The reaction mixture was reduced by half in vacuo and the solution cooled with ice to produce a precipitate. The solid was filtered off, washing with heptane (200 mL) to give product as a brown solid (7.12 g, 50.1 mmol, 51

1H NMR (400 MHz, CD$_3$OD): □6.21 (d, 1H), 6.93 (d, 1H).

b) 2-(2-(3-(trifluoromethyl)-4,5,6,7-tetrahydroindazole-1-yl)acetamido)thiophene-3-carboxamide

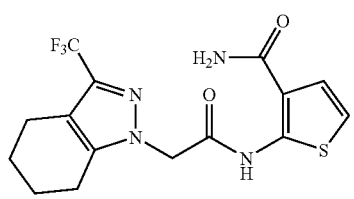

2-aminothiophene-3-carboxamide (23 mg, 0.16 mmol) and 2-(3-(trifluoromethyl)-4,5,6,7-tetrahydro-1H-indazole-1-yl)acetic acid (40 mg, 0.16 mmol) were dissolved in DCM/DMF (2 mL/50 μL) and polymer supported carbonyldiimidazole (264 mg, 1.2 mmol/g, 0.32 mmol) added. The reaction mixture was heated at 120° C. for 10 min in a Biotage Smith-Creator microwave. The reaction mixture was filtered washing with MeOH (10 mL), EtOAc (10 mL), and MeCN (10 mL). The filtrate was concentrated in vacuo to give a yellow gum. Purification by preparative reverse phase HPLC gave desired product (1 mg, 2%).

MS (ESI): m/z 373 [M+H]$^+$.

EXAMPLE 45

6-methyl-2-(2-(3-(trifluoromethyl)-4,5,6,7-tetrahydroindazole-1-yl)acetamido-4,5,6,7-tetrahydrothieno[2,3-c]pyridine-3-carboxamide a) 2-amino-6-methyl-4,5,6,7-tetrahydrothieno[2,3-c]pyridine-3-carboxamide

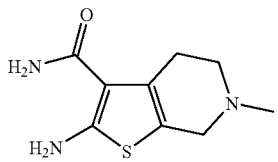

N-methyl-4-piperidone (2.00 g, 17.7 mmol), cyanoacetamide (1.50 g, 17.7 mmol) and sulfur (560 mg, 17.7 mmol) were stirred in EtOH (6 mL). Diethylamine (2 mL, 19.4 mmol) was added and the reaction stirred at RT overnight. A precipitate had formed. Water (10 mL) was added and the solid filtered, washing with water (10 mL), heptane (50 mL) to give a red/orange solid (850 mg, 4.03 mmol, 23%).

MS (ESI): m/z 212 [M+H]$^+$.

b) 6-methyl-2-(2-(3-(trifluoromethyl)-4,5,6,7-tetrahydroindazole-1-yl)acetamido-4,5,6,7-tetrahydrothieno[2,3-c]pyridine-3-carboxamide

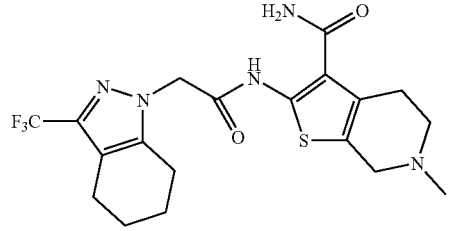

In a similar manner to example 43b, 2-amino-6-methyl-4,5,6,7-tetrahydrothieno[2,3-c]pyridine-3-carboxamide) was used in place of 2-amino-5,7-dihydro-4H-thieno[2,3-c]pyran-3-carboxamide to yield the title compound as the TFA salt (11 mg, 0.02 mmol, 10%).

MS (ESI): m/z 442 [M+H]$^+$.

EXAMPLE 46

2-(2-(3-(trifluoromethyl)-4,5,6,7-tetrahydroindazole-1-yl)acetamido-4,5,6,7-tetrahydro thieno[2,3-c]pyridine-3-carboxamide a) tert-butyl 2-amino-3-carbamoyl-4,5-dihydrothieno[2,3-c]pyridine-6(7H)-carboxylate

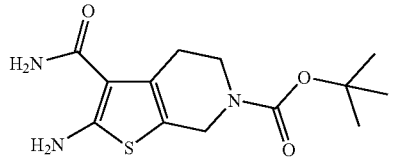

tert-butyl 4-oxopiperidine-1-carboxylate (9.95 g, 50 mmol), cyanoacetamide (4.24 g, 50 mmol) and sulfur (1.6 g, 50 mmol) were stirred in EtOH (20 mL). Diethylamine (5 mL, 48 mmol) was added and the reaction stirred at RT overnight. A gum had formed in the solution. Water (50 mL) was added and the solid filtered, washing with heptane (150 mL) to give a brown/yellow solid (12.0 g, 40 mmol, 81%).

MS (ESI): m/z 298 [M+H]+.

b) tert-butyl 3-carbamoyl-2-(2-(3-(trifluoromethyl)-4,5,6,7-tetrahydroindazole-1-yl)acetamido-4,5-dihydrothieno[2,3-c]pyridine-6(7H)-carboxylate

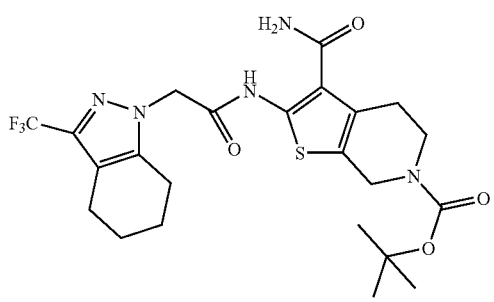

tert-butyl 2-amino-3-carbamoyl-4,5-dihydrothieno[2,3-c]pyridine-6(7H)-carboxylate (72 mg, 0.24 mmol) and 2-(3-(trifluoromethyl)-4,5,6,7-tetrahydro-1H-indazole-1-yl)acetic acid (60 mg, 0.24 mmol) were dissolved in DCM/DMF (3 mL/50 μL) and polymer supported carbonyldiimidazole (396 mg, 1.2 mmol/g, 0.475 mmol) added. The reaction mixture was heated at 120° C. for 10 min in the microwave. The reaction mixture was filtered washing with MeOH (10 mL), EtOAc (10 mL), and MeCN (10 mL). The filtrate was concentrated in vacuo to give product as a yellow gum (67 mg, 0.0127 mmol, 53%).

MS (ESI): m/z 528 [M+H]+.

c) 2-(2-(3-(trifluoromethyl)-4,5,6,7-tetrahydroindazole-1-yl)acetamido-4,5,6,7-tetrahydrothieno[2,3-c]pyridine-3-carboxamide

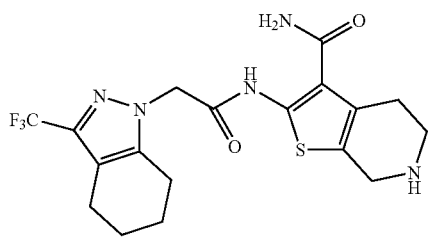

tert-butyl 3-carbamoyl-2-(2-(3-(trifluoromethyl)-4,5,6,7-tetrahydro-1H-indazole-1-yl)acetamido-4,5-dihydrothieno[2,3-c]pyridine-6(7H)-carboxylate was dissolved in TFA/DCM (2 mL/2 mL) and stirred at RT for 2 h. The reaction mixture was concentrated in vacuo and purified by preparative reverse phase HPLC to give desired product as a white solid as the TFA salt (12 mg, 0.023 mmol, 22%).

MS (ESI): m/z 428 [M+H]+.

EXAMPLE 47

4-5-dimethyl-2-(2-(3-(trifluoromethyl)-4,5,6,7-tetrahydroindazole-1-yl)acetamido) thiophene-3-carboxamide a) 2-amino-4,5-dimethylthiophene-3-carboxamide

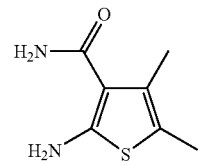

2-butanone (1.27 g, 17.6 mmol), cyanoacetamide (1.50 g, 17.6 mmol) and sulphur (560 mg, 17.6 mmol) were stirred in EtOH (6 mL). Diethylamine (2 mL, 19.4 mmol) was added and the reaction stirred at RT overnight. Water (20 mL) was added and the reaction mixture extracted into EtOAc (20 mL×3), the combined EtOAc layers were then washed with brine, dried over MgSO4, filtered and the solvent removed in vacuo to give product as a yellow solid (435 mg, 2.56 mmol, 15%).

b) 4-5-dimethyl-2-(2-(3-(trifluoromethyl)-4,5,6,7-tetrahydroindazole-1-yl)acetamido) thiophene-3-carboxamide

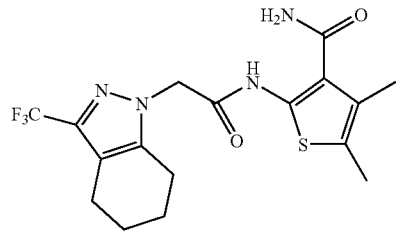

In a similar manner to example 43b, 2-Amino-4,5-dimethylthiophene-3-carboxamide was used in place of 2-amino-5,7-dihydro-4H-thieno[2,3-c]pyran-3-carboxamide to yield the title compound (3.1 mg, 0.008 mmol, 4%).

MS (ESI): m/z 401 [M+H]+.

EXAMPLE 48

4-Ethyl-5-methyl-2-(2-(3-(trifluoromethyl)-4,5,6,7-tetrahydroindazole-1-yl)acetamido) thiophene-3-carboxamide a) 2-Amino-4-ethyl-5-methylthiophene-3-carboxamide

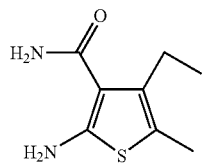

2-pentanone (1.52 g, 17.6 mmol), cyanoacetamide (1.50 g, 17.6 mmol) and sulphur (560 mg, 17.6 mmol) were stirred in EtOH (6 mL). Diethylamine (2 mL, 19.4 mmol) was added and the reaction stirred at RT overnight. Water (20 mL) was added and the precipitate filtered off and washed with heptane (100 mL) to give the product as a cream solid (150 mg, 0.81 mmol, 5%).

1H NMR (400 MHz, CDCl3): ☐1.17 (t, 3H), 2.18 (s, 3H), 2.61 (q, 2H), 5.48 (bs, 2H), 5.84 (bs, 2H).

b) 4-Ethyl-5-methyl-2-(2-(3-(trifluoromethyl)-4,5,6,7-tetrahydroindazole-1-yl)acetamide) thiophene-3-carboxamide

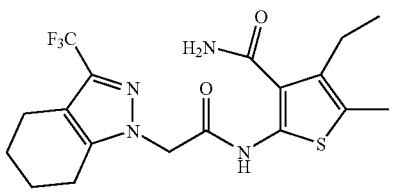

In a similar manner to example 43b, 2-Amino-4-ethyl-5-methylthiophene-3-carboxamide was used in place of 2-amino-5,7-dihydro-4H-thieno[2,3-c]pyran-3-carboxamide to yield the title compound (7.8 mg, 0.019 mmol, 9%).
MS (ESI): m/z 415 [M+H]$^+$.

EXAMPLE 49

2-(2-(3-(trifluoromethyl)-4,5,6,7-tetrahydroindazole-1-yl)propanamido)-4,5,6,7-tetrahydrobenzo[b]thiophene-3-carboxamide a) 2-(3-chloropropanamido)-4,5,6,7-tetrahydrobenzo[b]thiophene-3-carboxamide

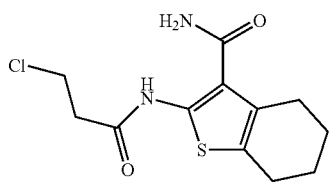

2-amino-4,5,6,7-tetrahydrobenzo[b]thiophene-3-carboxamide (250 mg, 1.28 mmol) and triethylamine (0.18 mL, 1.28 mmol) were stirred in DCM (5 mL). 3-chloropropionyl-chloride (162 mg, 1.28 mmol) was added dropwise under a nitrogen atmosphere. Stirring was continued for 2 h. 2 M HCl (20 mL) was added and the reaction mixture extracted into DCM (3×50 mL). The combined DCM layers were washed with brine, dried over MgSO$_4$, filtered and the solvent removed in vacuo to give the desired product as a yellow solid (290 mg, 1.01 mmol, 79%).
1H NMR (400 MHz, CDCl$_3$): □1.86 (m, 4H), 2.72 (m, 4H), 2.91 (t, 2H), 3.86 (t, 2H), 5.73 (s, 2H), 12.1 (s, 1H).

b) 2-(2-(3-(trifluoromethyl)-4,5,6,7-tetrahydroindazole-1-yl)propanamido)-4,5,6,7-tetrahydrobenzo[b]thiophene-3-carboxamide

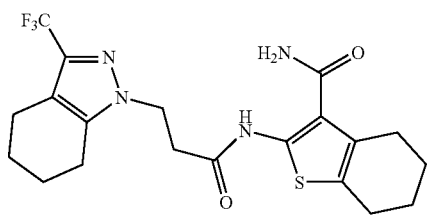

3-(trifluoromethyl)-4,5,6,7-tetrahydroindazole (50 mg, 0.263 mmol) was dissolved in DMF (2 mL). NaH (60% [w/w] suspension in oil, 11 mg, 0.275 mmol) was added followed by potassium iodide (2 mg, catalyst) and the reaction mixture stirred at RT for 30 min. 2-(3-chloropropanamido)-4,5,6,7-tetrahydrobenzo[b]thiophene-3-carboxamide (75 mg, 0.262 mmol) was then added and the reaction mixture heated at 120° C. for 400 sec in a Biotage SmithCreator microwave. Water was added followed by EtOAc (3×10 mL) extraction. The EtOAc layers were washed with water (5×5 mL), brine, dried over MgSO$_4$, filtered and the solvent removed in vacuo to give a yellow gum. Purification by preparative reverse phase HPLC gave desired product (22.7 mg, 0.052 mmol, 20%).
MS (ESI): m/z 441 [M+H]$^+$.

EXAMPLE 50

Ethyl 1-(2-(3-carbamoyl-4,5,6,7-tetrahydrobenzo[b]thiophen-2-ylamino)-2-oxoethyl)-3-(trifluoromethyl)pyrazole-4-carboxylate a) 2-(2-bromoacetamido)-4,5,6,7-tetrahydrobenzo[b]thiophene-3-carboxamide

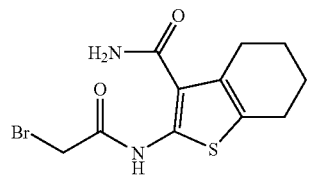

2-amino-4,5,6,7-tetrahydrobenzo[b]thiophene-3-carboxamide (500 mg, 2.55 mmol) and triethylamine (0.35 mL, 2.55 mmol) were stirred in DCM (10 mL). Bromoacetylbromide was added dropwise under a nitrogen atmosphere. Stirring was continued for 3 h. 2 M HCl (20 mL) was added and the reaction mixture extracted into DCM (3×50 mL). The combined DCM layers were washed with brine, dried over MgSO$_4$, filtered and the solvent removed in vacuo to give the desired product as a cream solid (760 mg, 2.40 mmol, 94%).
1H NMR (400 MHz, CDCl$_3$): □1.86 (m, 4H), 2.72 (m, 4H), 4.05 (s, 2H), 5.7 (s, 2H), 12.8 (s, 1H).

b) Ethyl 1-(2-(3-carbamoyl-4,5,6,7-tetrahydrobenzo[b]thiophen-2-ylamino)-2-oxoethyl)-3-(trifluoromethyl)pyrazole-4-carboxylate

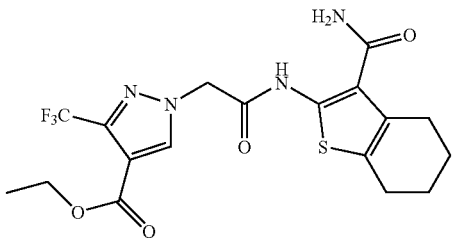

NaH (60% [w/w] suspension in oil, 10 mg, 0.25 mmol) was added to a solution of ethyl-3-(trifluoromethyl)pyrazole-4-carboxylate (25 mg, 0.056 mmol) in DMF (2 mL). The reaction mixture was stirred at RT for 60 min before the addition of 2-(2-bromoacetamido)-4,5,6,7-tetrahydrobenzo[b]thiophene-3-carboxamide. The reaction mixture was heated at 120° C. for 10 min in the microwave. Water (5 µL) was added and the reaction mixture extracted with EtOAc (3×10 mL). The combined EtOAc layers were washed with water (5×5 mL), brine (5 mL), dried over MgSO$_4$, filtered and the solvent removed under reduced pressure to give the crude reaction mixture as a yellow solid (44 mg, 0.01 mmol). Purification by preparative reverse phase HPLC gave the desired product (10 mg, 0.024 mmol, 19%).
MS (ESI): m/z 444 [M+H]$^+$.

EXAMPLE 51

2-(2-(4-(aminomethyl)-3-(trifluoromethyl)pyrazol-1-yl)acetamido)-4,5,6,7-tetrahydrobenzo[b]thiophene-3-carboxamide a) 2-(2-(4-cyano-3-(trifluoromethyl)pyrazol-1-yl)acetamido)-4,5,6,7-tetrahydrobenzo[b]thiophene-3-carboxamide

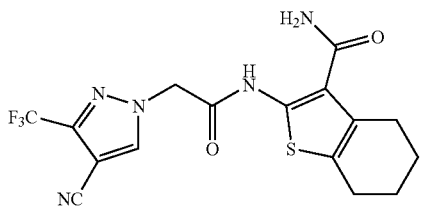

NaH (60% [w/w] suspension in oil, 130 mg, 3.25 mmol) was added to a solution of 3-(trifluoromethyl)-4-cyanopyrazole (520 mg, 3.23 mmol) in DMF (10 mL). The reaction mixture was stirred at RT for 1 h before adding 2-(2-bromoacetamido)-4,5,6,7-tetrahydrobenzo[b]thiophene-3-carboxamide (1.023 g, 3.23 mmol). The reaction mixture was heated at 65° C. for 4 h then allowed to cool to RT. Water (20 mL) was added and the reaction mixture extracted with EtOAc (3×20 mL). The combined EtOAc layers were washed with water (5×20 mL), brine (20 mL), dried over MgSO$_4$, filtered, and the solvent removed under reduced pressure to give the crude reaction mixture as a cream solid. Purification by flash chromatography (eluent 1:1 EtOAc:heptane) gave desired product (626 mg, 1.58 mmol, 49%).

MS (ESI): m/z 398 [M+H]$^+$.

b) 2-(2-(4-(aminomethyl)-3-(trifluoromethyl)pyrazol-1-yl)acetamido)-4,5,6,7-tetrahydro benzo[b]thiophene-3-carboxamide

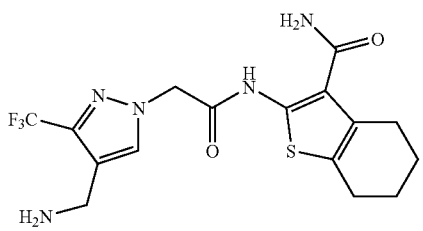

2-(2-(4-cyano-3-(trifluoromethyl)pyrazol-1-yl)acetamido)-4,5,6,7-tetrahydrobenzo[b]thiophene-3-carboxamide (270 mg, 68 mmol) was dissolved in MeOH (10 mL). A catalytic amount of CoCl$_2$.6H$_2$O was added. Sodium borohydride (51 mg, 13.7 mmol) was added in a portionwise manner. The reaction mixture was left to stir overnight. Water (20 mL) was added and the reaction mixture extracted with EtOAc (3×20 mL). The combined EtOAc layers were washed with brine (20 mL), dried over MgSO$_4$, filtered and the solvent removed under reduced pressure to give the crude reaction mixture as a cream solid (120 mg). An analytically pure sample was obtained by purification of 20 mg of crude product. Preparative reverse phase HPLC gave desired product as the TFA salt (2.5 mg, 0.049 mmol, 1%).

MS (ESI): m/z 402 [M+H]$^+$.

EXAMPLE 52

2-(2-(4-((isopropylamino)methyl)-3-(trifluoromethyl)pyrazol-1-yl)acetamido)-4,5,6,7-tetrahydrobenzo[b]thiophene-3-carboxamide

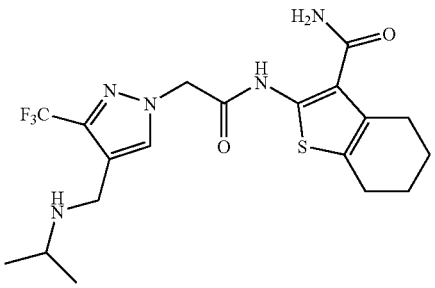

2-(2-(4-(aminomethyl)-3-(trifluoromethyl)pyrazol-1-yl)acetamido)-4,5,6,7-tetrahydrobenzo[b]thiophene-3-carboxamide (25 mg, 0.062 mmol) was dissolved in DCM (1 mL). Acetone (4 mg, 0.068 mmol) was added followed by triacetoxyborohydride (53 mg, 0.25 mmol). The reaction mixture was stirred overnight, concentrated in vacuo, DMF (1 mL) added, filtered free of solid, and purified by preparative reverse phase HPLC to give desired product as the TFA salt (2.8 mg, 0.006 mmol, 10%).

MS (ESI): m/z 444 [M+H]$^+$.

EXAMPLE 53

2-(2-(4-((cyclohexylamino)methyl)-3-(trifluoromethyl)pyrazol-1-yl)acetamido)-4,5,6,7-tetrahydrobenzo[b]thiophene-3-carboxamide

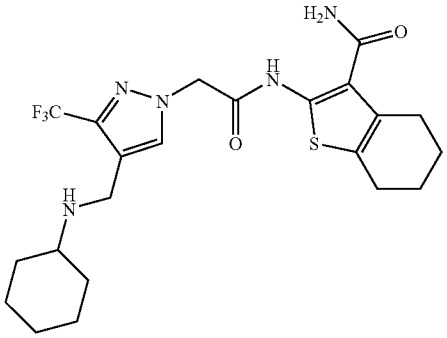

In a similar manner to example 52, cyclohexanone was used in place of acetone to yield the title compound the TFA salt (4.1 mg, 0.008 mmol, 14%).

MS (ESI): m/z 441 [M+H]$^+$.

EXAMPLE 54

2-(2-(4-(dimethylamino)methyl)-3-(trifluoromethyl)pyrazol-1-yl)acetamido)-4,5,6,7-tetrahydrobenzo[b]thiophene-3-carboxamide a) (3-(trifluoromethyl)-1H-pyrazol-4-yl)methanol

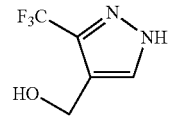

Ethyl 3-(trifluoromethyl)-1H-pyrazole-4-carboxylate (5.00 g, 24 mmol) was dissolved in dry THF (50 mL). LiAlH$_4$ (912 mg, 24.4 mmol) was added portionwise with care. The reaction mixture was stirred at RT for 3 h. MeOH (50 mL) was added dropwise and stirring continued for 30 min before concentrating in vacuo to give an off white solid. EtOAc (50 mL) was added and the solid was stirred for 30 min before filtering. The filtrate was concentrated and this procedure was repeated 4 times before the filtrates, after concentration in vacuo, were combined and purified by flash column chromatography (silica gel; eluent EtOAc:heptane, 4:1) to give the desired product (2.1 g, 12.6 mmol, 53%).

1H NMR (400 MHz, CD₃OD): □4.65 (s, 2H), 7.63 (s, 1H)

b) 3-(trifluoromethyl)-1H-pyrazole-4-carbaldehyde

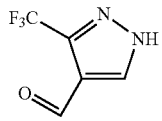

(3-(trifluoromethyl)-1H-pyrazol-4-yl)methanol (600 mg, 3.61 mmol) was dissolved in MeCN (5 mL). MnO₂ (785 mg, 9.03 mmol) was added. The reaction mixture was heated at 120° C. for 5 min in the microwave. The reaction mixture was filtered through decalite, washed with MeCN (30 mL), then concentrated in vacuo and purified by flash column chromatography (silica gel; eluent EtOAc:heptane, 1:1) to give the desired product (200 mg, 1.22 mmol, 34%).

1H NMR (400 MHz, CD₃OD): □8.44 (s, 1H), 9.95 (s, 1H)

c) 2-(2-(4-formyl-3-(trifluoromethyl)pyrazol-1-yl) acetamido)-4,5,6,7-tetrahydrobenzo[b]thiophene-3-carboxamide

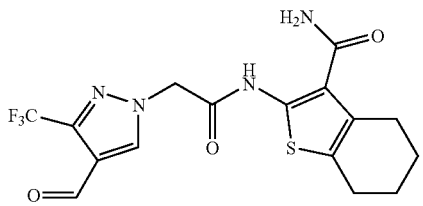

3-(trifluoromethyl)pyrazole-4-carbaldehyde (200 mg, 1.22 mmol) was dissolved in DMF (10 mL). NaH (60% [w/w] suspension in oil, 50 mg, 1.25 mmol) was added portionwise and the reaction mixture stirred at RT for 30 min. 2-(2-bromoacetamido)-4,5,6,7-tetrahydrobenzo[b]thiophene-3-carboxamide (386 mg, 1.22 mmol) was added and the reaction mixture heated at 65° C. for 2 h, then allowed to cool to RT. Water (10 mL) was added and the reaction mixture extracted with EtOAc (3×10 mL). The combined EtOAc layers were washed with water (5×10 mL), brine (10 mL), dried over MgSO₄, filtered, and the solvent removed under reduced pressure to give the desired product (470 mg, 1.17 mmol, 96%).

MS (ESI): m/z 401 [M+H]⁺.

d) 2-(2-(4-(dimethylamino)methyl)-3-(trifluoromethyl)pyrazol-1-yl)acetamido)-4,5,6,7-tetrahydrobenzo[b]thiophene-3-carboxamide

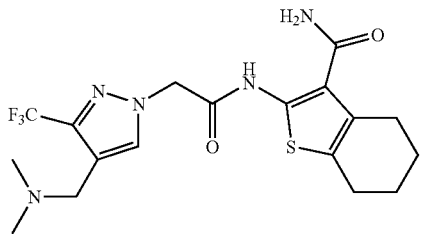

3-(trifluoromethyl)pyrazole-4-carbaldehyde (20 mg, 0.05 mmol) was dissolved in DCM (2 mL). Dimethylamine (10 µL, excess) was added followed by sodium triacetoxyborohydride (42 mg, 0.2 mmol), then catalytic acetic acid. The reaction mixture was stirred overnight, concentrated in vacuo, and DMF (1 mL) added. The sample was purified by preparative reverse phase HPLC to give the desired product as the TFA salt (6.5 mg, 0.012 mmol, 24%).

MS (ESI): m/z 430 [M+H]⁺.

EXAMPLE 55

2-(2-(4-(cyclopropylamino)methyl)-3-(trifluoromethyl)pyrazol-1-yl)acetamido)-4,5,6,7-tetrahydrobenzo[b]thiophene-3-carboxamide

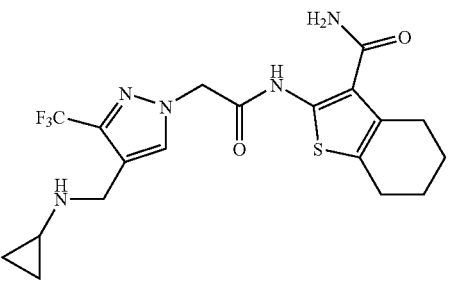

In a similar manner to example 54d, cyclopropylamine was used in place of dimethylamine to yield the title compound as the TFA salt (3.0 mg, 0.005 mmol, 11%).

MS (ESI): m/z 442 [M+H]⁺.

EXAMPLE 56

2-(2-(4-(diethylamino)methyl)-3-(trifluoromethyl)pyrazol-1-yl)acetamido)-4,5,6,7-tetrahydrobenzo[b]thiophene-3-carboxamide

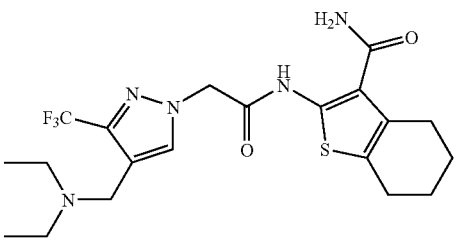

In a similar manner to example 54d, diethylamine was used in place of dimethylamine to yield the title compound as the TFA salt (8.9 mg, 0.016 mmol, 31%).

MS (ESI): m/z 548 [M+H]⁺.

EXAMPLE 57

2-(2-(4-(ethylamino)methyl)-3-(trifluoromethyl)pyrazol-1-yl)acetamido)-4,5,6,7-tetrahydrobenzo[b]thiophene-3-carboxamide

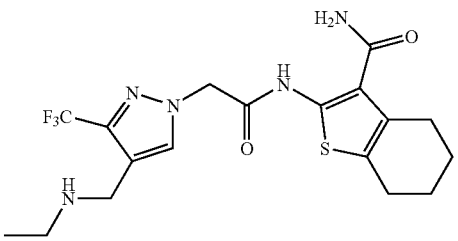

In a similar manner to example 54d, ethylamine (2.0 M solution in THF) was used in place of dimethylamine to yield the title compound as the TFA salt (11.8 mg, 0.022 mmol, 43%).

MS (ESI): m/z 430 [M+H]⁺.

EXAMPLE 58

2-(2-(4-((3-hydroxypropylamino)methyl)-3-(trifluoromethyl)pyrazol-1-yl)acetamido)-4,5,6,7-tetrahydrobenzo[b]thiophene-3-carboxamide

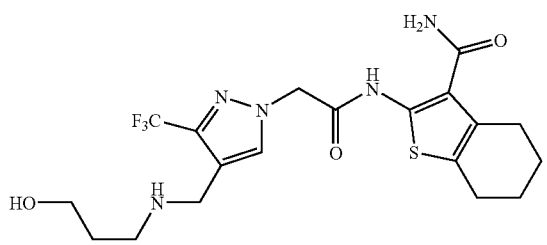

In a similar manner to example 54d, propanolamine was used in place of dimethylamine to yield the title compound as the TFA salt (2.9 mg, 0.005 mmol, 10%).

MS (ESI): m/z 460 [M+H]$^+$.

EXAMPLE 59

2-(2-(4-((2-methoxyethylamino)methyl)-3-(trifluoromethyl)pyrazol-1-yl)acetamido)-4,5,6,7-tetrahydrobenzo[b]thiophene-3-carboxamide

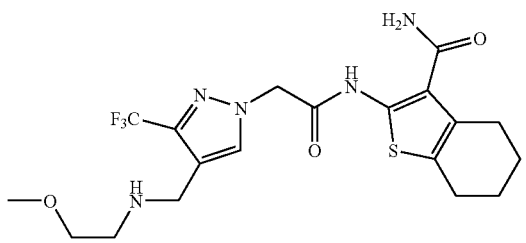

In a similar manner to example 54d, 2-methoxyethylamine was used in place of dimethylamine to yield the title compound as the TFA salt (8.8 mg, 0.015 mmol, 31%).

MS (ESI): m/z 460 [M+H]$^+$.

EXAMPLE 60

2-[2-(4-Azetidin-1-ylmethyl-3-trifluoromethyl-pyrazol-1-yl)-acetylamino]-4,5,6,7-tetrahydro-benzo[b]thiophene-3-carboxamide

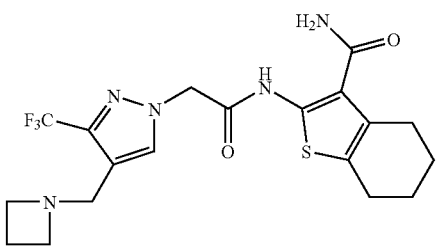

In a similar manner to example 54d, azetidine hydrochloride was used in place of dimethylamine to yield the title compound as the TFA salt. The sample was free based using SCX ion exchange chromatography to give the desired product (0.5 mg, 1 µmol, 2.3 MS (ESI): m/z 442 [M+H]$^+$.

EXAMPLE 61

2-[2-(4-Methylaminomethyl-3-trifluoromethyl-pyrazol-1-yl)-acetylamino]-4,5,6,7-tetrahydro-benzo[b]thiophene-3-carboxamide

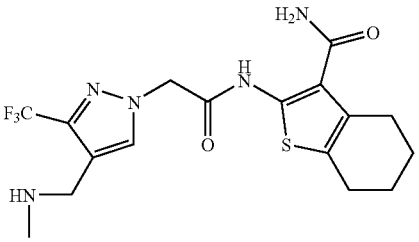

In a similar manner to example 54d, methylamine was used in place of dimethylamine to yield the title compound as the TFA salt. The sample was free based using SCX ion exchange chromatography to give the desired product (2.8 mg, 6.7 µmol, 2.3%).

MS (ESI): m/z 416 [M+H]$^+$.

EXAMPLE 62

2-(2-(4-hydroxymethyl)-3-(trifluoromethyl)pyrazol-1-yl)acetamido)-4,5,6,7-tetrahydrobenzo[b]thiophene-3-carboxamide

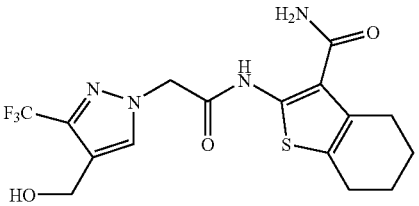

2-(2-(4-formyl-3-(trifluoromethyl)-pyrazol-1-yl)acetamido)-4,5,6,7-tetrahydrobenzo[b]thiophene-3-carboxamide (50 mg, 0.125 mmol) was dissolved in THF (3 mL). Sodium borohydride (10 mg, 0.264 mmol) was added and the reaction mixture stirred under N$_2$ for 30 min. The reaction mixture was concentrated in vacuo, dissolved in DMF (1 mL), filtered, and purified by preparative reverse phase HPLC to give desired product as a white solid (12 mg, 0.03 mmol, 24%).

MS (ESI): m/z 403 [M+H]$^+$.

EXAMPLE 63

2-{2-[4-(2-Hydroxy-ethyl)-3-trifluoromethylpyrazol-1-yl]-acetylamino}-4,5,6,7-tetrahydro-benzo[b]thiophene-3-carboxamide

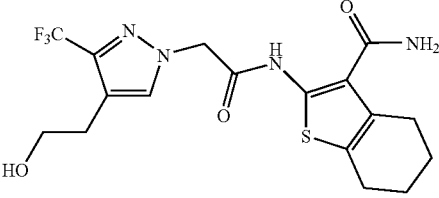

To a solution of 2-(3-trifluoromethylpyrazol-4-yl)-ethanol (18 mg, 0.1 mmol) in DMF (0.5 mL) was added potassium carbonate (16 mg, 0.12 mmol). The reaction mixture was stirred at 60° C. for 25 min before 2-(2-bromoacetamido)-4,5,6,7-tetrahydrobenzo[b]thiophene-3-carboxamide (32 mg, 0.1 mmol) was added. Heating at 60° C. was maintained for 4 h before the reaction mixture was allowed to cool to RT. The whole was diluted with MeOH (0.5 mL), and filtered before being purified by preparative reverse phase HPLC to give the desired product as a white solid (17 mg, 0.04 mmol, 41%).

MS (ESI): m/z 417 [M+H]⁺.

EXAMPLE 64

2-[2-(5-Hydroxymethyl-3-trifluoromethylpyrazol-1-yl)-acetylamino]-4,5,6,7-tetrahydrobenzo[b]thiophene-3-carboxamide a) (5-Trifluoromethyl-2H-pyrazol-3-yl)-methanol

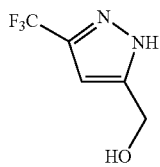

3-(Trifluoromethyl)pyrazole-5-carbonyl chloride (500 mg, 2.52 mmol) was dissolved in THF (10 mL). The reaction mixture was put under a $N_2$ atmosphere and $LiAlH_4$ (191 mg, 5.03 mmol) was added portionwise. The reaction mixture was stirred at RT for 2 days before adding MeOH (10 mL). The reaction mixture was concentrated in vacuo to give a grey solid. EtOAc (20 mL) was added and the crude reaction product stirred at RT for 30 min. The resulting solid was filtered off and the filtrate concentrated in vacuo to give the crude product which was used without further purification in the next step.

b) 2-[2-(5-Hydroxymethyl-3-trifluoromethylpyrazol-1-yl)-acetylamino]-4,5,6,7-tetrahydrobenzo[b]thiophene-3-carboxamide

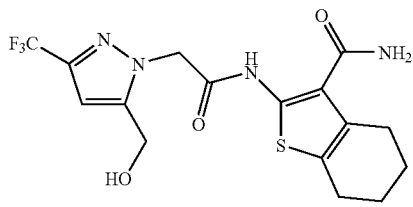

In a similar manner to example 63, (5-trifluoromethyl-2H-pyrazol-3-yl)-methanol was used in place of 2-(3-trifluoromethyl-1H-pyrazol-4-yl)-ethanol to yield the title compound (2 mg, 0.005 mmol, 5%).

MS (ESI): m/z 403 [M+H]⁺.

EXAMPLE 65

2-(2-(3-cyanoindazol-1-yl)acetamido)-4,5,6,7-tetrahydrobenzo[b]thiophene-3-carboxamide

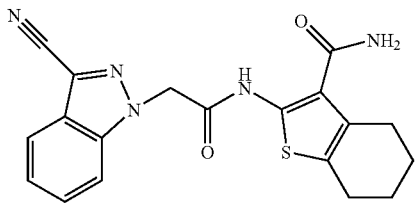

To a solution of 1H-indazole-3-carbonitrile (11 mg, 0.077 mmol) in DMF (500 μL) was added potassium carbonate and the whole was stirred at RT for 30 min before 2-(2-bromoacetamido)-4,5,6,7-tetrahydrobenzo[b]thiophene-3-carboxamide (24 mg, 0.077 mmol) was added. The reaction mixture was heated to 60° C. and this temperature was maintained for 1.5 h before the reaction mixture was cooled to RT, then diluted with water (5 mL). The organics were extracted with diethyl ether (10 mL), EtOAc (10 mL) and DCM (10 mL), then combined and the suspension concentrated to dryness. The residue was dissolved in DMSO (1 mL) and purified by preparative reverse phase HPLC to give the title compound as a white solid (4 mg, 0.01 mmol, 14%).

MS (ESI): m/z 380 [M+H]⁺.

EXAMPLE 66

2-(2-(4-(ethoxymethyl)-3-(trifluoromethyl)pyrazol-1-yl)acetamido)-4,5,6,7-tetrahydrobenzo[b]thiophene-3-carboxamide

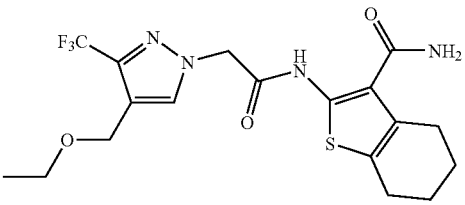

To a solution of 2-(2-(4-(hydroxymethyl)-3-(trifluoromethyl)pyrazol-1-yl)acetamido)-4,5,6,7-tetrahydrobenzo[b]thiophene-3-carboxamide (20 mg, 0.05 mmol) in DMF (2 mL) was added NaH (7 mg, 0.29 mmol) under an atmosphere of $N_2$. The reaction mixture was stirred at RT for 30 min before addition of iodoethane (20 mg, 0.13 mmol). The reaction mixture was heated at 65° C. for 3 h then left to stand at RT overnight. Water (2 mL) was added and the reaction mixture extracted with EtOAc (3×5 mL). The combined EtOAc layers were washed with water (3×10 mL), brine (10 mL), dried over $MgSO_4$ and the solvent removed in vacuo. The residue was purified by preparative reverse phase HPLC to give the desired product as a clear gum (6.7 mg, 0.016 mmol, 31%).

¹H NMR (400 MHz, $CD_3OD$): ☐1.20 (t, 3H), 1.83 (m, 4H), 2.67 (m, 2H), 2.72 (m, 2H), 3.54 (q, 2H), 4.51 (s, 2H), 5.18 (s, 2H), 7.88 (s, 1H).

EXAMPLE 67

2-(2-(4-(1-hydroxyethyl)-3-(trifluoromethyl)-1H-pyrazol-1-yl)acetamido)-4,5,6,7-tetrahydrobenzo[b]thiophene-3-carboxamide

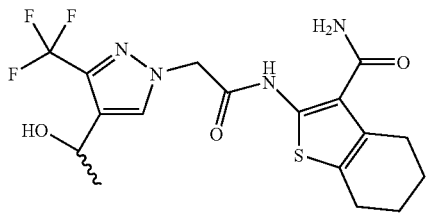

To 2-(2-(4-formyl-3-(trifluoromethyl)-1H-pyrazol-1-yl)acetamido)-4,5,6,7-tetrahydrobenzo[b]thiophene-3-carboxamide (1.6 g, 4.00 mmol) in THF (10 mL) at −50° C. under an argon atmosphere was added 3M methylmagnesium bromide in diethyl ether (1.249 mL, 3.75 mmol) in a dropwise manner over 10 min. The reaction was stirred at −50° C. for 1.5 h. The reaction was quenched with saturated aqueous $NH_4Cl$ before partitioning between EtOAc/water (×2), and washing with EtOAc (×1) and brine (×1). The organics were dried over $MgSO_4$ before removing the solvent in vacuo. The residue was purified by silica gel flash chromatography (1:2 heptane/EtOAc) and the solvent removed in vacuo to give the title compound as a yellow solid (0.8 g, 1.921 mmol, 48%).

MS (ESI): m/z 417.6 [M+H]⁺.

EXAMPLE 68

2-(2-(4-acetyl-3-(trifluoromethyl)-1H-pyrazol-1-yl)acetamido)-4,5,6,7-tetrahydrobenzo[b]thiophene-3-carboxamide

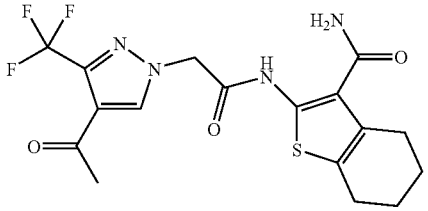

To 2-(2-(4-(1-hydroxyethyl)-3-(trifluoromethyl)-1H-pyrazol-1-yl)acetamido)-4,5,6,7-tetrahydrobenzo[b]thiophene-3-carboxamide (1.4 g, 3.36 mmol) in DCM (17 mL) was added a 15 wt % Dess-Martin periodinane in DCM solution (9.51 g, 6.99 mL, 3.36 mmol). The reaction was blanketed with argon and allowed to stir at RT for 6 h. Sodium thiosulfate pentahydrate (5.84 g, 23.53 mmol) was dissolved in water (20 mL) and mixed with saturated aqueous sodium bicarbonate (40 mL) before addition to the reaction mixture. The reaction mixture was allowed to stir for 40 min before the addition of diethyl ether. The aqueous was separated and extracted with diethyl ether (×3). The organics were combined and washed with water (×2) and brine (×1) before drying over MgSO$_4$. The solvent was removed in vacuo to give the title compound as an off white solid (1.2 g, 2.90 mmol, 86%).

MS (ESI): m/z 415.1 [M+H]$^+$.

EXAMPLE 69

2-(2-(4-(1-(methylamino)ethyl)-3-(trifluoromethyl)-1H-pyrazol-1-yl)acetamido)-4,5,6,7-tetrahydrobenzo[b]thiophene-3-carboxamide

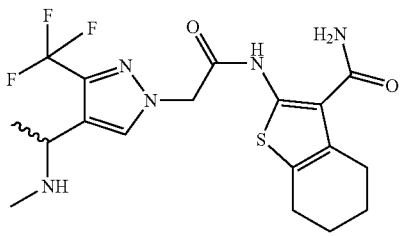

To MeOH (1.5 mL) was added 2M methylamine in THF (0.724 mL, 1.448 mmol). Acetic acid was added to the mixture to adjust the pH to 4-5. 2-(2-(4-acetyl-3-(trifluoromethyl)-1H-pyrazol-1-yl)acetamido)-4,5,6,7-tetrahydrobenzo[b]thiophene-3-carboxamide (50 mg, 0.121 mmol) and sodium cyanoborohyde (7.58 mg, 0.121 mmol) were added before heating the reaction to 100° C. for 30 min by microwave irradiation. The reaction mixture was quenched with water before purification by preparative reverse phase HPLC. The product fractions were acidified to pH 3 with acetic acid before applying to a strong cation exchange cartridge (500 mg). The cartridge was washed with DCM/MeOH (1:1) before eluting the product with 2M NH$_3$ in MeOH. The solvent was removed in vacuo to give the title compound (7.1 mg, 0.017 mmol, 14%).

MS (ESI): m/z 430.1 [M+H]$^+$.

EXAMPLE 70

2-(2-(4-(1-(2-hydroxyethylamino)ethyl)-3-(trifluoromethyl)-1H-pyrazol-1-yl)acetamido)-4,5,6,7-tetrahydrobenzo[b]thiophene-3-carboxamide

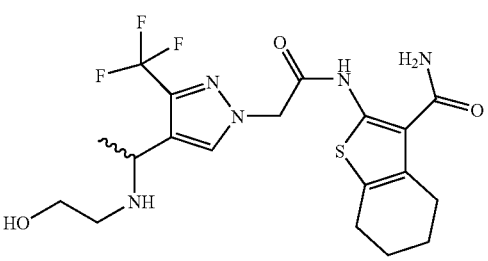

To a solution of 2-aminoethanol (103 mg, 1.689 mmol) in MeOH (1.5 mL), AcOH was added until the pH reached 5. 2-(2-(4-acetyl-3-(trifluoromethyl)-1H-pyrazol-1-yl)acetamido)-4,5,6,7-tetrahydrobenzo[b]thiophene-3-carboxamide (50 mg, 0.121 mmol) was added before the addition of (7.6 mg, 0.121 mmol) of sodium cyanoborohydride. The reaction was heated by microwave irradiation to 100° C. for 20 min. The reaction mixture was filtered before purification by preparative reverse phase HPLC. The product fractions were acidified to pH 4 before applying to a strong cation exchange cartridge (500 mg). The cartridge was washed with DCM/MeOH (1:1) before eluting the product with 2M NH$_3$ in MeOH. The solvent was removed in vacuo to give the title compound (8.3 mg, 0.018 mmol, 15%).

MS (ESI): m/z 460.5 [M+H]$^+$

EXAMPLE 71

2-(2-(4-(1-(2-fluoroethylamino)ethyl)-3-(trifluoromethyl)-1H-pyrazol-1-yl)acetamido)-4,5,6,7-tetrahydrobenzo[b]thiophene-3-carboxamide

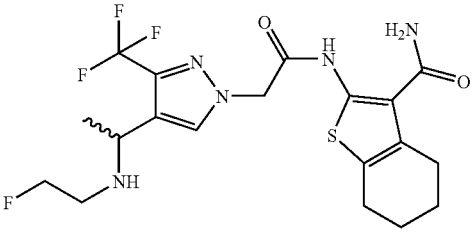

To a solution of 2-fluoroethanamine (107 mg, 1.689 mmol) in MeOH (1.5 mL), AcOH was added until the pH reached 5. 2-(2-(4-acetyl-3-(trifluoromethyl)-1H-pyrazol-1-yl)acetamido)-4,5,6,7-tetrahydrobenzo[b]thiophene-3-carboxamide (50 mg, 0.121 mmol) was added before the addition of sodium cyanoborohydride (7.58 mg, 0.121 mmol). The reaction was heated by microwave irradiation to 100° C. for 20 min. The reaction mixture was filtered before purification by preparative reverse phase HPLC. The product fractions were acidified to pH 4 before applying to a strong cation exchange cartridge (500 mg). The cartridge was washed with DCM/MeOH (1:1) before eluting the product with 2M NH$_3$ in MeOH. The solvent was removed in vacuo to give the title compound (2.9 mg, 0.006 mmol, 5%).

MS (ESI): m/z 462.5 [M+H]$^+$.

EXAMPLE 72

2-[2-(3-Tert-butyl-4-dimethylaminomethylpyrazol-1-yl)-acetylamino]-4,5,6,7-tetrahydrobenzo[b]thiophene-3-carboxamide a) Pinacolone Semicarbazone

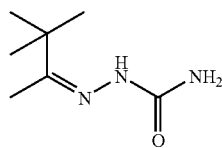

Pinacolone (10 g, 99.8 mmol) was added to a solution of semicarbazide hydrochloride (11.13 g, 99.8 mmol) and sodium acetate (16.4 g, 199 mmol) in water (60 mL). The mixture was stirred for 17 h at ambient temperature. The white precipitate was filtered and washed with water and diethyl ether. The solid was dried under vacuo at 50° C. to yield the desired product (11.09 g, 70.5 mmol, 71%).

MS (ESI): m/z 158.1[M+H]⁺.

b) 3-Tert-butyl-1H-pyrazole-4-carbaldehyde

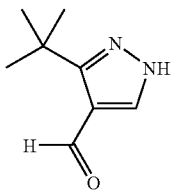

Phosphorus oxychloride (18.2 mL, 195 mmol) was added portionwise to DMF (30 mL, 387 mmol) at <5° C. Pinacolone semicarbazone (15.4 g, 97.6 mmol) was added over 1 h maintaining the temperature at <5° C. The reaction mixture became very thick so an additional quantity of DMF (10 mL) was added. The mixture was heated to 60° C. for 3.5 h then allowed to cool and poured into ice. The reaction was neutralised using sodium hydroxide (40 g, 1 mol) in water (130 mL) then heated at 60° C. for 5 min. The mixture was cooled in an ice bath and acidified to pH 6 and the product extracted into EtOAc. The EtOAc was dried over MgSO₄ and concentrated onto silica. The crude product was purified by flash chromatography using eluants EtOAc/heptane. Trituration in diethyl ether gave a white solid (1.02 g, 6.1 mmol, 6%).

1H NMR (400 MHz, CDCl₃): □1.48 (s, 9H), □8.07 (s, 1H), □10.06 (s, 1H) □10.25 (b, 1H).

c) 2-[2-(3-Tert-butyl-4-formyl-pyrazol-1-yl)-acetylamino]-4,5,6,7-tetrahydro-benzo[b]thiophene-3-carboxamide

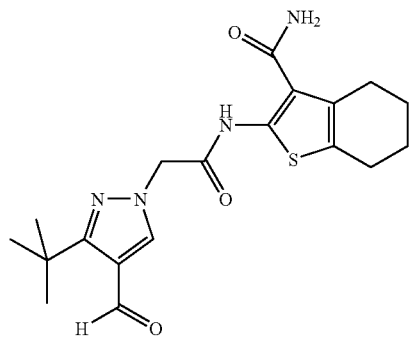

d) 3-Tert-butyl-1H-pyrazole-4-carbaldehyde (32.2 mg, 0.19 mmol) and potassium carbonate (40 mg, 1.5 mol eq) were mixed with DMF (0.5 mL) and stirred for 10 min at ambient temperature. 2-(2-bromoacetamido)-4,5,6,7-tetrahydrobenzo[b]thiophene-3-carboxamide (61 mg, 0.19 mmol) was added and the mixture heated to 60° C. for 2 h. Water was added and the crude product extracted with EtOAc. Purification using flash chromatography using eluants diethyl ether/DCM gave a yellow solid (58 mg, 0.15 mmol, 78%).

MS (ESI): m/z 389.4 [M+H]⁺.

e) 2-[2-(3-Tert-butyl-4-dimethylaminomethylpyrazol-1-yl)-acetylamino]-4,5,6,7-tetrahydro benzo[b]thiophene-3-carboxamide

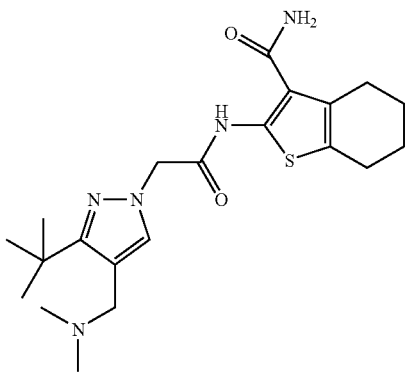

2-[2-(3-Tert-butyl-4-formylpyrazol-1-yl)-acetylamino]-4,5,6,7-tetrahydrobenzo[b]thiophene-3-carboxamide (50 mg, 0.13 mmol) and dimethylamine hydrochloride (20 mg, 0.23 mmol) were mixed with DMF (0.3 mL) and acetic acid (0.3 mL). Sodium triacetoxyborohydride (70 mg, 0.33 mmol) was added and the mixture stirred for 1 h. The reaction was quenched with MeOH and water and directly purified by preparative reverse phase HPLC. The clean product was passed down an SCX cartridge and the volatiles were blown off under a nitrogen atmosphere (2.1 mg, 5 μmol, 4%).

MS (ESI): m/z 418 [M+H]⁺.

EXAMPLE 73

2-(2-(3-Tert-butyl-4-((2-hydroxyethylamino)methyl)-1H-pyrazol-1-yl)acetamido)-4,5,6,7-tetrahydrobenzo[b]thiophene-3-carboxamide

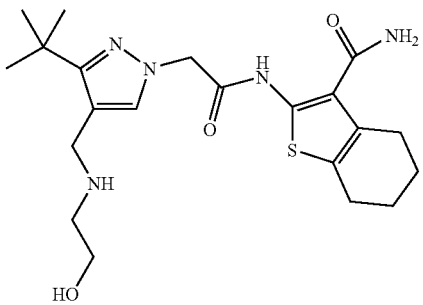

Ethanolamine (189 mg, 0.186 mL, 3.09 mmol) was added to a solution of 2-(2-(3-tert-butyl-4-formyl-1H-pyrazol-1-yl)acetamido)-4,5,6,7-tetrahydrobenzo[b]thiophene-3-carboxamide (120 mg, 0.309 mmol) and acetic acid (0.5 mL, 8.7 mmol) in DMF (3 mL) and stirred for 1 h. Sodium triacetoxyborohydride (655 mg, 3.09 mmol) was added and the mixture stirred for 17 h at ambient temperature. Water (500 μL) was added and the mixture stirred for 30 min. The mixture was filtered and purified by preparative reverse phase HPLC. The clean fractions were passed down an SCX cartridge and the free base eluted with 2M NH₃ in MeOH. Volatiles were blown down under a nitrogen atmosphere to yield the title compound (54.8 mg, 0.126 mmol, 41%).

MS (ESI): m/z 434.5 [M+H]⁺.

EXAMPLE 74

2-(2-(3-Tert-butyl-4-((ethylamino)methyl)-1H-pyrazol-1-yl)acetamido)-4,5,6,7-tetrahydrobenzo[b]thiophene-3-carboxamide

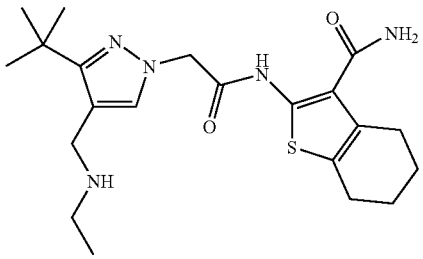

Ethylamine (175 mg, 0.205 mL, 3.89 mmol) was added to a solution of 2-(2-(3-tert-butyl-4-formyl-1H-pyrazol-1-yl)acetamido)-4,5,6,7-tetrahydrobenzo[b]thiophene-3-carboxamide (151 mg, 0.389 mmol) and acetic acid (0.5 mL) in DMF (2.5 mL). Sodium triacetoxyborohydride (824 mg, 3.89 mmol) was added and the mixture stirred for 17 h. Water (300 µL) was added and the reaction stirred for 30 min. The reaction was filtered and purified by preparative reverse phase HPLC. The clean fractions were passed down an SCX cartridge and the product eluted with 2M NH₃ in MeOH. Volatiles were blown down to give 2-(2-(3-tert-butyl-4-((ethylamino)methyl)-1H-pyrazol-1-yl)acetamido)-4,5,6,7-tetrahydrobenzo[b]thiophene-3-carboxamide (13 mg, 0.031 mmol, 8%).

MS (ESI): m/z 418.5 [M+H]⁺.

EXAMPLE 75

2-[2-(3-Tert-butyl-4-hydroxymethylpyrazol-1-yl)-acetylamino]-4,5,6,7-tetrahydrobenzo[b]thiophene-3-carboxamide

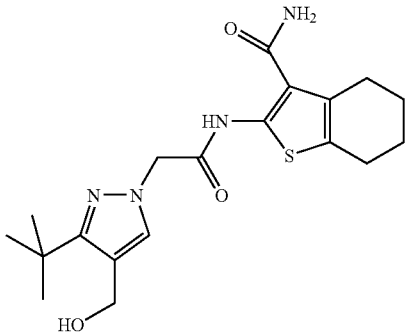

Sodium borohydride (50 mg, 1.3 mmol) was added to a solution of 2-[2-(3-tert-Butyl-4-formylpyrazol-1-yl)-acetylamino]-4,5,6,7-tetrahydro-benzo[b]thiophene-3-carboxamide (100 mg, 0.25 mmol) in THF (2 mL). The mixture was stirred for 1 h at ambient temperature. Water was added and the product extracted with EtOAc. The combined organics were dried over MgSO₄ and concentrated under reduced pressure. The crude product was purified by flash chromatography using eluants EtOAc/heptane. The solid isolated was further purified by preparative reverse phase HPLC and passed down an SCX cartridge. The volatiles were blown off with nitrogen to give a white solid (2.4 mg, 0.61 µmol, 2%).

MS (ESI): m/z 391 [M+H]⁺.

EXAMPLE 76

N-methyl-2-(2-(4-((methylamino)methyl)-3-(trifluoromethyl)-1H-pyrazol-1-yl)acetamido)-4,5,6,7-tetrahydrobenzo[b]thiophene-3-carboxamide a) 2-Amino-N-methyl-4,5,6,7-tetrahydrobenzo[b]thiophene-3-carboxamide

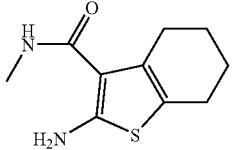

Cyclohexanone (3.70 g, 37.7 mmol), 2-cyano-N-methylacetamide (3.70 g, 37.7 mmol), and sulphur (1.21 g, 37.7 mmol) were stirred in EtOH (15 mL). Diethylamine (5.60 mL, 54.1 mmol) was added and the reaction mixture stirred at 20° C. for 5 days. The crude material was directly preabsorbed onto silica. Purification by flash chromatography (eluent 0-100% EtOAc:heptane) gave the desired product as a yellow solid (1.51 g, 7.18 mmol, 19%).

1H NMR (400 MHz, CDCl₃): □1.60 (m, 4H), 2.45 (m, 2H), 2.57 (m, 2H), 2.69 (d, 3H), 6.62 (s, 2H), 6.69 (s, 1H).

b) 2-(2-Bromoacetamido)-N-methyl-4,5,6,7-tetrahydrobenzo[b]thiophene-3-carboxamide

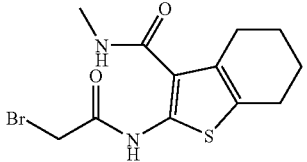

In a similar manner to example 50a, 2-amino-N-methyl-4,5,6,7-tetrahydrobenzo[b]thiophene-3-carboxamide was used in place of 2-amino-4,5,6,7-tetrahydrobenzo[b]thiophene-3-carboxamide to yield the title compound as a yellow solid (0.67 g, 2.02 mmol, 71%).

MS (ESI): m/z 333 [M+H]⁺.

c) 2-(2-(4-Formyl-3-(trifluoromethyl)-1H-pyrazol-1-yl)acetamido)-N-methyl-4,5,6,7-tetrahydrobenzo[b]thiophene-3-carboxamide

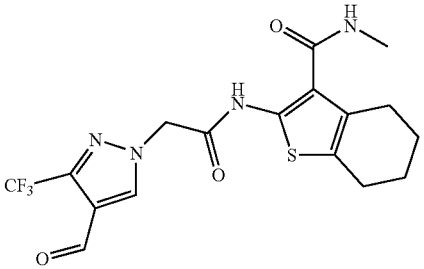

3-(Trifluoromethyl)pyrazole-4-carbaldehyde (332 mg, 2.02 mmol) was dissolved in THF (10 mL). Potassium tert-butoxide (454 mg, 4.05 mmol) was added, followed by 2-(2-bromoacetamido)-N-methyl-4,5,6,7-tetrahydrobenzo[b]thiophene-3-carboxamide (670 mg, 2.02 mmol). The reaction mixture was stirred at RT overnight. Aqueous NH₄Cl (10 mL) was added and the reaction mixture extracted with DCM (3×10 mL). The combined DCM layers were washed with sodium bicarbonate solution (5×10 mL). The aqueous was separated using hydrophobic filter paper and the solvent removed in vacuo to give the desired product as a brown foam (0.73 g, 1.76 mmol, 87%).

MS (ESI): m/z 415 [M+H]+.

d) N-methyl-2-(2-(4-((methylamino)methyl)-3-(trifluoromethyl)-1H-pyrazol-1-yl)acetamido)-4,5,6,7-tetrahydrobenzo[b]thiophene-3-carboxamide

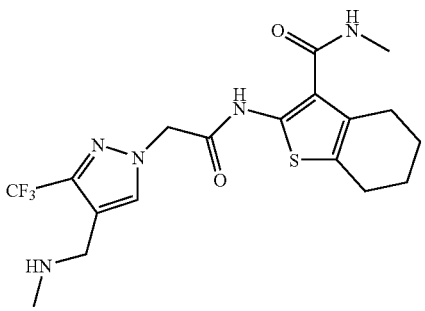

2-(2-(4-Formyl-3-(trifluoromethyl)-1H-pyrazol-1-yl)acetamido)-N-methyl-4,5,6,7-tetrahydrobenzo[b]thiophene-3-carboxamide (338 mg, 0.816 mmol) was dissolved in NMP (10 mL) and methylamine hydrochloride (275 mg, 4.08 mmol) added, followed by glacial acetic acid (0.5 mL). The resulting mixture was stirred at RT for 5 min, before portionwise addition of sodium triacetoxyborohydride (691 mg, 3.26 mmol). The reaction was stirred at RT overnight. The reaction was quenched with water, and diluted with DCM (10 mL) and saturated sodium bicarbonate solution (10 mL). The phases were separated and the aqueous extracted with DCM (2×10 mL). The combined organics were concentrated to a brown oil which was loaded on to an SCX column and eluted with MeOH, then 2N NH3 in MeOH. The fractions were monitored by TLC (DCM, 10% MeOH) and combined to give a brown residue (160 mg). Plurification by flash chromatography (eluent 5-10-20% MeOH:DCM) gave the desired product as a yellow/brown oil which solidified on standing (106 mg, 0.25 mmol, 30%).

MS (ESI): m/z 430 [M+H]+.

EXAMPLE 77

2-(2-(4-((2-Hydroxyethylamino)methyl)-3-(trifluoromethyl)-1H-pyrazol-1-yl)acetamido)-N-methyl-4,5,6,7-tetrahydrobenzo[b]thiophene-3-carboxamide

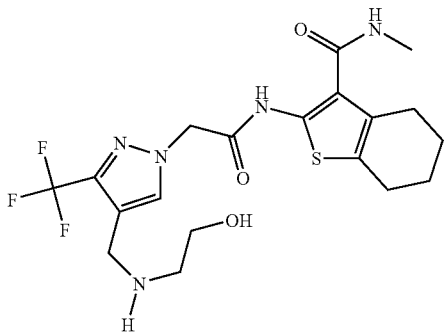

In a similar manner to example 76d, ethanolamine was used in place of methylamine hydrochloride to yield the title compound (3 mg, 0.007 mmol, 8%).

MS (ESI): m/z 460 [M+H]+.

EXAMPLE 78

2-(2-(3-Tert-butyl-4-formyl-1H-pyrazol-1-yl)acetamido)-N-methyl-4,5,6,7-tetrahydrobenzo[b]thiophene-3-carboxamide

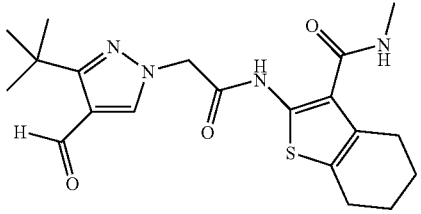

3-Tert-butyl-1H-pyrazole-4-carbaldehyde (150 mg, 0.986 mmol), 2-(2-bromoacetamido)-N-methyl-4,5,6,7-tetrahydrobenzo[b]thiophene-3-carboxamide (490 mg, 1.478 mmol) and potassium carbonate (545 mg, 3.94 mmol) were mixed with DMF (5 mL) and heated for 3 h at 60° C. The reaction was partitioned between water and EtOAc. Organics were combined and purified by chromatography (0-60%, EtOAc/heptane) to give the title product as a white solid (360 mg, 0.894 mmol, 91%).

MS (ESI): m/z 403.6 [M+H]+.

EXAMPLE 79

2-(2-(3-Tert-butyl-4-((methylamino)methyl)-1H-pyrazol-1-yl)acetamido)-N-methyl-4,5,6,7-tetrahydrobenzo[b]thiophene-3-carboxamide

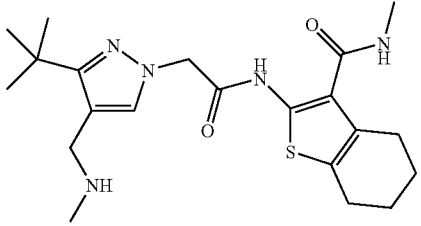

Methylamine (45.0 mg, 50 μl, 1.449 mmol) was added to a solution of 2-(2-(3-tert-butyl-4-formyl-1H-pyrazol-1-yl)acetamido)-N-methyl-4,5,6,7-tetrahydrobenzo[b]thiophene-3-carboxamide (100 mg, 0.248 mmol) and acetic acid (100 μl, 1.74 mmol) in DMF (1 mL). Sodium triacetoxyborohydride (527 mg, 2.484 mmol) was added and the reaction stirred for 17 h. The reaction was quenched with water (500 μl) and purified by preparative reverse phase HPLC. The clean fractions were passed down an SCX cartridge and eluted with 2M NH3 in MeOH. Volatiles were blown down under a nitrogen atmosphere to yield the title product (33 mg, 0.079 mmol, 32%).

MS (ESI): m/z 418.4 [M+H]+.

EXAMPLE 80

N-(2-hydroxyethyl)-2-(2-(4-((methylamino)methyl)-3-(trifluoromethyl)-1H-pyrazol-1-yl)acetamido)-4,5,6,7-tetrahydrobenzo[b]thiophene-3-carboxamide a) 2-Cyano-N-(2-hydroxyethyl)acetamide

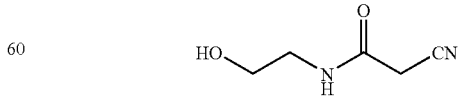

To a solution of ethyl 2-cyanoacetate (10 g, 9.41 mL, 88 mmol) in EtOH (100 mL) was added 2-aminoethanol (5.40 g, 5.34 mL, 88 mmol). The mixture was refluxed for 4 h before concentration in vacuo. The mixture was purified on a 100 g Silica column eluting with 0-10% MeOH/DCM. Desired fractions were collected and concentrated to yield the desired product as a brown oil (10.2 g, 79.7 mmol, 90%). The sample was used directly in the next step without any further purification.

b) 2-Cyano-2-cyclohexylidene-N-(2-hydroxyethyl) acetamide

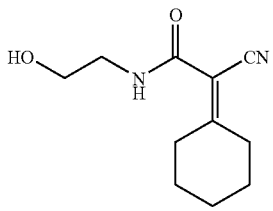

2-Cyano-N-(2-hydroxyethyl)acetamide (4.62 g, 36.1 mmol), cyclohexanone (3.89 g, 4.10 mL, 39.7 mmol), acetic acid (0.433 g, 0.413 mL, 7.21 mmol) and ammonium acetate (2.78 g, 36.1 mmol) were suspended in toluene (150 mL) and the mixture heated to reflux under Dean-Stark conditions until no more water was collected (~1.5 h). The mixture was concentrated to remove toluene before partitioning between EtOAc/Water. The organic phase was collected, dried and concentrated to a lower volume before addition of small quantities of heptane. The glass was etched until precipitation occurred and the solid collected by filtration. The desired product was isolated in 3 batches (4.2 g, 20.2 mmol, 56%). The sample was used directly in the next step without any further purification.

c) 2-Amino-N-(2-hydroxyethyl)-4,5,6,7-tetrahydrobenzo[b]thiophene-3-carboxamide

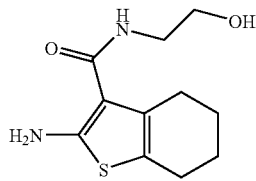

2-Cyano-2-cyclohexylidene-N-(2-hydroxyethyl)acetamide (3.70 g, 17.77 mmol) was dissolved in EtOH (75 mL) and sulfur (1.14 g, 35.5 mmol) followed by diethylamine (2.60 g, 3.68 mL, 35.5 mmol) added. The mixture was heated to reflux for 30 min. The reaction mixture was filtered while warm and the solid washed with EtOH. The combined EtOH portions were concentrated to dryness to yield the title product as a dark solid (4.6 g, 19.19 mmol, 108%). The sample was used directly in the next step without any further purification.

d) 2-(2-Bromoacetamido)-N-(2-hydroxyethyl)-4,5,6,7-tetrahydrobenzo[b]thiophene-3-carboxamide

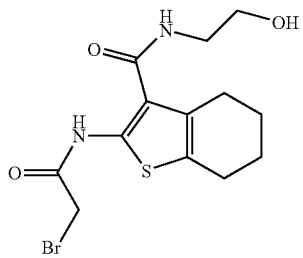

2-Amino-N-(2-hydroxyethyl)-4,5,6,7-tetrahydrobenzo[b]thiophene-3-carboxamide (4.6 g, 19.14 mmol) and DIPEA (4.95 g, 6.33 mL, 38.3 mmol) were dissolved in THF (100 mL) and the mixture purged with nitrogen and cooled in an ice bath. 2-Bromoacetyl bromide (3.86 g, 1.667 mL, 19.14 mmol) dissolved in THF (5 mL) was added dropwise and the reaction monitored by TLC. After 30 min TLC indicated 3:1 product: starting material with a faint spot for bis-acylated material. An additional quantity of 2-bromoacetyl bromide (0.97 g, 0.417 µL, 4.79 mmol) was added and stirring continued for a further 30 min. The mixture was quenched by addition of water before removal of THF under reduced pressure. The mixture was then partitioned between EtOAc/water and the organic layer collected—additional DCM was added to aid solubility. The aqueous layer was further washed with DCM. Combined organics were dried and concentrated to give a thick dark oil which was purified on silica eluting with 20-60% EtOAc/heptane. Desired fractions were collected and concentrated to yield the desired product as a light yellow solid (2.96 g, 8.23 mmol, 43%). The sample was used directly in the next step without any further purification.

e) 2-(2-(4-Formyl-3-(trifluoromethyl)-1H-pyrazol-1-yl)acetamido)-N-(2-hydroxyethyl)-4,5,6,7-tetrahydrobenzo[b]thiophene-3-carboxamide

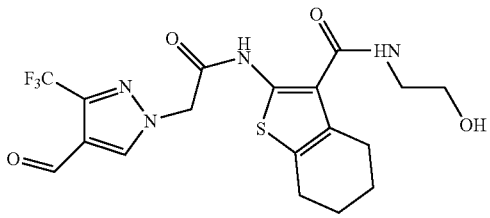

2-(2-Bromoacetamido)-N-(2-hydroxyethyl)-4,5,6,7-tetrahydrobenzo[b]thiophene-3-carboxamide (2.91 g, 8.06 mmol) was dissolved in DMF (25 mL) and potassium carbonate (2.23 g, 16.11 mmol), followed by 3-(trifluoromethyl)-1H-pyrazole-4-carbaldehyde (1.39 g, 8.46 mmol), added. The mixture was stirred at 60° C. for 25 min after which time the reaction mixture was diluted with water (~800 mL), then acidified with 5 N HCl until pH 1. During acidification a free flowing solid was obtained which was collected by filtration. NMR analysis indicated ~60-70% purity of desired product. The solid was successfully triturated with a mixture of DCM/ether to give a light beige solid which was collected by filtration. The mother liquor was concentrated and a second batch obtained using a similar process. The batches were combined to yield the title product (1.76 g, 3.95 mmol, 49%).

MS (ESI): m/z 443.5 [M−H]⁻.

f) N-(2-hydroxyethyl)-2-(2-(4-((methylamino)methyl)-3-(trifluoromethyl)-1H-pyrazol-1-yl)acetamido)-4,5,6,7-tetrahydrobenzo[b]thiophene-3-carboxamide

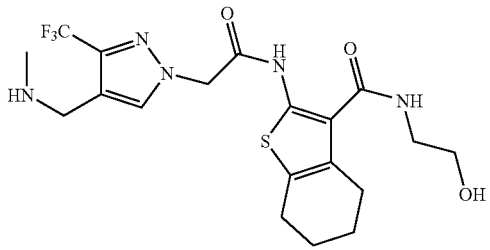

2-(2-(4-Formyl-3-(trifluoromethyl)-1H-pyrazol-1-yl)acetamido)-N-(2-hydroxyethyl)-4,5,6,7-tetrahydrobenzo[b]thiophene-3-carboxamide (100 mg, 0.225 mmol), Methylamine (2 M in THF, 0.45 mL, 0.90 mmol) and DCM (3 mL) were treated with acetic acid (13.51 mg, 0.225 mmol) to give pH 4-5 and the solution stirred at RT for 20 min. 10% Pd/C (20 mg) was added as a slurry in DCM and the mixture stirred under 4 barr hydrogen overnight. The mixture was taken into a 20 mL syringe and the residue of the flask washed with MeOH/DCM and also taken into the syringe. The mixture was filtered through a filter tip and concentrated to give a yellow oil (~200 mg). Purification was achieved on silica eluting with 4% 2 M $NH_3$ in MeOH/DCM and the product obtained as a light yellow glass (74.2 mg, 0.160 mmol, 71%).

MS (ESI): m/z 458.5 $[M-H]^-$.

EXAMPLE 81

2-(2-(4-((Ethylamino)methyl)-3-(trifluoromethyl)-1H-pyrazol-1-yl)acetamido)-N-(2-hydroxyethyl)-4,5,6,7-tetrahydrobenzo[b]thiophene-3-carboxamide

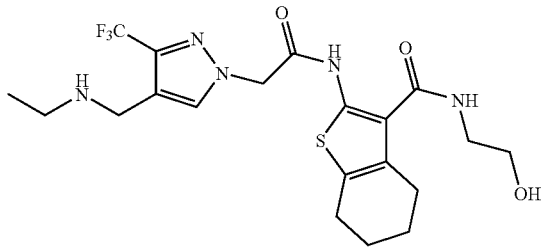

In a similar manner to example 80f, ethylamine was used instead of methylamine to yield the title compound (180 mg, 0.35 mmol, 51%).

MS (ESI): m/z 472.6 $[M-H]^-$.

EXAMPLE 82

2-(2-(4-((Dimethylamino)methyl)-3-(trifluoromethyl)-1H-pyrazol-1-yl)acetamido)-N-(2-hydroxyethyl)-4,5,6,7-tetrahydrobenzo[b]thiophene-3-carboxamide

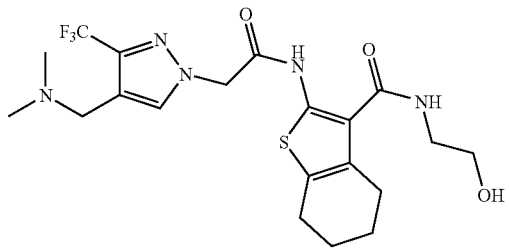

2-(2-(4-Formyl-3-(trifluoromethyl)-1H-pyrazol-1-yl)acetamido)-N-(2-hydroxyethyl)-4,5,6,7-tetrahydrobenzo[b]thiophene-3-carboxamide (30 mg, 0.068 mmol), Dimethylamine (2M solution in THF, 0.169 mL, 0.34 mmol) and DMF (1 mL) were treated with acetic acid (5 drops) and sodium triacetoxyborohydride (57.2 mg, 0.270 mmol) and the mixture stirred at RT overnight. The sample was filtered and purified by preparative reverse phase HPLC followed by additional purification by SCX ion exchange chromatography to yield the title compound (13.5 mg, 0.029 mmol, 42%).

MS (ESI): m/z 474.5 $[M+H]^+$.

EXAMPLE 83

N-(2-hydroxyethyl)-2-(2-(4-((2,2,2-trifluoroethylamino)methyl)-3-(trifluoromethyl)-1H-pyrazol-1-yl)acetamido)-4,5,6,7-tetrahydrobenzo[b]thiophene-3-carboxamide

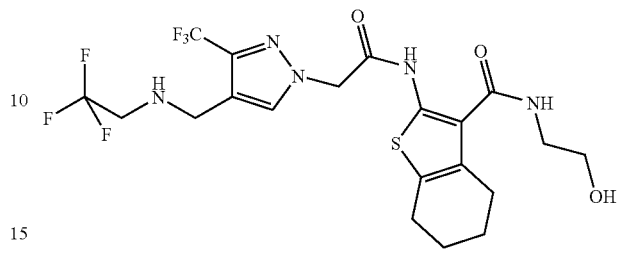

2-(2-(4-Formyl-3-(trifluoromethyl)-1H-pyrazol-1-yl)acetamido)-N-(2-hydroxyethyl)-4,5,6,7-tetrahydrobenzo[b]thiophene-3-carboxamide (30 mg, 0.068 mmol), 2,2,2-trifluoroethylamine (19.8 mg, 0.20 mmol) and DCM (1 mL) were treated with acetic acid (5 drops) and sodium triacetoxyborohydride (58 mg, 0.272 mmol) and the mixture stirred at RT overnight. The sample was concentrated and re-dissolved in dimethylsulfoxide (1 mL), filtered and purified by preparative LCMS followed by additional purification by SCX ion exchange chromatography to yield the title compound (10 mg, 0.02 mmol, 29%).

MS (ESI) m/z 528.5 $[M+H]^+$

EXAMPLE 84

2-(2-(3-Tert-butyl-4-formyl-1H-pyrazol-1-yl)acetamido)-N-(2-hydroxyethyl)-4,5,6,7-tetrahydrobenzo[b]thiophene-3-carboxamide

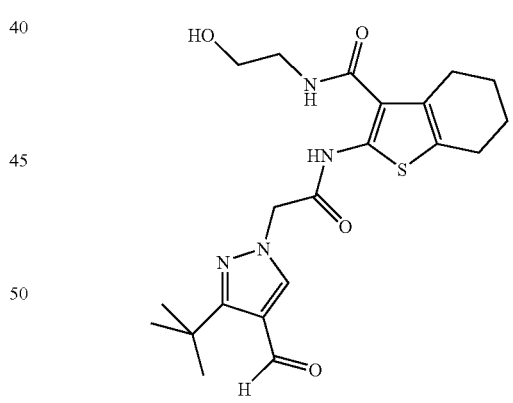

2-(2-Bromoacetamido)-N-(2-hydroxyethyl)-4,5,6,7-tetrahydrobenzo[b]thiophene-3-carboxamide (1.66 g, 4.60 mmol), 3-tert-butyl-1H-pyrazole-4-carbaldehyde (1.75 g, 11.49 mmol) and potassium carbonate (2.54 g, 18.38 mmol) were mixed with DMF (20 mL) and heated at 70° C. for 2 h. On cooling, the reaction was partitioned between EtOAc and water. The organics were washed with brine, dried over $MgSO_4$ and concentrated directly onto silica for chromatographic purification (0-100% EtOAc/heptane). Concentration in vacuo yielded a white solid (1.64 g, 3.79 mmol, 83%).

MS (ESI): m/z 433.5 $[M+H]^+$.

EXAMPLE 85

2-(2-(3-Tert-butyl-4-((ethylamino)methyl)-1H-pyrazol-1-yl)acetamido)-N-(2-hydroxyethyl)-4,5,6,7-tetrahydrobenzo[b]thiophene-3-carboxamide

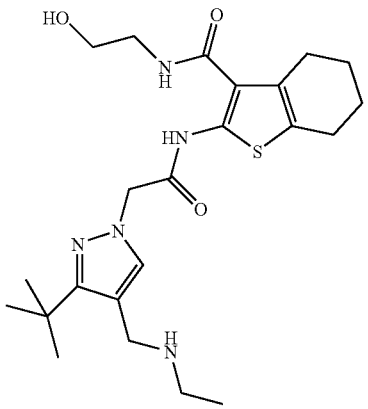

2-(2-(3-Tert-butyl-4-formyl-1H-pyrazol-1-yl)acetamido)-N-(2-hydroxyethyl)-4,5,6,7-tetrahydrobenzo[b]thiophene-3-carboxamide (1.66 g, 3.84 mmol) was dissolved in DCM (40 mL) and acetic acid (20.98 g, 20 mL, 349 mmol). Ethylamine (2M in THF, 7.68 mL, 15.35 mmol) was added and the mixture was stirred for 90 min. A slurry of palladium on charcoal (10%, 1.51 g, 1.420 mmol) in DCM (30 mL) was added and the mixture hydrogenated at 4 barr for 72 h at 20° C. The catalyst was filtered through dicalite and the dicalite washed with water, DCM and MeOH. All volatiles were removed under reduced pressure and the aqueous residue was basified to pH 8 using sodium bicarbonate. The crude product was extracted with EtOAc. The organics were combined and washed with brine, dried over MgSO$_4$, filtered and concentrated. The crude material was purified by chromatography (DCM, 0-30% MeOH/DCM and 0-20% 7 N NH$_3$ in MeOH/DCM). Concentration in vacuo yielded a white solid (800 mg, 1.73 mmol, 45%).

MS (ESI): m/z 462.5 [M+H]$^+$.

EXAMPLE 86

2-(3-(4-((Methylamino)methyl)-3-(trifluoromethyl)-1H-pyrazol-1-yl)propanamido)-4,5,6,7-tetrahydrobenzo[b]thiophene-3-carboxamide a) 2-(3-(4-Formyl-3-(trifluoromethyl)-1H-pyrazol-1-yl)propanamido)-4,5,6,7-tetrahydrobenzo[b]thiophene-3-carboxamide

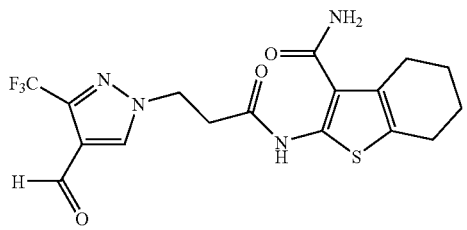

3-(Trifluoromethyl)-1H-pyrazole-4-carbaldehyde (260 mg, 1.585 mmol) and 2-(3-chloropropanamido)-4,5,6,7-tetrahydrobenzo[b]thiophene-3-carboxamide (454 mg, 1.585 mmol) were dissolved in THF (20 mL). Potassium tert-butoxide (356 mg, 3.17 mmol) was added followed by potassium iodide (10 mg, 0.06 mmol). The reaction mixture was stirred at RT overnight. Water was added and the reaction mixture extracted with EtOAc (×3). The EtOAc layers were combined and washed with brine, dried over MgSO$_4$, filtered and the solvent removed in vacuo to give a yellow gum (673 mg). Purification by flash column chromatography-silica gel gave the desired product as a white solid (180 mg, 0.43 mmol, 27%).

MS (ESI): m/z 415.1 [M+H]$^+$.

b) 2-(3-(4-((Methylamino)methyl)-3-(trifluoromethyl)-1H-pyrazol-1-yl)propanamido)-4,5,6,7-tetrahydrobenzo[b]thiophene-3-carboxamide

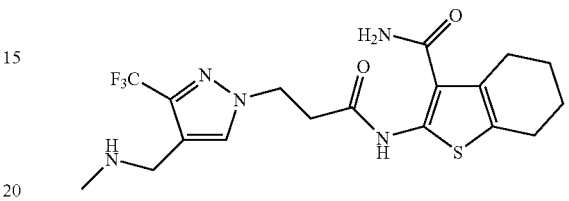

2-(3-(4-Formyl)-3-(trifluoromethyl)-1H-pyrazol-1-yl)propanamido)-4,5,6,7-tetrahydrobenzo[b]thiophene-3-carboxamide (50 mg, 0.121 mmol) was dissolved in DCM/DMF (2:1, 3 mL). Methylamine (2M in THF, 3.57 mg, 0.121 mmol) was added, followed by acetic acid (0.7 mg, 0.012 mmol). The reaction mixture was stirred at RT for 30 min before addition of sodium triacetoxyborohydride (102 mg, 0.483 mmol). The reaction mixture was stirred at RT overnight. The DCM was removed in vacuo and the reaction mixture filtered, then purified by preparative reverse phase HPLC to give the desired product as the TFA salt. The sample was passed through an SCX column, washed with MeOH, then eluted with 2 M NH$_3$ in MeOH to give the desired product (6.4 mg, 0.015 mmol, 12%).

MS (ESI): m/z 430.5 [M+H]$^+$.

EXAMPLE 87

2-(3-(4-((2-Fluoroethylamino)methyl)-3-(trifluoromethyl)-1H-pyrazol-1-yl)propanamido)-4,5,6,7-tetrahydrobenzo[b]thiophene-3-carboxamide

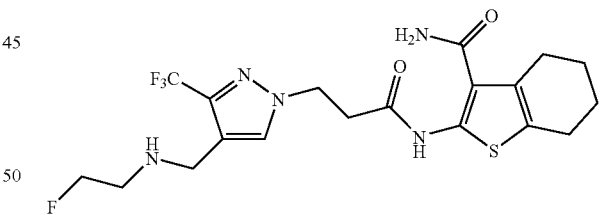

2-(3-(4-Formyl)-3-(trifluoromethyl)-1H-pyrazol-1-yl)propanamido)-4,5,6,7-tetrahydrobenzo[b]thiophene-3-carboxamide (25 mg, 0.06 mmol) was dissolved in DCM/DMF (2:1, 3 mL). 2-Fluoroethylamine (3.57 mg, 0.06 mmol) was added, followed by acetic acid (0.36 mg, 0.006 mmol). The reaction mixture was stirred at RT for 30 min before addition of sodium triacetoxyborohydride (51 mg, 0.242 mmol). The reaction mixture was stirred at RT overnight. The DCM was removed in vacuo and the reaction mixture filtered, then purified by preparative reverse phase HPLC to give the desired product as the TFA salt. The sample was passed through an SCX column, washed with MeOH, then eluted with 2 M NH$_3$ in MeOH to give the desired product (8.8 mg, 0.019 mmol, 32%).

MS (ESI): m/z 462.1 [M+H]$^+$.

EXAMPLE 88

2-(3-(4-((2-Hydroxyethylamino)methyl)-3-(trifluoromethyl)-1H-pyrazol-1-yl)propanamido)-4,5,6,7-tetrahydrobenzo[b]thiophene-3-carboxamide

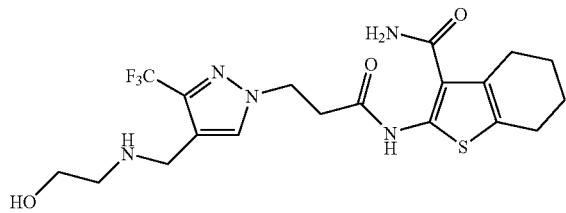

2-(3-(4-Formyl)-3-(trifluoromethyl)-1H-pyrazol-1-yl)propanamido)-4,5,6,7-tetrahydrobenzo[b]thiophene-3-carboxamide (25 mg, 0.06 mmol) was dissolved in DCM/DMF (2:1, 3 mL). 2-Hydroxyethylamine (14.7 mg, 0.241 mmol) was added, followed by acetic acid (0.36 mg, 0.006 mmol). The reaction mixture was stirred at RT for 30 min before addition of sodium triacetoxyborohydride (51 mg, 0.242 mmol). The reaction mixture was stirred at RT overnight. The DCM was removed in vacuo and the reaction mixture filtered, then purified by preparative reverse phase HPLC to give the desired product as the TFA salt. The sample was passed through an SCX column, washed with MeOH, then eluted with 2 M $NH_3$ in MeOH to give desired product (1.5 mg, 0.003 mmol, 5%).

MS (ESI): m/z 460.4 $[M+H]^+$.

EXAMPLE 89

N-methyl 2-(3-(4-((methylamino)methyl)-3-(trifluoromethyl)-1H-pyrazol-1-yl)propanamido)-4,5,6,7-tetrahydrobenzo[b]thiophene-3-carboxamide a) 2-(3-Chloropropanamido)-N-methyl-4,5,6,7-tetrahydrobenzo[b]thiophene-3-carboxamide

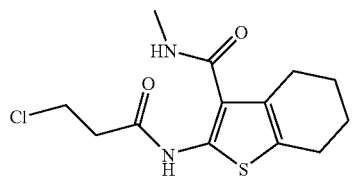

2-Amino-N-methyl-4,5,6,7-tetrahydrobenzo[b]thiophene-3-carboxamide (2.82 g, 13.41 mmol) was completely dissolved in THF (90 mL). Potassium carbonate (2.22 g, 16.09 mmol) was then added and the reaction stirred for 5 min. 3-chloropropanoyl chloride (2.04 g, 1.536 mL, 16.09 mmol) was added and the reaction mixture stirred at RT for 30 min. THF was removed in vacuo. Water was added and the reaction mixture extracted into EtOAc (×3). The combined EtOAc layers were washed with brine, dried over $MgSO_4$, filtered and the solvent removed in vacuo. Purification by flash column chromatography-silica gel and elution with 0-60% EtOAc:heptane gave the desired product (1.76 g, 5.87 mmol, 44%).

MS (ESI): m/z 301.3 $[M+H]^+$.

b) 2-(3-(4-Formyl-3-(trifluoromethyl)-1H-pyrazol-1-yl)propanamido)-N-methyl-4,5,6,7-tetrahydrobenzo[b]thiophene-3-carboxamide

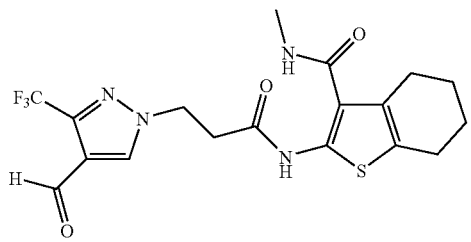

3-(Trifluoromethyl)-1H-pyrazole-4-carbaldehyde (437 mg, 2.66 mmol) and 2-(3-chloropropanamido)-N-methyl-4,5,6,7-tetrahydrobenzo[b]thiophene-3-carboxamide (801 mg, 2.66 mmol) were dissolved in DMF (15 mL). Potassium carbonate (368 mg, 2.66 mmol) was added followed by potassium iodide (10 mg, 0.06 mmol). The reaction mixture was left to stand for 7 days. Water was added and the reaction mixture extracted into EtOAc (×3). The EtOAc layers were combined and washed with water (×5), brine, dried over $MgSO_4$, filtered and the solvent removed in vacuo to give desired product as a yellow solid (970 mg, 2.26 mmol, 85%).

MS (ESI): m/z 429.3 $[M+H]^+$.

c) N-methyl 2-(3-(4-((methylamino)methyl)-3-(trifluoromethyl)-1H-pyrazol-1-yl)propanamido)-4,5,6,7-tetrahydrobenzo[b]thiophene-3-carboxamide

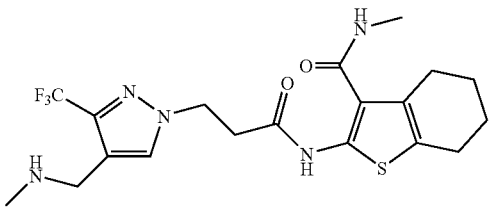

2-(3-(4-Formyl)-3-(trifluoromethyl)-1H-pyrazol-1-yl)propanamido)-N-methyl-4,5,6,7-tetrahydrobenzo[b]thiophene-3-carboxamide (25 mg, 0.058 mmol) was dissolved in DCM/DMF (2:1, 3 mL). Methylamine (1.81 mg, 0.058 mmol) was added, followed by acetic acid (0.36 mg, 0.006 mmol). The reaction mixture was stirred at RT for 30 min before addition of sodium triacetoxyborohydride (51 mg, 0.242 mmol). The reaction mixture was stirred at RT overnight. The DCM was removed in vacuo and the reaction mixture filtered, then purified by preparative reverse phase HPLC to give the desired product as the TFA salt. The sample was passed through an SCX column, washed with MeOH, then eluted with 2 M $NH_3$ in MeOH to give the desired product (5.1 mg, 0.012 mmol, 20%).

MS (ESI): m/z 444.5 $[M+H]^+$.

EXAMPLE 90

2-(2-(4-(2-(Methylamino)ethyl)-3-(trifluoromethyl)-1H-pyrazol-1-yl)acetamido)-4,5,6,7-tetrahydrobenzo[b]thiophene-3-carboxamide a) 2-(1-(2-(3-Carbamoyl-4,5,6,7-tetrahydrobenzo[b]thiophen-2-ylamino)-2-oxoethyl)-3-(trifluoromethyl)1H-pyrazol-4-yl)ethyl methane sulfonate

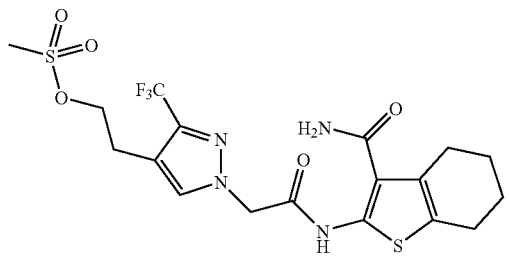

2-(2-(4-(2-Hydroxyethyl)-3-(trifluoromethyl)-1H-pyrazol-1-yl)acetamido)-4,5,6,7-tetrahydrobenzo[b]thiophene-3-carboxamide (Example 64, 480 mg, 1.153 mmol) was dissolved in DCM (10 mL). Triethylamine (117 mg, 1.153 mmol) was added, followed by methanesulfonyl chloride (132 mg, 1.153 mmol). The reaction mixture was stirred at RT for 3 h. Water was added and the reaction mixture extracted with DCM (×3). The combined DCM layers were then washed with brine, dried over MgSO$_4$, filtered and the solvent removed in vacuo to yield the desired product (450 mg, 0.91 mmol, 79%).

MS (ESI): m/z 495.4 [M+H]$^+$.

b) 2-(2-(4-(2-(Methylamino)ethyl)-3-(trifluoromethyl)-1H-pyrazol-1-yl)acetamido)-4,5,6,7-tetrahydrobenzo[b]thiophene-3-carboxamide

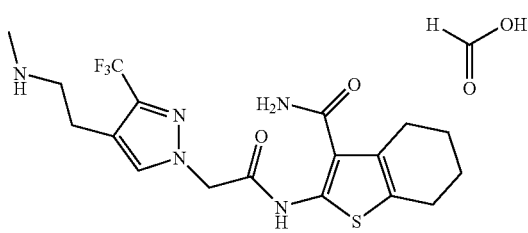

The 2-(1-(2-(3-carbamoyl-4,5,6,7-tetrahydrobenzo[b]thiophen-2-ylamino)-2-oxoethyl)-3-(trifluoromethyl)1H-pyrazol-4-yl)ethyl methanesulfonate (30 mg, 0.061 mmol) was dissolved in DMF (1 mL) and methylamine (2 M in THF, 1 mL, 2 mmol) added. The reaction mixture was heated at 120° C. for 5 min in the microwave. The THF was removed in vacuo and the reaction mixture filtered and purified by preparative reverse phase HPLC to give the formic acid salt of the desired product (3.6 mg, 0.008 mmol, 12%).

MS (ESI): m/z 430.5 [M+H]$^+$.

EXAMPLE 91

2-(2-(3-(Trifluoromethyl)-1H-pyrazolo[4,3-c]pyridin-1-yl)acetamido)-4,5,6,7-tetrahydrobenzo[b]thiophene-3-carboxamide a) 1-(4-(dimethylamino)pyridin-3-yl)-2,2,2-trifluoroethanone

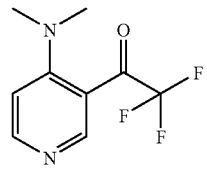

To a solution of N,N-dimethylpyridin-4-amine (500 mg, 4.09 mmol) in toluene (5 mL) was added 2,2,2-trifluoroacetic anhydride (430 mg, 0.284 mL, 2.046 mmol). The reaction mixture was heated to 85° C. and this temperature was maintained for 8 h before the mixture was allowed to cool to RT overnight. The precipitate (DMAP-TFA salt) was removed by filtration and the filtrate concentrated to dryness to give the desired product as a light brown oil (330 mg, 1.5 mmol, 37%).

MS (ESI): m/z 219 [M+H]$^+$.

b) 3-(Trifluoromethyl)-1H-pyrazolo[4,3-c]pyridine

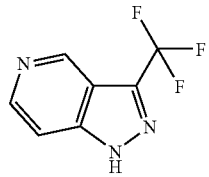

A suspension of 1-(4-(dimethylamino)pyridin-3-yl)-2,2,2-trifluoroethanone (259 mg, 1.187 mmol) and hydrazine monohydrochloride (244 mg, 3.56 mmol) in butan-1-ol (2.5 mL) was heated to 200° C. for 35 min. The reaction mixture was applied to a 10 g SPE cartridge that had been pre-conditioned with 3% MeOH/DCM and eluted with the same system to give a light yellow solid (189 mg, 1.0 mmol, 85%).

MS (ESI): m/z 188 [M+H]$^+$.

c) 2-(2-(3-(Trifluoromethyl)-1H-pyrazolo[4,3-c]pyridin-1-yl)acetamido)-4,5,6,7-tetrahydrobenzo[b]thiophene-3-carboxamide

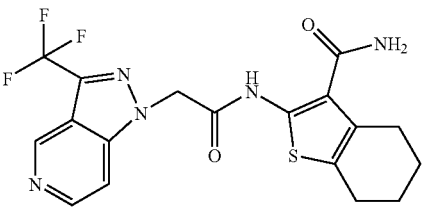

A mixture of 3-(trifluoromethyl)-1H-pyrazolo[4,3-c]pyridine (20 mg, 0.107 mmol), 2-(2-bromoacetamido)-4,5,6,7-tetrahydrobenzo[b]thiophene-3-carboxamide (33.9 mg, 0.107 mmol) and potassium carbonate (29.5 mg, 0.214 mmol) in DMF (0.5 mL) was heated to 60° C. and this temperature maintained for 2 h. The reaction mixture was allowed to cool to RT, and purified by preparative reverse phase HPLC to give a white solid (2.1 mg, 5 μmol, 4.6%).

MS (ESI): m/z 424 [M+H]$^+$.

EXAMPLE 92

N-methyl-2-(2-(3-(trifluoromethyl)-1H-pyrazolo[4,3-c]pyridin-1-yl)acetamido)-4,5,6,7-tetrahydrobenzo[b]thiophene-3-carboxamide

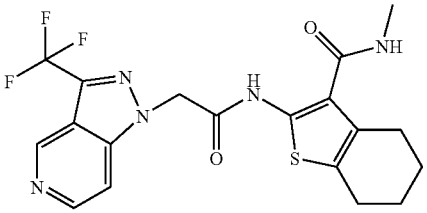

In a similar manner to example 91c, 2-(2-bromoacetamido)-N-methyl-4,5,6,7-tetrahydrobenzo[b]thiophene-3-carboxamide was used in place of 2-(2-bromoacetamido)-4,5,6,7-tetrahydrobenzo[b]thiophene-3-carboxamide to give the title compound as a white solid (8.1 mg, 19 μmol, 17%).

MS (ESI): m/z 438 [M+H]$^+$.

EXAMPLE 93

Biological Assays

The compounds in this invention may be tested using a biological assay which measures $Ca^{2+}$ influx mediated through positive modulation of the AMPA (GluR1) receptor using standard techniques in the art such as, but not limited to, a FLEXstation (manufactured by Molecular Devices, Sunnyvale, Calif.). An optical readout using fluorescent probes is employed to measure ion channel dependent changes in intracellular ion concentration or membrane potential. The assay utilises the $Ca^{2+}$ conductance of functional homomeric GluR1(i) AMPA receptors to generate glutamate-dependent $Ca^{2+}$ responses. Influx of $Ca^{2+}$ through the ion channel is measured indirectly through an increase in intracellular $Ca^{2+}$ levels using the calcium sensitive dye such as, but not limited to, Fluo-3 (Molecular Devices, Sunnyvale, Calif.) in FLEXstation. A positive AMPA receptor modulator, in the presence of glutamate, will result in an influx of $Ca^{2+}$ through the ion channel which can be measured indirectly through an increase in intracellular $Ca^{2+}$ levels using the calcium sensitive dye Fluo-3 in FLEXstation.

HEK.GluR1(i) cells were maintained in DMEM supplemented with 10% fetaclone II, 1% non-essential amino acids and 150 μg/mL hygromycin, at 37° C./5% CO2. Twenty-four h prior to the assay, the cells were harvested with trypsin and seeded onto Costar 96 well clear bottomed black plates at a density of 3.5×10$^4$ per well. Cells were loaded with 5 μM fluo3-AM in DMEM media in the absence of hygromycin and incubated at 37° C./5% $CO_2$ for one h. After dye loading, the cells were washed once with 200 μl of low calcium solution (10 mM hepes, pH 7.4, 160 mM NaCl, 4.5 mM KCl, 2 mM $CaCl_2$, 1 mM $MgCl_2$, 10 mM glucose) containing 0.625 mM of probenecid (inhibitor for the anion-exchange protein) to remove the dye. Then 200 μl of low calcium solution was added to each well. The Flexstation added 50 μl of glutamate+/−test compound in high calcium solution (10 mM Hepes, pH 7.4, 160 mM NaCl, 4.5 mM KCl, 20 mM $CaCl_2$, 1 mM $MgCl_2$ and 10 mM glucose) to each well and the ensuing response was monitored on FLEXstation.

The compounds of this invention exhibit positive modulation of the AMPA receptor having $EC_{50}$ values in the range 0.001 μM to 30 μM. For instance, Example 67 gave an $C_{50}$ of 2.2 μM.

What is claimed is:
1. A heterocyclic derivative according to formula I

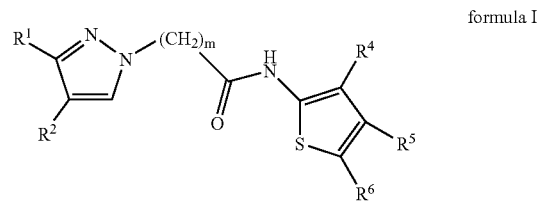

formula I wherein
$R^1$ is $C_{1-4}$alkyl or CN, said $C_{1-4}$alkyl being optionally substituted with 1-3 halogens;
$R^2$ is $C_{1-4}$alkyl, $C_{1-4}$alkyloxy, or $C_{1-5}$acyl, said $C_{1-4}$alkyl being optionally substituted with a substituent selected from OH, $C_{1-4}$alkyloxy and $NR^7R^8$ or $R^2$ together with $R^3$ forms a 5 to 7 membered unsaturated carbocyclic ring optionally comprising a N;
$R^3$ is H or methyl optionally substituted with hydroxy or 1-3 halogens or $R^3$ together with $R^2$ forms a 5 to 7 membered unsaturated carbocyclic ring optionally comprising a N;
$R^4$ is hydroxymethyl, $CO_2H$ or $CONR^9R^{10}$;
$R^5$ and $R^6$ are independently H, $C_{1-4}$alkyl or $C_{3-8}$cycloalkyl or $R^5$ together with $R^6$ forms a 5 or 6 membered unsaturated carbocyclic ring optionally comprising a heteroatomic moiety selected from O and $NR^{11}$;
$R^7$ and $R^8$ are independently H, $C_{1-6}$alkyl or $C_{3-8}$cycloalkyl, said $C_{1-6}$alkyl being optionally substituted with hydroxy, $C_{1-4}$ alkyloxy or 1-3 halogens; or $R^7$ and $R^8$ together with the N to which they are bonded form a 3-6 membered saturated heterocyclic ring;
$R^9$ is H or $C_{1-4}$alkyl optionally substituted with 1-3 groups selected from hydroxy, $C_{1-6}$ alkyloxy, $NR^{12}R^{13}$, $CONR^{14}R^{15}$ and Y, wherein Y is a 5-6 membered heteroaryl comprising 1-2 heteroatoms selected from O, N and S, or wherein Y is $C_{3-8}$cycloalkyl optionally comprising 1-2 heteroatomic moieties selected from O, S, $SO_2$ and $NR^{16}$, Y being optionally substituted with 1-2 substituents selected from $C_{1-4}$alkyl, $CH_2OH$ and $CH_2NR^{17}R^{18}$;
or $R^9$ is $C_{3-8}$cycloalkyl comprising a heteroatomic moiety selected from O, S and $NR^{16}$;
or $R^9$ and $R^{10}$ together with the N to which they are bonded form a 5-6 membered saturated heterocyclic ring optionally comprising a heteroatomic moiety selected from O and $NR^{16}$;
$R^{10}$ is H or methyl with the proviso that when $R^9$ is methyl $R^{10}$ must be $C_{1-4}$alkyl or
$R^{10}$ and $R^9$ together with the N to which they are bonded form a 5-6 membered saturated heterocyclic ring optionally comprising a heteroatomic moiety selected from O and $NR^{16}$;
$R^{11}$ is H or methyl;
$R^{12}$ is H or $C_{1-4}$alkyl or $R^{12}$ and $R^{13}$ together with the N to which they are bonded form a 5-6 membered saturated heterocyclic ring optionally comprising a heteroatomic moiety selected from O, S and $NR^{19}$;
$R^{13}$ is H, $C_{1-4}$alkyl, $CO_2R^{20}$ or $SO_2R^{20}$ or $R^{13}$ and $R^{12}$together with the N to which they are bonded form a 5-6 membered saturated heterocyclic ring optionally comprising a heteroatomic moiety selected from O, S and $NR^{19}$;
$R^{14}$-$R^{19}$ are independently H or $C_{1-4}$alkyl;
$R^{20}$ is $C_{1-4}$alkyl; and
m is 1-4;
with the proviso that when $R^1$ is $CF_3$, $R^2$ together with $R^3$ forms a 6 membered unsaturated carbocyclic ring and R⁵ together with R⁶ forms a 6 membered unsaturated carbocyclic ring, R⁴ cannot be CONH₂;
or a pharmaceutically acceptable salt thereof.

2. The heterocyclic derivative according to claim 1, wherein R¹ is CF₃.

3. The heterocyclic derivative according to claim 1, wherein R² is methyl optionally substituted with hydroxy or NR⁷R⁸.

4. The heterocyclic derivative according to claim 1, wherein R² together with R³ forms a 5 to 7 membered unsaturated carbocyclic ring.

5. The heterocyclic derivative according to claim 1, wherein R⁴ is CONR⁹R¹⁰ and wherein R⁹ and R¹⁰ have the previously defined meanings.

6. The heterocyclic derivative according to claim 1, wherein R⁵ together with R⁶ forms a 5 to 7 membered unsaturated carbocyclic ring optionally comprising an O.

7. The heterocyclic derivative according to claim 1, wherein m is 1.

8. A heterocyclic derivative selected from
   2-[2-(3-Trifluoromethyl-4,5,6,7-tetrahydro-indazol-1-yl)-acetylamino]-4,5,6,7-tetrahydro-benzo[b]thiophene-3-carboxylic acid (3-hydroxy-propyl)-amide;
   2-[2-(3-Trifluoromethyl-4,5,6,7-tetrahydro-indazol-1-yl)-acetylamino]-4,5,6,7-tetrahydro-benzo[b]thiophene-3-carboxylic acid (2-methanesulfonylamino-ethyl)-amide;
   2-[2-(3-Trifluoromethyl-4,5,6,7-tetrahydro-indazol-1-yl)-acetylamino]-4,5,6,7-tetrahydro-benzo[b]thiophene-3-carboxylic acid azetidin-3-ylamide;
   2-(2-(3-(trifluoromethyl)-4,5-dihydro-1H-indazole-1-yl)acetamido-4,5,6,7-tetrahydrothieno[2,3-c]pyran-3-carboxamide;
   2-[2-(4-ethylaminomethyl-3-trifluoromethyl-pyrazol-1-yl)-acetylamino]-4,5,6,7-tetrahydro-benzo[b]thiophene-3-carboxamide;
   2-(2-(4-hydroxymethyl)-3-(trifluoromethyl)-1H-pyrazol-1-yl)acetamido)-4,5,6,7-tetrahydrobenzo[b]thiophene-3-carboxamide;
   2-{2-[4-(1-Hydroxy-ethyl)-3-trifluoromethyl-pyrazol-1-yl]-acetylamino}-4,5,6,7-tetrahydro-benzo[b]thiophene-3-carboxamide;
   2-[2-(3-tert-Butyl-4-dimethylaminomethyl-pyrazol-1-yl)-acetylamino]-4,5,6,7-tetrahydro-benzo[b]thiophene-3-carboxamide and
   N-(2-hydroxyethyl)-2-(2-(4-((methylamino)methyl)-3-(trifluoromethyl)-1H-pyrazol-1-yl)acetamido)-4,5,6,7-tetrahydrobenzo[b]thiophene-3-carboxamide and a pharmaceutically acceptable salt thereof.

9. A pharmaceutical composition comprising a heterocyclic derivative according to claim 1 or a pharmaceutically acceptable salt thereof in admixture with a pharmaceutically acceptable auxiliary.

10. A pharmaceutical composition comprising a heterocyclic derivative according to claim 8 or a pharmaceutically acceptable salt thereof in admixture with a pharmaceutically acceptable auxiliary.

* * * * *